(12) United States Patent
Gref et al.

(10) Patent No.: US 10,159,738 B2
(45) Date of Patent: Dec. 25, 2018

(54) ORGANIC-INORGANIC HYBRID SOLID HAVING A MODIFIED OUTER SURFACE

(71) Applicants: CENTRE NATIONAL DE LA RECHERCHE SCIENTIFIQUE-CNRS, Paris (FR); UNIVERSITE DE VERSAILLES-SAINT QUENTIN EN YVELINES, Versailles (FR); UNIVERSITE PARIS-SUD, Orsay (FR)

(72) Inventors: Ruxandra Gref, Verrieres-le Buisson (FR); Valentina Agostoni, Le Plesis-robinson (FR); Samia Daoud-Mahammed, Sceaux (FR); Violeta Rodriguez-Ruiz, Paris (FR); Milo Malanga, Bologne (IT); Laszlo Jicsinszky, Budapest (HU); Patricia Horcajada-Cortes, Chaville (FR); Christian Serre, Plaisir (FR)

(73) Assignees: CENTRE NATIONAL DE LA RECHERCHE SCIENTIFIQUE-CNRS, Paris (FR); UNIVERSITE DE VERSAILLES-SAINT QUENTIN EN YVELINES, Versailles (FR); UNIVERSITE PARIS-SUD, Orsay (FR)

( * ) Notice: Subject to any disclaimer, the term of this patent is extended or adjusted under 35 U.S.C. 154(b) by 697 days.

(21) Appl. No.: 14/403,277

(22) PCT Filed: May 30, 2013

(86) PCT No.: PCT/FR2013/051219
§ 371 (c)(1),
(2) Date: Feb. 23, 2015

(87) PCT Pub. No.: WO2013/178954
PCT Pub. Date: Dec. 5, 2013

(65) Prior Publication Data
US 2015/0150981 A1 Jun. 4, 2015

(30) Foreign Application Priority Data
May 31, 2012 (FR) .................... 12 55065

(51) Int. Cl.
| | |
|---|---|
| A61K 47/26 | (2006.01) |
| A61K 47/24 | (2006.01) |
| C08B 37/02 | (2006.01) |
| C08B 37/16 | (2006.01) |
| C08B 37/08 | (2006.01) |
| C07F 9/38 | (2006.01) |
| C07F 3/06 | (2006.01) |
| C07F 15/02 | (2006.01) |
| C07F 7/00 | (2006.01) |
| C07F 5/06 | (2006.01) |

(52) U.S. Cl.
CPC .............. *A61K 47/26* (2013.01); *A61K 47/24* (2013.01); *C07F 3/06* (2013.01); *C07F 5/061* (2013.01); *C07F 7/006* (2013.01); *C07F 9/3873* (2013.01); *C07F 15/025* (2013.01); *C08B 37/003* (2013.01); *C08B 37/0012* (2013.01); *C08B 37/0021* (2013.01)

(58) Field of Classification Search
CPC .... A61K 47/24; A61K 47/26; C08B 37/0012; C08B 37/0021; C08B 37/003; C07F 3/06; C07F 5/061; C07F 7/006; C07F 9/3873; C07F 15/025
See application file for complete search history.

(56) References Cited

U.S. PATENT DOCUMENTS

| | | | |
|---|---|---|---|
| 4,329,332 A | 5/1982 | Couvreur et al. | |
| 2010/0209354 A1* | 8/2010 | Horcajada-Cortes | ............ C07F 15/025 424/9.6 |
| 2011/0052650 A1* | 3/2011 | Morris | ............ A61K 8/02 424/401 |

FOREIGN PATENT DOCUMENTS

| | | |
|---|---|---|
| WO | 2009077670 A1 | 6/2009 |
| WO | 2009077671 A1 | 6/2009 |

OTHER PUBLICATIONS

A. M. Badawi et al. "Surface and biocidal activity of some synthesized metallo azobenzene isothiouronium salts", Bioorganic & Medicinal Chemistry, 2006, vol. 14, pp. 8661-8665.

Ajay Kumar Gupta et al. "Recent advances on surface engineering of magnetic iron oxide nanoparticles and their biomedical applications", Future Medicine Ltd, Nanomedicine, 2007, vol. 2, No. 1, pp. 23-39.

Ana E. Platero-Prats et al. "Dynamic Calcium Metal-Organic Framework Acts as a Selective Organic Solvent Sponge", Chemistry,2010, vol. 16, pp. 11632-11640.

Bernard Baleux et al. "Chimie Analytique—Dosage colorimetrique d'agents de surface non ioniques polyoxyethylenes a l'aide d'une solution iodo-ioduree", C.R. Acad. Sc. Paris, May 8, 1972, vol. 274, pp. 1617-1620.

C. Serre et al. "Evidence of flexibility in the nanoporous iron(III) carboxylate MIL-89", Dalton Transactions, 2008, pp. 5462-5464.

C. Serre et al. "Role of Solvent-Host Interactions That Lead to Very Large Swellng of Hybrid Frameworks", Science, 2007, vol. 315, pp. 1828-1831.

Caroline Mellot-Draznieks et al. "Very Large Swelling in Hybrid Frameworks: A combined Computational and Powder Diffraction Study", Journal of American Chemical Soceity, 2005, vol. 127, pp. 16273-16278.

(Continued)

*Primary Examiner* — Joseph R Kosack
(74) *Attorney, Agent, or Firm* — Cantor Colburn LLP

(57) ABSTRACT

The present invention concerns metal-organic hybrid solids having a modified outer surface. These solids can be used, for example, for the storage and vectoring of molecules of interest such as pharmaceutically active ingredients, compounds of interest in cosmetics and markers, for example contrast agents. These solids have good results in terms of active drug loading capacities, biocompatibility, stability and controlling the release of the active ingredients encapsulated.

20 Claims, 16 Drawing Sheets

(56) References Cited

OTHER PUBLICATIONS

Chester T. Dziobkowski et al. "Magnetic Properties and Mossbauer Spectra of Several Iron(III)-Dicarboxylic Acid Complexes ", Inorg. Chem., 1981, vol. 20, pp. 671-678.

Christian Serre et al. "A Route to the Synthesis of Trivalent Transition-Metal Porous Carboxylates with Trimeric Secondary Building Units", Nano Material, Angew.Chem. Int. Ed, 2004, vol. 43, pp. 6286-6289.

Christophe Volkringer et al. "Hydrothermal Crystallization of Three Calcium-Based Hybrid Solids with 2,6-napthalene- or 4,4'-Biphenyl-Dicarboxylates", Crystal Growth & Design, 2008, vol. 8, No. 2, pp. 685-689.

Chuan Yang et al. "Cationic start polymers consisting of x-cyclodextrin core and oligoethylenimine arms as nonviral gene delivery vectors", Biomaterials, 2007, vol. 28, pp. 3245-3254.

Claudia Zlotea et al. "Effect of NH2 and CF3 functionalization on the hydrogen sorption properties of MOFs", Dalton Transactions, 2011, vol. 40, pp. 4879-4881.

E. Renard et al. "Preparation and Characterization of water Soluble High Molecular Weight B-Cyclodextrin-Epichlorohydrin Polymers", Eur. Polym. J., 1997, vol. 33, No. 1, pp. 49-57.

Elif Yilmaz Ozmen et al. "Synthesis of B-cyclodextrin and starch based polymers for sorptio of azo dyes from aqueous solutions", Bioresource Technology, 2008, vol. 99, pp. 526-531.

G. Ferey et al. "A Chromium Terephthalate-Based Solid with Unusually Large Pore Volumes and Surface Area", Science, 2005, vol. 309, pp. 2040-2042.

Gyula Oros et al. "Separation of the strength and selectivity of the microbiological effect of synthetic dyes by spectral mapping technique", Chemosphere, 2003, vol. 52, pp. 185-193.

Jasmina Hafizovic Cavka et al. "A New Zirconium Inorganic Building Brick Forming Metal Organic Frameworks with Exceptional Stability", J. Am. Chem. Soc., 2008, vol. 130, pp. 13850-13851.

Jerome Bouligand et al. "Busulphan-loaded long-circulating nanospheres, a very attractive challenge for both galenists and pharmacologists", Journal of Microencapsulation, Dec. 2007, vol. 24, No. 8, pp. 715-730.

Julie A. Wieland et al. "Non-viral vector delivery from PEG-hyaluronic acid hydrogels", J. Control Release, Jul. 31, 2007, vol. 120, No. 3, pp. 233-241.

Kyo Sung Park et al. "exceptional chemical and thermal stability of zeolitic imidazolate frameworks", PNAS, Jul. 5, 2006, vol. 103, No. 27, pp. 1016-10191.

Luis C. Cesteros et al. "Hydrogels of B-cyclodextrin crosslinked by acylated poly(ethylene glycol): Synthesis and properties", European Polymer Journal, 2009, vol. 45, pp. 674-679.

M. Hassan et al. "A phase II trial of liposomal busulphan as an intravenous myeloablativ agent prior to stem cell transplantation: 50 mg/m2 as a optima total dose for conditioning" Bone Marrow Transplant, 2002, vol. 30, No. 12, pp. 833-841.

Mathivathani Kandiah et al. "Synthesis and Stability of Tagged UiO-66 Zr-MOFs", Chemistry of Materials, 2010, vol. 22, pp. 6632-6640.

Meenakshi Dan-Hardi et al. "A New Phtoactive Crystallne Highly Porous Titanium(IV) Dicarboxylate", > J. Am. Chem. Soc., 2009, vol. 131, pp. 10857-10859.

Narayan Bhattarai et al. "PEG-grafted chitosan as an injectable thermosensitive hydrogel for sustained protein release", Journal of Controlled Release, 2005, vol. 103, pp. 609-624.

Nicolas Blanchemain et al. "Polyester vascular prostheses coated with a cyclodextrin polymer and activated with antibiotics: Cytotoxicity and microbiological evaluation", Acta Biomaterialia, 2008, vol. 4, pp. 1725-1733.

Patricia Horcajada et al. "How Linker's Modification Controls Swelling Properties of Highly Flexible Iron(III) Dicarboxylates MIL-88", Journal of the American Chemical Society, 2011, vol. 133, pp. 17839-17847.

Patricia Horcajada et al. "Synthesis and catalytic properties of MIL-100(Fe), an iron (III) carboxylate with large pores", ChemComm, 2007, pp. 2820-2822.

Peter Caravan, "Strategies for increasing the sensitivity of gadolinium based MRI contrast agents", Chemical Society, The Royal Society of Chemistry, 2006, vol. 35, pp. 512-523.

Raghavendra S. Navath et al. "Injectable PAMAM dendrimer-PEG hydrogels for the treatment of genital infections: formulation in-vitro and in-vitro evaluation", Mol Pharm. Aug. 1, 2011, vol. 8, No. 4, pp. 1209-1223.

Ronald C. Hedden et al. "Structure and Dimensions of PAMAM/ PEG Dendrimer-Star Polymers" Marcromolecules, 2003, vol. 36, pp. 1829-1835.

Ruxandra Gref "New self-assembled nanogels based on host-guest interactions: Characterization and drug loading", Journal of Conrolled Release, 2006, vol. 111, pp. 316-324.

S. Daoud-Mahammed et al. "Novel self-assembling nanogels: Stability and lyophilisation studies", International Journal of Pharamceutics, 2007, vol. 332, pp. 185-191.

Sergio J. Garibay et al. "Isoreticular synthesis and modification of frameworks with the UiO-66 topology", Chem Commun (Camb), Nov. 7, 2010, vol. 46, No. 41, pp. 7700-7702.

Stefano Salmaso et al. "Cyclodextrin/PEG based hydrogels for multi-drug delivery", International Journal of Pharmaceutics, 2007, vol. 345, pp. 42-50.

Suzy Surble et al. "A new isoreticular class of metal-organic-frameworks with the MIL-88 topology" Chem. Commun. The Royal Society of Chemistry, 2006, pp. 284-286.

Suzy Surble et al. "Synthesis of MIL-102, a Chromium Carboxylate Metal-Organic Framework, with Gas Sorption Analysis", Journal of American Chemical Society, 2006, vol. 128, pp. 14889-14896.

T. Chalati et al. "Optimisation of the synthesis of MOF nanoparticles made of flexible porous iron fumarate MIL-88A", Journal of Materials Chemistry, 2011, vol. 21, pp. 2220-2227.

Tabatha R. Whitfield et al. "Metal-organic frameworks based on iron oxide octahedral chains connected by benzenedicarboxulate dianions", Solid State Sciences, 2005, vol. 7, pp. 1096-1103.

Thierry Loiseau et al. "Hydrothermal synthesis and crystal structure of a new three-dimensional aluminum-organic framework MIL-69 with 2, 6-naphthalenedicarboxylate (ndc), AL (OH)(ndc) H2O", C.R. Chimie 8, 2005, pp. 765-772.

Thomas Devic et al. "Functionalization in Flexible Porous Solids: Effects on the Pore Opening and the Host-Guest Interactions", J. Am. Chem. Soc., 2010, vol. 132, pp. 1127-1136.

Wei-Jern Tsai et al. "Selective COX-2 inhibitors. Part 1: Synthesis and biological evaluation of phenylazobenzenesulfonamides", Bioorganic & Medicinal Chemistry Letters, 2006, vol. 16, pp. 4440-4443.

Willem JM Mulder et al. "Magnetic and fluourescent nanoparticles for multimodality imaging", Future Medicine Ltd, Nanomedicine, 2007, vol. 2, No. 3, pp. 307-324.

Xin-Ming Liu et al. "Novel biomineral-binding cyclodextrins for controlled drug delivery in the oral cavity", Journal of Controlled Release, 2007, vol. 122, pp. 54-62.

Yan-Ping Ren et al. Nanoporous Lanthanide-Cooper(II) Coordination Polymers: Syntheses and Crystal Structures of [{M2(CU3(iminodiacetate)6)} 8H2)]n (M=La, Nd, Eu), Angew. Chem. Int. Ed., 2003, vol. 42, No. 5, p. 532.

Bei Liu et al. "Molecular simulation studies of separation of CH4/H2 mixture in metal-organic frameworks with interpenetration and mixed-ligand", Chemical Engineering Science, 2011, vol. 66, No. 13, pp. 3012-3019; XP002693314.

Christina A. Bauer et al. "Influence of Connectivity and Porosity on Ligand-Based Luminescence in Zinc Metal-Organic Frameworks", Journal of the American Chemical Society, Jan. 3, 2007, vol. 129, No. 22, pp. 7136-7144; XP002693319.

Hye Jeong Park et al. "Post-synthetic reversible incorporation of organic linkers into signle-crystal-to-single-crystal transformations and modification of gas sorption properties", Chemistry—A European Journal, 2010, vol. 16, No. 38, pp. 11662-11669; XP002693320.

International Search Report dated Aug. 2, 2013 re: Application No. PCT/FR2013/051219; 3 pp total.

(56) References Cited

OTHER PUBLICATIONS

Jiangpu Nan et al. "Formation mechanism of metal-organic framework membranes derived from reactive seeding approach", Microporous and Mesoporous Materials, 2012, vol. 155, pp. 90-98; XP002693321.

Jihyun An et al. "Cation-Triggered Drug Release from a Porous Zinc-Adeninate Metal-Organic Framework", Journal of the American Chemical Society, Apr. 14, 2009, vol. 131, No. 24, pp. 8376-8377; XP002693316.

Jong Sik Kim et al. "Method for supercritical treatment of porous metal organic framework", Chemical Abstracts Service, Database CA, XP002693322.

Marie Savonnet et al. "Combinatorial synthesis of metal-organic frameworks libraries by click-chemistry", New Journal of Chemistry, 2011, vol. 35, No. 9, pp. 1892-1897; XP002693315.

Sergey Sapchenko et al. "Microporous sensor: gas sorption, guest exchange and guest dependant luminescence of metal-organic framekwork", Dalton Transactions, 2011, vol. 40, No. 10, pp. 2196-2203; XP002693317.

Ugo Ravon et al. "Engineering of coordination polymers for shape selective alkylation of large aromatics and the role of defects" Microporous and Mesoporous Materials, 2010, vol. 129, No. 3, pp. 319-329; XP002693313.

Xiaoliang Zhao et al. "A porous metal-organic framework (MOF) with unusual 2D, fwdarw. 3D polycatenation based on honeycomb layers", Dalton Transactions, 2012, vol. 41, No. 7, pp. 1928-1930; XP002693318.

* cited by examiner

ALN = alendronate
PEG = poly(ethylene glycol)

ORGANIC-INORGANIC HYBRID SOLID HAVING A MODIFIED OUTER SURFACE

PRIORITY CLAIMED

The present application claims the priority of French patent application FR 12/55065 filed on May 31, 2012, the contents of which are incorporated herein by reference in their entirety.

DESCRIPTION

Field of Technology

The present invention relates to an improved porous crystalline metal-organic framework (MOF) solid having a modified outer surface, and notably to the method of preparation thereof.

The MOF solid of the present invention is usable for example as a contrast agent and/or for transporting pharmaceutical compounds. The solid of the present invention may also be used for applications in the area of storage, separation, catalysis, cosmetics or the food industry. It may also be used for vectoring and/or monitoring pharmaceutical compounds in an organism. It may also be used for detoxification. It may, for example, be in the form of crystals, powder, particles or nanoparticles.

The references in square brackets [X] refer to the list of references at the end of the examples.

Background

The use of transporters and carriers of molecules of interest, notably molecules with a therapeutic effect or markers, has become an important challenge for the development of new methods of diagnosis or new medicaments. In fact, the molecules of interest display characteristics that have an influence on the pharmacokinetics and biodistribution of these molecules and that are not always favorable or adaptable with respect to the environment into which they are introduced. These are, for example, physicochemical characteristics such as instability, a strong tendency to crystallization, low water/fat solubility and/or biological characteristics such as toxicity, biodegradability, etc.

It is in this context that novel nanocarriers were elaborated starting from very promising materials, never used previously in the biomedical area: porous crystalline organic-inorganic hybrid solids (cf. WO 2009/077670 [1] and WO 2009/077671 [2]).

Metal-organic frameworks (MOFs) are coordination polymers with a hybrid inorganic-organic framework comprising metal ions and organic ligands coordinated to the metal ions. These materials are organized in a one-, two- or three-dimensional network, where the inorganic entities are bound together periodically by spacer ligands. These materials have a crystalline structure, are generally porous and could be used in a great many industrial applications such as storage of gases, adsorption of liquids, separation of liquids or of gases, catalysis, etc.

Hybrid organic-inorganic nanoparticles (nanoMOFs) based on porous iron carboxylate were recently developed in order to meet certain challenges in modern galenical medicine. As noted previously, research in this area is part of the finding that there are a number of active ingredients with very short plasma half-life that are not readily able to overcome the body's natural barriers, or lead to phenomena of resistance or toxicity, for which nanoencapsulation would constitute an interesting alternative. Certain of these molecules of interest (notably with anticancer or antiviral activity) have not been encapsulated successfully in the known nanocarriers (liposomes, polymer-based or inorganic nanoparticles etc.). The main reason is due to the incompatibility of these active molecules, in terms of sufficient interaction in order to encapsulate them suitably, with the materials currently used for making the nanocarriers (polymers, lipids, oils, etc.).

NanoMOFS are for example formed from units of iron (III) that give rise, by bridging with endogenous or exogenous polycarboxylic acids, such as fumaric acid or trimesic acid, to large amphiphilic cages of a defined size (3 to 60 Å). It is possible to modulate the pore size, structure as well as the internal microenvironment (hydrophilic/hydrophobic balance) by varying the nature and functionalization of the carboxylic acids used during synthesis of the nanoMOFs.

Owing to their large pore volume and specific surface, these nanoparticles or nanoMOFs of iron carboxylate have proved capable of adsorbing, by simple impregnation in solutions of active ingredient, very large amounts of these therapeutic molecules, which may exceed 40 wt % in the case of several hydrophilic, hydrophobic or amphiphilic molecules, which had never been encapsulated effectively before (amounts encapsulated <1 or at best 5 wt %).

Degradability of these nanoMOFs in the body, as well as their biocompatibility, has been demonstrated. For example, injection of repeated doses of up to 220 mg/kg has shown no sign of toxicity in treated rats (behavior of the animals, weight, histology, alteration of biological markers). The ability of these nanoMOFS to produce a signal in vivo in magnetic resonance imaging (MRI) has also been demonstrated (labeling of the liver and spleen). The contrast was attributed both to the paramagnetic iron atoms and to the interconnected channels filled with water, coordinated to the metal sites and/or free sites. This observation has opened up attractive prospects in theranostics, allowing the fate of nanoparticles loaded with active ingredients to be monitored in vivo.

Reference may be made for example to international application WO 2009/077670 [1] for a description of these nanoparticles and their properties.

Methods for functionalization of the surface of nanoMOFs have been explored, so as to be able to control their interaction with the living environment and allow their selective addressing in vivo. This is important, since unmodified nanoparticles are quickly recognized as foreign bodies and are eliminated within a few minutes by the reticulo-endothelial system (accumulation in the liver and spleen). Other types of carriers (liposomes, nanoparticles, etc.) with a modified surface, developed some years ago, are capable of reaching biological targets.

International application WO 2009/077671 [2] describes methods for modifying the surface of nanoMOFs. For example, there it is proposed to couple linear polyethylene glycol (PEG) chains to the surface of the nanoMOFs in situ during synthesis thereof or post-synthesis in order to make the nanoMOFs "stealthy", i.e. capable of avoiding accumulation in the liver and spleen, and of altering their biodistribution.

However, this strategy of surface modification has some drawbacks, notably owing to the porous character of the MOF materials. These drawbacks are notably manifested in reduced capacity for encapsulation, and greater difficulty in controlling the release of the encapsulated active ingredients (cf. Example 11).

International application WO 2009/077671 [2] also describes the use of polymers bearing hydrophobic groups capable of interacting with the outer surface of the MOFs (such as dextran grafted with fluorescein and biotin groups) for covering (functionalizing) the surface of the MOFs. However, these methods of covering present problems of stability, notably in the physiological environment, which represents an obstacle to the use of these MOF materials having a modified outer surface for biomedical applications in vivo (cf. Example 12).

Therefore numerous improvements are still required in terms of functionalization of the outer surface of MOF particles. In particular, there is a real need for improved compounds capable of evading the immune system and/or rapid capture of them by certain organs, for example the liver, thus avoiding their accumulation in these organs, and capable of carrying active ingredients to specific targets.

DESCRIPTION OF THE INVENTION

The aim of the present invention is precisely to address these needs and drawbacks of the art by supplying a porous crystalline MOF solid having a modified outer surface comprising a three-dimensional sequence of units, which may be identical or different, having the following formula (I):

$$M_mO_kX_lL_p \qquad \text{Formula (I)}$$

wherein:
- each occurrence of M represents independently a metal ion selected from the group comprising $Fe^{2+}$, $Fe^{3+}$, $Zn^{2+}$, $Zr^{4+}$, $Ti^{4+}$, $Ca^{2+}$, $Mg^{2+}$ and $Al^{3+}$;
- m, k, l and p are numbers ≥0 selected so as to respect the charge neutrality of the unit; preferably, m, k, l and p are independently 0 to 4, for example m and p are independently 1, 2 or 3 and/or k and l are independently 0 or 1;
- X is a ligand selected from the group comprising $OH^-$, $Cl^-$, $F^-$, $I^-$, $Br^-$, $SO_4^{2-}$, $NO_3^-$, $ClO_4^-$, $R^1$—$(COO)_n^-$, $R^1$—$(SO_3)_n^-$, $R^1$—$(PO_3)_n^-$, wherein $R^1$ is a hydrogen, a linear or branched $C_1$ to $C_8$ alkyl, n=1 to 6; and
- L is a (polyfunctionalized) spacer ligand comprising a radical $R^0$ and q occurrences of a complexing group A, where
  q is an integer between 2 and 6;
  each occurrence of A is independently:
  (i) a carboxylate $$*\!-\!\overset{\overset{\#}{\overset{O}{\|}}}{C}\!-\!\overset{\#}{O};$$

(ii) a phosphonate $$*\!-\!\overset{\overset{\#}{\overset{O}{\|}}}{\underset{OR^{41}}{P}}\!-\!\overset{\#}{O};$$

or
  (iii) an imidazolate group $$\overset{*}{\underset{N}{\diagup}}\overset{\#}{\underset{N}{\diagdown}}\!R^{41};$$

wherein $R^{41}$ represents a hydrogen atom or a $C_{4-6}$alkyl radical;

wherein * denotes the point of attachment of group A to the radical $R^0$;
# denotes the possible points of attachment of group A to the metal ion M;
$R^0$ represents
- a $C_{1-12}$alkylene, $C_{2-12}$alkenylene or $C_{2-12}$alkynylene radical;
- a mono- or polycyclic aryl radical, fused or not, comprising from 6 to 50 carbon atoms,
- a mono- or polycyclic heteroaryl radical, fused or not, comprising from 4 to 50 carbon atoms,
- the radical $R^0$ optionally being substituted with one or more groups selected independently from the group halogen atom, OH, $NH_2$, $NO_2$ or a $C_1$ to $C_6$ alkyl;

wherein the outer surface of the MOF is modified in that it comprises at least one organic surface agent interacting with (for example complexed with) a metal center M or a ligand L located on the outer surface of the crystalline MOF solid.

Throughout the present description, as the variable q is at least 2, the ligand L is inherently polyfunctionalized.

Preferably the ligand L represents a di-, tri-, tetra- or hexa-carboxylate ligand.

Advantageously, the surface agent comprises: i) at least one phosphate, phosphonate, bisphosphonate, sulfate, carboxylate, hydroxy, cathecolate, thiolate (—SR or —$S^-$), N-containing heterocyclic, amido (—C(=O)N(R)$_2$), amino (—N(R)$_2$) group, or a combination of these groups, wherein each occurrence of R represents independently H, $C_{1-6}$alkyl or phenyl);

[Structures of Phosphate, Phosphonate, Bisphosphonate, Sulfate, Cathecolate]

wherein each occurrence of Q represents independently H or an alkali metal cation;
and/or ii) a rigid section larger than the size of the largest sized pore access windows of the MOF material (for example cyclodextrins).

The size of the pore access windows of the MOF materials described herein is defined by the parameters M, X, L, m, k, l and p. MOF materials are well known in the scientific literature, and the reader will be able without difficulty, based on the selection of the parameters M, X, L, m, k, l and p made (and therefore the choice of the MOF material in question), to determine the structure of the MOF, including the sizes of the pore windows, and in particular the size of the largest sized pore access windows of the MOF material.

Advantageously, when the rigid section of the surface agent is below the size of the largest sized pore access windows of the MOF material (and therefore when the surface agent is able, owing to its size and conformation, to penetrate into the pores of the MOF solid), the surface agent preferably has a plurality of phosphate, phosphonate, bisphosphonate, sulfate, carboxylate, hydroxy, cathecolate, thiolate (—SR or —S⁻), N-containing heterocyclic, amido (—C(=O)N(R)$_2$), amino (—N(R)$_2$) groups, or a combination of these groups, wherein each occurrence of R represents independently H, $C_{1-6}$alkyl or phenyl, distributed over the entire length of its main chain (for example dextran grafted with randomly distributed alendronates), thus avoiding considerable adsorption of the surface agent in the pores.

Advantageously, the organic surface agent may be selected from a cyclodextrin monomer, oligomer or polymer; a branched polyethylene glycol (e.g. "star" polymer or dendrimer); a protein; a polysaccharide, which may or may not bear a plurality of polyethylene glycol (PEG) side chains, which themselves optionally may or may not be coupled at the end of the chain with specific ligands; or a polysaccharide such as chitosan, water-insoluble at 6<pH<8 and water-soluble at pH<5.

Advantageously, said organic surface agent interacts with (for example is complexed with) a metal center M or with a ligand L located on the surface of the crystalline MOF solid via said one or more phosphate, phosphonate, sulfate, carboxylate, hydroxy, cathecolate, thiolate, nitrogen heterocyclic, amide or amino group(s), or a combination of these groups.

Advantageously, the PEG chains will be able to bear, at their end free, a specific ligand (antibody, peptide, folate etc.) allowing alteration of their biodistribution, notably targeting of the nanoparticles.

In the case of a polysaccharide bearing a plurality of polyethylene glycol side chains, the more PEG chains are grafted, the more the hydrophilicity of the copolymer increases. Thus, advantageously, it will be suitable in this case also to graft groups that are more complexing, such as alendronates, in order to ensure good stability of the covering.

Advantageously, the organic surface agent interacts with a metal center M or with a ligand L located on the surface of the crystalline MOF solid via at least one group among those mentioned above. The interaction preferably takes place by covalent, ionocovalent, ionic interactions or by weak interactions (i.e. hydrogen bonds) (for example iron-phosphate coordination). However, the interactions of the hydrophobic type (example: alkyl-MOF group) are preferably excluded, as they are too weak to ensure good stability of the covering.

"Good stability of the covering" refers to sufficient stability to make it possible, in a biological environment, to perform a function of biomedical interest: for example, to reach a target (ex tumor, infected tissue etc.); interact with the intestinal mucosa and/or circulate for a sufficient length of time in the bloodstream.

Advantageously, in in-vitro conditions, "good stability of the covering" may represent detachment of less than 20% of the covering (i.e. of the surface agent present on the outer surface of the MOF material) in one hour of incubation with stirring, at 37° C. in a 0.15 M phosphate buffer solution, pH 7.4.

Advantageously, when the rigid section of the surface agent is below the size of the largest sized pore access windows of the MOF material, the density of the anchorage points will preferably be able to be increased if one or more of the following criteria are fulfilled:
  groups possessing a lower capacity for interaction with the material (for example the carboxylate, amino or sulfate groups interact less strongly than the phosphates);
  high solubility of the surface agent in the dispersing medium;
  high flexibility of the surface agent and/or small rigid section.

For example, the surface agent may be dextran grafted both with PEG chains and alendronate bisphosphonate groups, as in the examples in the present application. The method of synthesis according to the present invention makes it possible to vary both the density of the PEG chains and of the anchorage points (alendronate).

Advantageously, the surface agents specifically described in application WO 2009/0077671 are excluded.

Advantageously, the organic surface agent may be selected from a cyclodextrin monomer, oligomer or polymer; a branched polyethylene glycol group; a polysaccharide bearing a plurality of polyethylene glycol side chains; or a polysaccharide that is water-insoluble at 6<pH<8 and water-soluble at pH<5.

In the context of the present invention, the various occurrences of M in the units of formula (I) may be identical or different. Preferably, each occurrence of M represents independently a metal ion $Fe^{2+}$, $Fe^{3+}$, $Zn^{2+}$ or $Ca^{2+}$.

"Solid" refers to, in the sense of the present invention, any type of crystalline material. Said solid may for example be in the form of crystals, powder, particles of various shapes, for example of spherical, cubic, parallelepipedal, rhombohedral, lamellar shape, etc. The particles may be in the form of nanoparticles.

"Nanoparticle" refers to a particle smaller than 1 μm. In particular, the nanoparticles of MOF solid according to the invention may have a diameter less than 1000 nanometers, preferably under 500 nm, more preferably under 250 nm, quite particularly under 100 nm.

"Rigid section" of a molecule or of a surface agent refers to the dimension of the minor axis of the rigid volume occupied by the molecule or surface agent in a given medium, advantageously a liquid medium. Advantageously, it may be the liquid medium wherein the molecule or surface agent is brought into contact with the MOF material, in particular during modification of the outer surface of the MOF material with the molecule or surface agent in question. Advantageously, it may also or alternatively be the liquid medium wherein the MOF material, modified with the molecule or surface agent according to the present invention, is located. Advantageously, the rigid volume represents the volume occupied by the molecule or surface agent in its most stable conformation in the medium in question, whether it be during modification of the outer surface of the MOF material according to the present invention, or once the surface modification has been carried out. In all cases, advantageously, the medium may be water, a physiological fluid, an organic solvent or a water/organic solvent mixture.

The rigid section may be calculated using numerical simulation (software: Materials Studio, Accelrys; known by a person skilled in the art) once the most stable conformation of the molecule or surface agent in the given medium is determined by minimization of energy. For example, the Accelrys software, Materials Studio version 5.0 (2010) may be used.

"Cyclodextrin monomer" refers to a cyclodextrin unit, which may be for example an α-, β- or γ-cyclodextrin.

"Cyclodextrin oligomer" refers to a chain of 2 to 9 identical or different cyclodextrin units. The cyclodextrin units may be for example α-, β- or γ-cyclodextrins.

"Cyclodextrin polymer" or "polycyclodextrin" refers to a polymer comprising at least 10 identical or different cyclodextrin units. Advantageously, the cyclodextrin polymer contains at least 10 cyclodextrin units, preferably at least 15 cyclodextrin units, and advantageously at least 20 cyclodextrin units. Particularly advantageously, it is preferred that the cyclodextrin polymers bearing cyclodextrins comprise on average at least 100 cyclodextrin units, preferably at least 200 cyclodextrin units, and advantageously at least 300 cyclodextrin units. Typically, the cyclodextrin polymers comprise on average at least 400 cyclodextrin units.

Advantageously, the polycyclodextrin contains on average between 10 and 1500 cyclodextrin units within its structure, preferably on average between 10 and 1000 cyclodextrin units, preferably on average between 15 and 800 cyclodextrin units, preferably on average between 50 and 600 cyclodextrin units, and advantageously on average between 100 and 400 cyclodextrin units.

The cyclodextrin units present within the polycyclodextrin may generally be α-cyclodextrins, β-cyclodextrins, γ-cyclodextrins, or else mixtures of at least two of these types of cyclodextrins.

The average number of cyclodextrin units present in the polymers of the invention may for example be established by size exclusion chromatography and by nuclear magnetic resonance.

Within the polycyclodextrins, the cyclodextrin units may be linked together by hydrocarbon chains with 3 to 50 carbon atoms, linear or branched, optionally interrupted by one or more oxygen atoms, and these chains preferably being alkyl, alkenyl, or alkynyl chains with 3 to 50 carbon atoms, or else polyether chains with 3 to 50 carbon atoms, and these chains may be substituted with hydrophilic groups (hydroxyl or amino groups for example). The chains linking the cyclodextrin units together may comprise at least 3 carbon atoms and preferably from 4 to 50 carbon atoms, the shortest path between two cyclodextrin units preferably consisting of a chain comprising between 3 and 8 carbon atoms.

Advantageously, the hydrocarbon chains linking two cyclodextrin units together within a polycyclodextrin correspond to the general formula—a group of formula —O—$(CH_2—CHOR^1—CH_2)_n$—O— wherein n is an integer between 1 and 50 (generally between 2 and 10) and where, in each of the n $(CH_2—CHOR^1—CH_2)$ units, $R^1$ denotes either a hydrogen atom, or a —$CH_2$—CHOH—$CH_2$—O— chain bound to a cyclodextrin unit of the polymer.

Thus, polycyclodextrins may typically be obtained by crosslinking cyclodextrin molecules with bifunctional compounds capable of forming covalent bonds with the hydroxyl groups of the cyclodextrins. For example, they may be dicarboxylic acids such as citric acid, sebacic acid, fumaric acid, glutamic acid, maleic acid, malic acid, malonic acid, aspartic acid, oxalic acid, succinic acid, glutaric acid, trans, trans-muconic acid, terephthalic acid, isophthalic acid, oxaloacetic acid, phthalic acid, adipic acid or butanedioic acid.

For example, polycyclodextrins may be obtained by polycondensation of molecules of cyclodextrins and of epichlorohydrin, generally in a basic medium (generally in an aqueous medium with addition of soda, at a concentration by weight from 10 to 40%), the cyclodextrins/epichlorohydrin molar ratio preferably being between 1:15 and 1:1, and advantageously between 1:15 and 1:8. For more details concerning this synthesis and control of the average number of cyclodextrin units integrated within the polymers based on cyclodextrin units obtained by this method, reference may notably be made to the following articles:

E. Renard et al., European Polymer Journal, Vol. 33, No. 1, pp 49-57 (1997) [6]

Gref et al., International Journal of Pharmaceutics, Vol. 332, Issues 1-2, Pages 185-191 (2007) [7]

Gref et al., J. Control Release, 111(3): 316-24 (2006) [8]

Gref et al., Journal of Colloid and Interface Science, 307(1): 83-93 (2007) [9]

Blanchemain et al., Acta Biomaterialia, Volume 4, Issue 6, Nov. 2008, Pages 1725-1733 [10]

Polycyclodextrins may also be obtained by polycondensation of molecules of cyclodextrins and of hexamethylene diisocyanate, as described for example in Elif Yilmaz Ozmen et al. *Bioresource Technology*, Volume 99, Issue 3, Pages 526-531 (2008) [11].

Polycyclodextrins may also be obtained by polycondensation of molecules of cyclodextrins and a functionalized polyethylene glycol, as described for example in:

Cesteros et al., *European Polymer Journal*, Volume 45, Issue 3, Pages 674-679 (2009) (acylated PEG) [12]

Salmaso et al., *International Journal of Pharmaceutics*, Volume 345, Issues 1-2, Pages 42-50 (2007) (diaminated PEG) [13]

Polycyclodextrins may also be obtained by polycondensation of molecules of cyclodextrins and several oligoethylimine branches, to form a star polymer, as described for example in Yang et al., *Biomaterials*, Volume 28, Issue 21, Pages 3245-3254 (2007) [14].

Regardless of the precise nature of the hydrocarbon chains linking the cyclodextrin units together, in general, the total weight of the cyclodextrin units present within the polycyclodextrins represents at least 30%, advantageously at least 40%, and even more preferably at least 50%, of the total weight of said polymers, this total weight of the cyclodextrin units generally representing between 30 and 80%, and preferably between 40 and 75% of the total weight of the polymers based on cyclodextrin units.

This percentage by weight of cyclodextrins in the polymers usable in the context of the present invention may for example be determined by nuclear magnetic resonance (NMR).

In certain embodiments, the polycyclodextrin may be a poly-β-cyclodextrin having the following Formula I:

Formula I

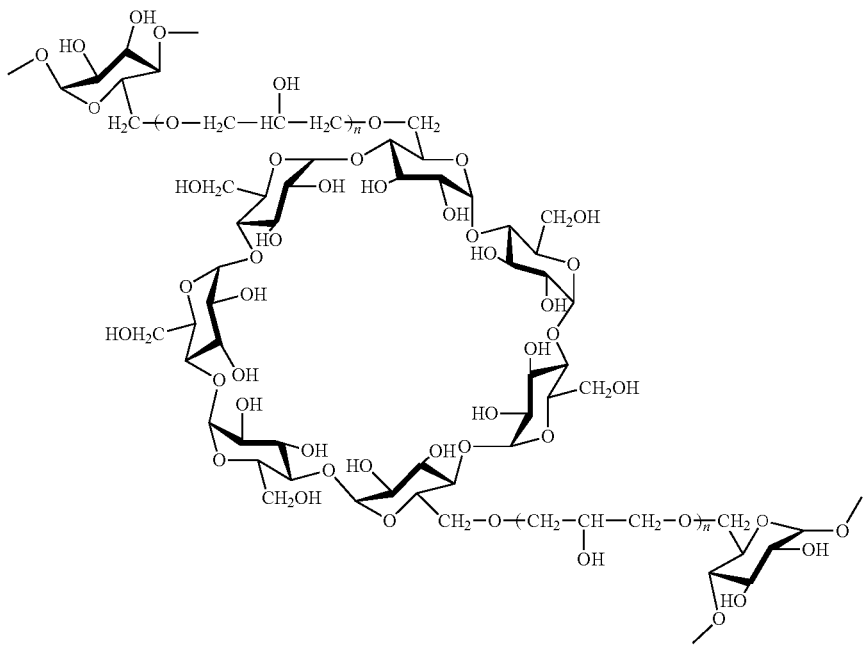

wherein n represents an integer between 1 and 50, preferably between 2 and 10; and the number of beta-cyclodextrin units is on average between 10 and 1500, preferably on average between 10 and 1000, preferably on average between 15 and 800, preferably on average between 50 and 600, and advantageously on average between 100 and 400 units.

In the above structure, the monosaccharides at the ends of the structure (i.e. with bonds shown with dotted lines) are a schematic representation of the continuity of the polymer (i.e. chaining of β-cyclodextrin units forming the rest of the polymer).

The polycyclodextrin may be a poly-β-cyclodextrin of higher molecular weight, and may correspond to formula I above, wherein n represents an integer between 1 and 50, preferably between 2 and 10; and the number of beta-cyclodextrin units is on average between 10 and 2000, preferably on average between 100 and 1800 units, preferably on average between 500 and 1600 units, and advantageously on average between 800 and 1500 units.

The polycyclodextrin may be a poly-α-cyclodextrin having

Formula I above wherein the α-cyclodextrin units are replaced by α-cyclodextrins.

The polycyclodextrin may be a poly-γ-cyclodextrin having Formula I above wherein the γ-cyclodextrin units are replaced by γ-cyclodextrins.

According to the invention, the branched polyethylene glycol group may be a polyethylene glycol dendrimer.

In the present text, the term "dendrimer" relates to a molecule whose architecture is reminiscent of that of the branches of a tree. It is a macromolecule of three-dimensional structure wherein the branched monomers are associated by an arborescent process around a multivalent central core. The dendrimers generally assume a very regular or spherical globular shape, highly branched and polyfunctionalized. They consist of three specific regions:

a multivalent central core, a defined number (constituting the multivalence) of intermediate dendritic branches connected to the multivalent central core where each dendritic branch consists of a certain generation number of branching, and the periphery consisting of a plurality of functional end groups.

These dendrimers have both internal cavities and a large number of easily accessible end groups at the periphery, which may be responsible for very varied properties and reactivities.

The dendrimers are constructed step by step in a succession of sequences, each leading to a new generation. Structural control is determining for the specific properties of these macromolecules. Methods of synthesis are known in the art. For example, we may mention:

Navath R S, Menjoge A R, Dai H, Romero R, Kannan S, Kannan R M., Injectable PAMAM dendrimer-PEG hydrogels for the treatment of genital infections: formulation and in vitro and in vivo evaluation, Mol Pharm. 2011 Aug. 1; 8(4): 1209-23 [34]. R C. Hedden and B. J. Bauer, Structure and Dimensions of PAMAM/PEG Dendrimer-Star Polymers, Macromolecules, 2003, 36 (6), pp 1829-1835 [35].

Certain of these PEG dendrimers are commercially available, for instance a branched PEG having one of the following structures:

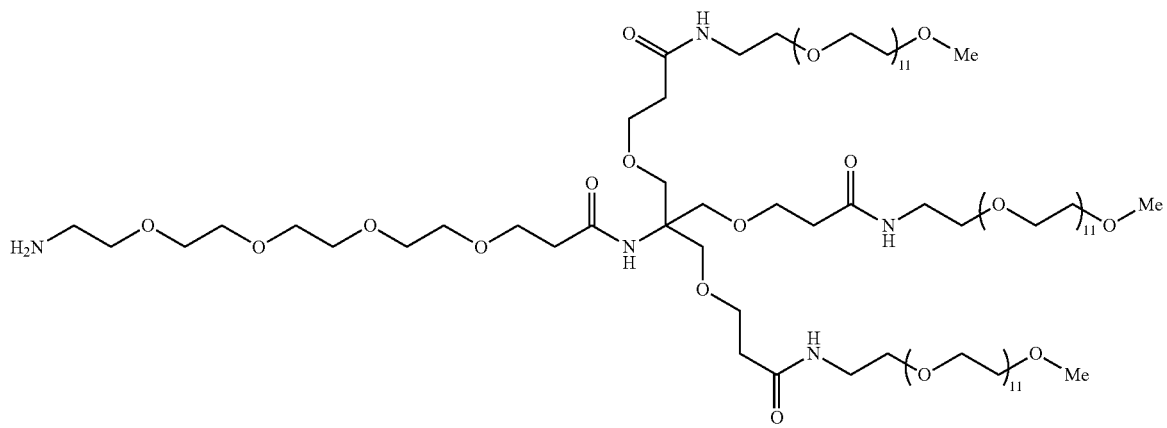

(H2N-dPEG(4)-[dPEG(12)-OMe]3 or C99H197N5O47 Iris Biotech, ref PEG1325.0100), or

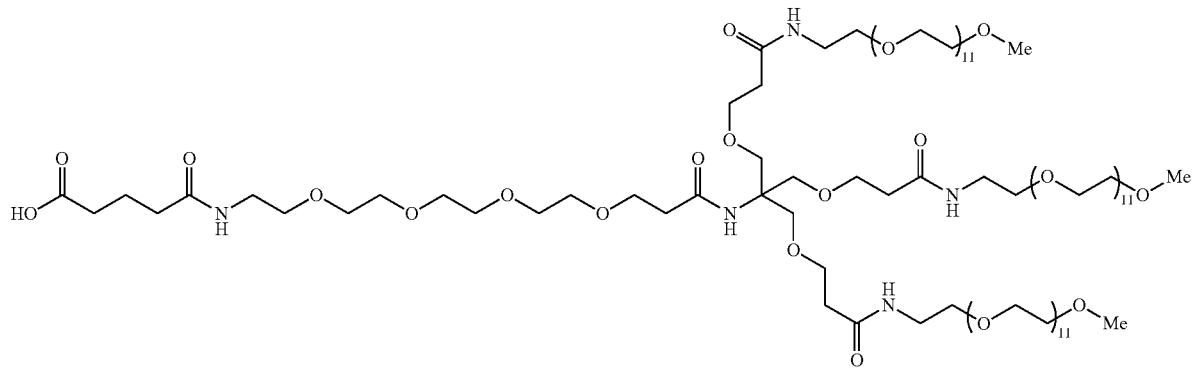

(HOOC-dPEG(4)-[dPEG(12)-OMe]3 or C104H203N5O50 Iris Biotech, ref PEG1490.0100).

There is also the PAMAM-PEG Dendrimer kit, generations 3-6 marketed by the company Sigma-Aldrich under reference 683493.

The surface agent may be a protein. In this case, several types of interactions may take place with the surface of the MOF by means both of $NH_2$ and COOH groups present on the protein, for example. The protein may be an enzymatic, structural, transport, signaling, regulatory or motor protein, such as albumin or the immunoglobulins.

In the present text, "polysaccharide bearing a plurality of polyethylene glycol side chains" refers to a polysaccharide on which polyethylene glycol groups are grafted. The polysaccharide may be a natural or a synthetic polysaccharide. For example, it may be hyaluronic acid, alginic acid, chitosan, chitin, scleroglucan, dextran, amylose, amylopectin, a cellulose derivative, starch, pullulan, pectin, an alginate, heparin, ulvan, a carrageenan, fucan, curdlan, xylan, polyguluronic acid, xanthan, arabinan, polysaccharides containing sialic acid or polymannuronic acid. Advantageously, the polysaccharide may be chitosan.

Methods for grafting polyethylene glycol groups to natural or synthetic polysaccharides are known. For example, a person skilled in the art could take inspiration from the methods described in:

N Bhattarai, H R. Ramay, J Gunn, F A. Matsen, M Zhan, PEG-grafted chitosan as an injectable thermosensitive hydrogel for sustained protein release, J Controlled Release, 103 (3), 609-624, 2005. [36] where more than 40 wt % of PEG was grafted to the chitosan.

J. A Wieland, T. L. Houchin-Ray, L. D. Shea, nonviral vector delivery from PEG-hyaluronic acid hydrogels, J. Controlled Release, 120 (3), 233-241, 2007. [37], in which, advantageously, star PEG (4 arms) bearing functionalities of the acrylic type was grafted to hyaluronic acid by photopolymerization.

According to the invention, the polysaccharide that is water-insoluble at 6<pH<8 and water-soluble at pH<5 may be chitosan. By varying the pH, the hydrodynamic diameter of the polysaccharide may be increased, which prevents it from penetrating into the pores of the MOF particles, and thus allows better control of the release profile of the compounds optionally encapsulated in the MOFs. Chitosan is water-soluble at low pH, but forms aggregates at neutral pH. Chitosan may therefore be used for covering, by a technique related to coacervation, the nanoMOFs of the present invention by varying the pH.

Phosphated cyclodextrins are known in the art. For example, we may mention the beta-cyclodextrin phosphate marketed by the company Cyclolab.

Sulfated cyclodextrins are known in the art. For example, we may mention the beta-cyclodextrin-sulfate marketed by the company Cyclolab.

Bisphosphonated cyclodextrins are known in the art. For example, reference may be made to the publication X. M.

Liu, H. Lee, R. Reinhardt, L. Marky, W Dong, J. Controlled Release Vol. 122, 2007, 54-62, Novel biomineral-binding cyclodextrins for controlled drug delivery in the oral cavity (beta-cyclodextrin-alendronate) [38].

The methods of synthesis for functionalizing the alpha and/or gamma-cyclodextrins with the phosphate, sulfate and bisphosphonate groups may be adapted from the methods of synthesis used for preparing their beta-cyclodextrin homologs cited above.

The biphosphonate group may be in the form of an alendronate or zoledronate group.

Advantageously, preference will be given to the strongest complexing groups of the metal sites, for example the phosphate, cathecolate, carboxylate, sulfate, phosphonate and/or biphosphonate groups.

The groups that are less complexing, such as hydroxy, thiolate, N-containing heterocyclic groups, amido or amino, may also be used. In this case, an organic surface agent will preferably be used, as defined above, functionalized with several amino groups, in order to compensate the low complexing power of the latter.

It should be noted that the COOH or $NH_2$ groups present on the proteins for example, may also contribute to anchoring of the protein (as surface agent) on the surface of the MOFs.

In general, the term "substituted", whether or not preceded by the term "optionally", and the substituents described in the formulas of the present application, denote replacement of a hydrogen atom in a given structure with the radical of a specified substituent. The term "substituted" denotes for example replacement of a hydrogen atom in a given structure with a radical $R^2$ as defined above. When more than one position can be substituted, the substituents may be the same or different at each position.

"Spacer ligand" refers to, in the sense of the present invention, a ligand (including for example the neutral species and the ions) coordinated to at least two metal sites M, contributing to the spacing between these metal sites and to the formation of empty spaces or pores. The spacer ligand may comprise several complexing groups comprising carboxylates, phosphonates, imidazolates, preferably with from 2 to 6 functional groups which may be mono-, bi-, tri- or tetradentate, i.e. may comprise 1, 2, 3 or 4 points of attachment to the metal site.

"Outer surface" refers to, in the sense of the present invention, the outer surface of the MOF materials, i.e. excluding the surface of the pores (micropores and/or mesopores) of the MOFs.

"Alkyl" refers to, in the sense of the present invention, a linear, branched or cyclic carbon-containing radical, saturated or unsaturated, optionally substituted, comprising 1 to 25 carbon atoms, for example 1 to 10 carbon atoms, for example 1 to 8 carbon atoms, for example 1 to 6 carbon atoms.

"Alkylene" refers to, in the sense of the present invention, a linear, branched or cyclic divalent carbon-containing radical, saturated, optionally substituted, comprising 1 to 25 carbon atoms, for example 1 to 10 carbon atoms, for example 1 to 8 carbon atoms, for example 1 to 6 carbon atoms.

"Alkenylene" refers to, in the sense of the present invention, an alkylene radical, as defined above, having at least one carbon-carbon double bond.

"Alkynylene" refers to, in the sense of the present invention, an alkylene radical, as defined above, having at least one carbon-carbon triple bond.

"Aryl" refers to, in the sense of the present invention, an aromatic system comprising at least one ring satisfying Hückel's aromaticity rule. Said aryl is optionally substituted and may comprise from 6 to 50 carbon atoms, for example 6 to 20 carbon atoms, for example 6 to 10 carbon atoms.

"Heteroaryl" refers to, in the sense of the present invention, a system comprising at least one aromatic ring with 5 to 50 ring members, among which at least one group of the aromatic ring is a heteroatom, notably selected from the group comprising sulfur, oxygen, nitrogen, boron. Said heteroaryl is optionally substituted and may comprise from 1 to 50 carbon atoms, preferably 1 to 20 carbon atoms, preferably 3 to 10 carbon atoms.

"Amino" refers to, in the sense of the present invention, a system of formula —$N(R)_2$ wherein each occurrence of R represents independently H, $C_{1-6}$alkyl, or $C_{6-10}$aryl, preferably H, $C_{1-6}$alkyl, or phenyl.

"Amido" refers to, in the sense of the present invention, a system of formula —$C(=O)N(R)_2$ wherein each occurrence of R represents independently H, $C_{1-6}$alkyl, or $C_{6-10}$aryl, preferably H, $C_{1-6}$alkyl, or phenyl.

"N-containing heterocyclic" refers to, in the sense of the present invention, a mono- or polycyclic cyclic system, saturated or unsaturated and nonaromatic, comprising from 5 to 20 ring members, and optionally comprising one or more cycles with 5 or 6 ring members having at least one nitrogen atom, and optionally between 1 and 2 other heteroatoms selected independently of one another from S, O, and N, wherein (i) each ring with 5 ring members has from 0 to 2 double bonds, and each ring with 6 ring members has from 0 to 3 double bonds, (ii) the sulfur and/or nitrogen atoms are optionally oxidized, and (iii) the nitrogen atoms are optionally in the form of a quaternary salt. For example, a heterocyclic radical may be a pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, or tetrahydrofuryl group.

"Three-dimensional structure" refers to a three-dimensional succession or repetition of units of formula (I) as is understood conventionally in the field of MOF materials, which are also characterized as "metal-organic coordination polymers".

Unless stated otherwise, the various embodiments that follow relating to MOF materials apply as much to their uses as to their method of preparation according to the present invention.

"Surface agent" refers to, according to the invention, a molecule covering, partly or wholly, the surface of the solid allowing the surface properties of the material to be modulated, for example:
  modify its biodistribution, for example to avoid recognition by the reticulo-endothelial system ("stealth properties"), and/or
  endow it with interesting properties of bioadhesion for administration by oral, ocular, nasal, and/or rectal routes
  to allow it specific targeting of certain diseased organs/tissues, etc.

According to the invention, several surface agents may be used for combining the aforementioned properties.

According to the invention, a surface agent combining at least two of the aforementioned properties may be used.

According to the invention, the organic surface agent may be selected for example from the group comprising:
  α-, β- or γ-cyclodextrins;
  oligomers of α-, β- or γ-cyclodextrins;
  poly-α, poly-β or poly-γ-cyclodextrins, copolymers of α-, β- and/or γ-cyclodextrins,
PEG dendrimers,
chitosan,
chitosan bearing a plurality of PEG side chains,
albumin, immunoglobulins, etc.,
said surface agent comprising one or more phosphate, phosphonate, bisphosphonate, sulfate, carboxylate, hydroxy, cathecolate, thiolate, N-containing heterocyclic (for example azolate, imidazolate), amido or amino group(s).

According to the invention, the cyclodextrin units of poly-α, poly-β or poly-γ-cyclodextrin or the copolymer of α, β and/or γ-cyclodextrin may be linked together by hydrocarbon chains having the formula —O—(CH$_2$—CHOR$^1$—CH$_2$)$_n$—O— wherein n is an integer between 1 and 50 and, in each of the (CH$_2$—CHOR$^1$—CH$_2$) units, R$^1$ denotes either a hydrogen atom, or a —CH$_2$—CHOH—CH$_2$—O— chain bound to a cyclodextrin unit of said polymer or copolymer.

According to the invention, the poly-α, poly-β or poly-γ-cyclodextrin or the copolymer of α, β and/or γ-cyclodextrin may be obtained by polycondensation of molecules of cyclodextrin and epichlorohydrin.

The MOF solid according to the invention may comprise atoms of di-, tri- or tetravalent metals. The metal atoms may have an octahedral, pentahedral, tetrahedral geometry, or may have a higher coordination number in the structure of the material.

"Coordinence" or "coordination number" refers to the number of bonds for which the two electrons shared in the bond are derived from the same atom. The electron-donating atom acquires a positive charge whereas the electron-accepting atom acquires a negative charge.

Moreover, the metal atoms may be isolated or grouped together in inorganic entities. The MOF solid according to the invention may for example be constructed from chains of polyhedrons, of dimers, trimers, tetramers, pentamers or hexamers of polyhedrons or of a combination of these entities. For example, the MOF solid according to the invention may be constructed from chains of octahedra, of dimers, trimers or tetramers of octahedra. For example, the iron carboxylate MOF materials according to the invention may be constructed from chains of octahedra bound by the vertices or the edges or from trimers of octahedra connected by a central oxygen atom.

"Inorganic entity" refers to, in the sense of the present invention, an ensemble of atoms containing at least two metals bound by ionocovalent bonds, or directly by anions, for example O, OH, Cl, F, etc., or by the organic ligand.

Moreover, the MOF solid according to the invention may be in different forms or "phases" taking into account the various possibilities of organization and of connections of the ligands to the metal or to the metal group.

"Phase" refers to, in the sense of the present invention, a hybrid composition comprising at least one metal and at least one organic ligand possessing a defined crystalline structure.

The crystalline spatial organization of the solid of the present invention is based on the particular characteristics and properties of this material, and notably governs the pore size, which has an influence on the specific surface of the material and on the characteristics of adsorption, but also the density of the material, the latter being relatively low, the proportion of metal in this material, the stability of the material, the rigidity and flexibility of its structure, etc.

In particular, the MOF solid according to the invention may be isoreticular, i.e. comprise frameworks with the same topology.

Moreover, the solid of the present invention may comprise units that contain either a single type of metal ion, or several types of metal ions.

For example, the solid of the present invention may comprise a three-dimensional sequence of three different units. For example, the solid of the present invention may also comprise a three-dimensional sequence of two different units.

Moreover, the pore size may be adjusted by choosing appropriate spacer ligands.

Advantageously, ligand L of the unit of formula (I) of the MOF solid of the present invention may be a ligand bearing several complexing groups comprising the carboxylates, phosphonates, imidazolates; preferably the carboxylate group is a di-, tri-, tetra- or hexacarboxylate selected from the group comprising:

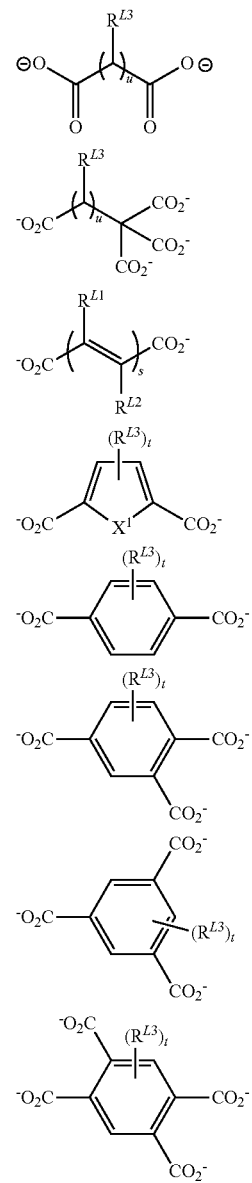

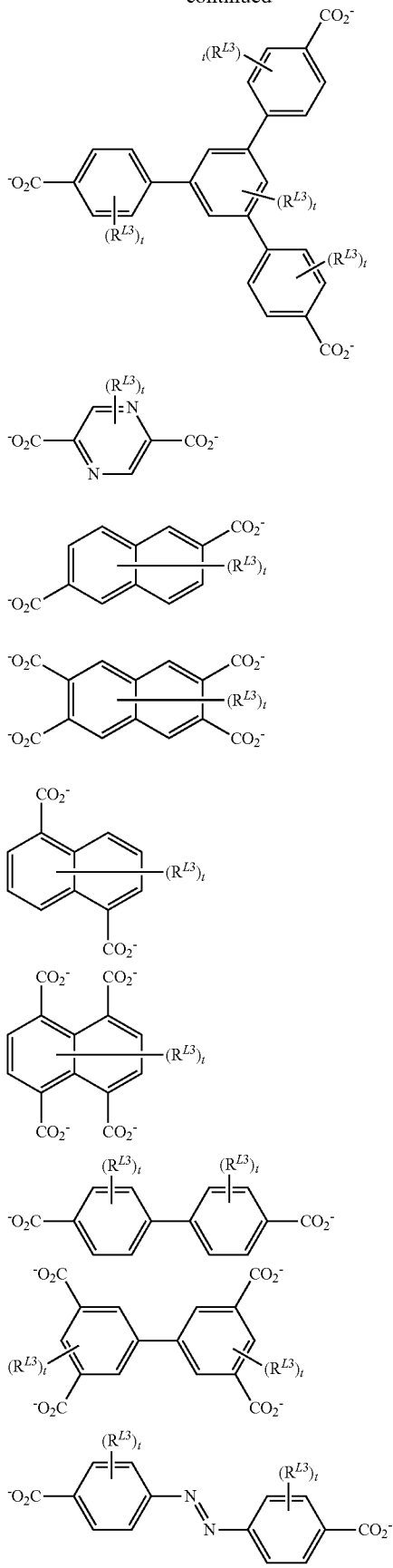
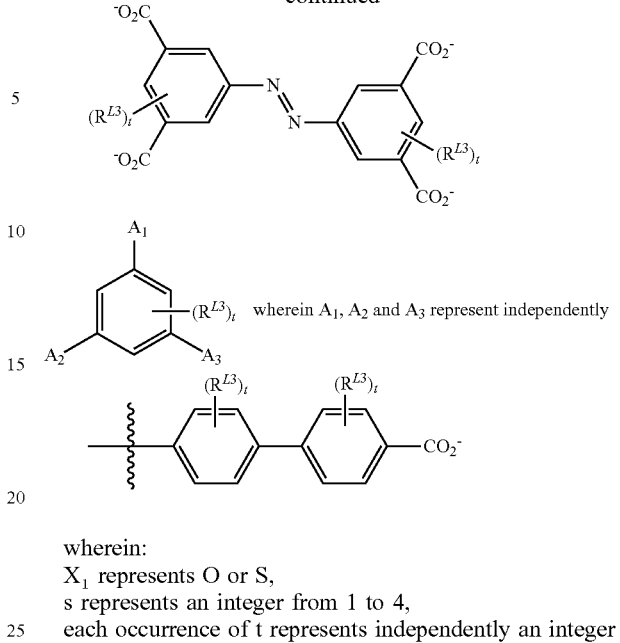

wherein:
X$_1$ represents O or S,
s represents an integer from 1 to 4,
each occurrence of t represents independently an integer from 1 to 4,
u represents an integer from 1 to 7,
R$^{L1}$ and R$^{L2}$ represent independently H, a halogen atom or a C$_1$ to C$_6$ alkyl (preferably methyl or ethyl), and
each occurrence of R$^{L3}$ represents independently H, a halogen atom (preferably F, Cl or Br), OH, NH$_2$, NO$_2$ or a C$_1$ to C$_6$ alkyl (preferably methyl or ethyl).

In particular, ligand L of the unit of formula (I) of the present invention may be a di-, tri- or tetracarboxylate ligand selected from the group comprising: C$_2$H$_2$(CO$_2^-$)$_2$ (fumarate), C$_2$H$_4$(CO$_2^-$)$_2$ (succinate), C$_3$H$_6$(CO$_2^-$)$_2$ (glutarate), C$_4$H$_4$(CO$_2^-$)$_2$ (muconate), C$_4$H$_8$(CO$_2^-$)$_2$ (adipate), C$_7$H$_{14}$(CO$_2^-$)$_2$ (azelate), C$_5$H$_3$S(CO$_2^-$)$_2$ (2,5-thiophenedicarboxylate), C$_6$H$_4$(CO$_2^-$)$_2$ (terephthalate), C$_6$H$_2$N$_2$(CO$_2^-$)$_2$ (2,5-pyrazine dicarboxylate), C$_{10}$H$_6$(CO$_2^-$)$_2$ (naphthalene-2,6-dicarboxylate), C$_{12}$H$_8$(CO$_2^-$)$_2$ (biphenyl-4,4'-dicarboxylate), C$_{12}$H$_8$N$_2$(CO$_2^-$)$_2$ (azobenzenedicarboxylate), C$_6$H$_3$(CO$_2^-$)$_3$ (benzene-1,2,4-tricarboxylate), C$_6$H$_3$(CO$_2^-$)$_3$ (benzene-1,3,5-tricarboxylate), C$_{24}$H$_{15}$(CO$_2^-$)$_3$ (benzene-1,3,5-tribenzoate), C$_6$H$_2$(CO$_2^-$)$_4$ (benzene-1,2,4,5-tetracarboxylate, C$_{10}$H$_4$(CO$_2^-$)$_4$ (naphthalene-2,3,6,7-tetracarboxylate), C$_{10}$H$_4$(CO$_2^-$)$_4$ (naphthalene-1,4,5,8-tetracarboxylate), C$_{12}$H$_6$(CO$_2^-$)$_4$ (biphenyl-3,5,3',5'-tetracarboxylate), and the modified analogs selected from the group comprising 2-aminoterephthalate, 2-nitroterephthalate, 2-methylterephthalate, 2-chloroterephthalate, 2-bromoterephthalate, 2,5-dihydroxoterephthalate, tetrafluoroterephthalate, tetramethylterephthalate, dimethyl-4,4'-biphenyldicarboxylate, tetramethyl-4,4'-biphenyldicarboxylate, dicarboxy-4,4'-biphenyldicarboxylate, 2,5-pyrazyne dicarboxylate. Ligand L of the unit of formula (I) of the present invention may also represent 2,5-diperfluoroterephthalate, azobenzene-4,4'-dicarboxylate, 3,3'-dichloro azobenzene-4,4'-dicarboxylate, 3,3'-dihydroxo azobenzene-4,4'-dicarboxylate, 3,3'-diperfluoro-azobenzene-4,4'-dicarboxylate, 3,5,3',5'-azobenzene tetracarboxylate, 2,5-dimethylterephthalate, perfluorosuccinate, perfluoromuconate, perfluoroglutarate, 3,5,3',5' perfluoro-4,4'-azobenzene dicarboxylate, 3,3'-diperfluoro-azobenzene-4,4'-dicarboxylate.

Advantageously, ligand L of the unit of formula (I) of the present invention may also be an imidazolate, tetrazolate, phosphate or phosphonate ligand such as imidazole, 2-methylimidazolate, 2-ethylimidazole, 4-(-imidazole-dicarboxylic acid, 1,4-(butanediyl)bis(imidazole), purine, pyrimidine, benzimidazolate, piperazinediphosphonate, tetrazolylbenzoate.

Most of the ligands listed above are commercially available. The reader may refer to the Examples section and/or to international applications WO 2009/077670 and WO 2009/077671 for preparing the ligands that are not commercially available.

Ligand L may display biological activity. The nanoporous hybrid solids according to the invention possess a mineral part, the metal (iron), and an organic part, a ligand with two or more complexing groups (carboxylate, phosphate, amide, etc.). The incorporation of organic ligands that possess biological activity has the advantage of allowing controlled release of active molecules as a function of the rate of degradation of the material (in relation to the aforementioned biologically active ligands, which are released during degradation of the MOF material). Thus, the MOF material itself may be "bioactive", i.e. it is able to release components having biological activity.

Moreover, release of these active molecules that form part of the MOF framework may be combined with the release of other active ingredients encapsulated in the MOF solids according to the invention. This aspect of encapsulation of active ingredients is described below in the present document.

Thus, the present invention also relates to MOF solids comprising biologically active ligands and/or encapsulating one or more active ingredients, with an activity perhaps complementary or different, and use thereof for combination therapies. The combination therapy is implemented by release (i) of the active ingredient encapsulated in the pores of the MOF material and (ii) of the biologically active ligands incorporated in the network (framework) of the crystalline MOF material.

There are numerous biologically active organic molecules comprising complexing groups, able to form porous hybrid solids according to the present invention.

For example, these may be azelaic acid ($HO_2C(CH_2)_7CO_2H$, a dermatologic agent with antineoplastic activity), meprobamate (anticonvulsant, sedative, muscle relaxant, antianxiety), aminosalicylic acid (antituberculosis), clodronate, pamidronate, zoledronate, alendronate and etidronate (therapeutic treatment for postmenopausal osteoporosis), azobenzenes (antimicrobial activity, COX inhibitors), porphyrins or amino acids (Lys, Arg, Asp, Cys, Glu, Gln, etc.), 4-aminosalycic acid, pyrazinamide (antituberculous), dibenzofuran-4,6-dicarboxylic acid (transthryretin inhibitor), dipicolinic acid (inhibitor of dihydrodipicolinate reductase), glutamic acid, fumaric acid, succinic acid, suberic acid, adipic acid, nicotinic acid, nicotinamide, purines, pyrimidines, etc.

We may mention, for example, the antimicrobial or anti-inflammatory activity (NSAIDs, COX inhibitors) of the azobenzenes. In this connection, the reader may refer to the following references: G. Oros, T. Cserhati, E. Forgacs, *Chemosphere* 52, 2003, 185 [15], A. M. Badawi, E. M. S. Azzam, S. M. I. Morsy, *Bioorg. Med. Chem.*, 14, 2006, 8661 [16] and W-J. Tsai, Y-J Shiao, S-J Lin, W-F Chiou, L-C Lin, T-H Yang, C-M Teng, T-S Wu, L-M Yang, *Bioorg. Med. Chem. Letters* 16, 2006, 4440 [17].

Thus, ligand L may be a biologically active ligand selected from the group comprising $C_7H_{14}(CO_2^-)_2$ (azelate); aminosalicylate (carboxyl, amino and hydroxo groups); clodronate, pamidronate, alendronate and etidronate (comprising phosphonate groups); meprobamate (comprising carbamate groups); porphyrins comprising carboxylate, phosphonate and/or amino groups; amino acids (Lys, Arg, Asp, Cys, Glu, Gln, etc.) that comprise amino, carboxylate, amide and/or imine groups; azobenzenes comprising carboxylate, phosphonate, and/or amino groups; dibenzofuran-4,6-dicarboxylate, dipicolinate (mixed ligand of the pyridine type with carboxyl groups); glutamate, fumarate, succinate, suberate, adipate, nicotinate, nicotinamide, purines, pyrimidines, etc.

Anion X of the unit of formula (I) of the present invention may be selected from the group comprising $OH^-$, $Cl^-$, $Br^-$, $F^-$, $R-(COO)_n^-$, $PF_6^-$, $NO_3^-$, $SO_4^{2-}$, $ClO_4^-$, with R and n as defined above.

In particular, anion X of the unit of formula (I) of the present invention may be selected from the group comprising $OH^-$, $Cl^-$, $F^-$, $CH_3-COO^-$, $PF_6^-$, $ClO_4^-$, or else a ligand selected from the above list.

Advantageously, anion X may be selected from the group comprising $OH^-$, $Cl^-$, $F^-$ and $R-(COO)_n^-$ wherein R represents $-CH_3$, $-C_6H_3$, $-C_6H_4$, $-C_{10}H_4$ or $-C_6(CH_3)_4$.

In one embodiment, anion X may be in an isotopic form suitable for imaging techniques such as positron emission tomography (PET).

Positron emission tomography (PET) is a method of nuclear medical imaging that makes it possible to measure the metabolic activity of an organ in three dimensions owing to the emissions produced by the positrons from disintegration of a radioactive product injected beforehand. PET is based on the general principle of scintigraphy, which consists of injecting a tracer with known behavior and biological properties, to obtain an image of the functioning of an organ. This tracer is labeled with a radioactive atom (carbon, fluorine, nitrogen, oxygen, etc.) that emits positrons, whose annihilation itself produces two photons. Detection of the trajectory of these photons by the collimator of the PET camera makes it possible to locate the place of their emission and therefore the concentration of the tracer at each point of the organ. It is this quantitative information that is represented in the form of an image, with coloring of the zones with high concentration of the tracer.

Thus, PET makes it possible to visualize the metabolic activities of the cells: it is called functional imaging, as opposed to the techniques of so-called structural imaging such as those based on X-rays (radiology or CT scan) which is limited to the images of the anatomy. Consequently, positron emission tomography is a diagnostic tool that makes it possible to detect certain disorders that are reflected in a change in the normal physiology, such as cancers. PET is also used in biomedical research, for example in brain imaging, where it makes it possible to reveal the active regions of the brain during a particular cognitive activity, similarly to what takes place in functional magnetic resonance imaging.

For example, X may represent $^{18}F^-$, which is a positron emitter and therefore allows the use of the MOF solids of the invention for applications involving PET imaging.

Thus, in one embodiment, in the unit of formula (I), at least one occurrence of ligand X is $^{18}F^-$.

The MOF solid according to the invention may comprise a percentage of metal in the dry phase from 5 to 40%, preferably from 18 to 31%.

Percentage by weight (wt %) is a unit of measurement used in chemistry and in metallurgy for denoting the composition of a mixture or of an alloy, i.e. the proportions of each component in the mixture.

1 wt % of a component=1 g of the component per 100 g of mixture, or 1 kg of said component per 100 kg of mixture.

The MOF solids of the present invention notably have the advantage of possessing thermal stability up to a temperature of 400° C.

In particular, the MOF solid of the present invention notably has the advantage of having thermal stability from 120° C. to 400° C.

In particular, the MOF solid according to the invention may be in particulate form with a particle diameter under 4 µm, preferably under 1000 nanometers.

In particular, the MOF solid according to the invention may have a pore size from 0.4 to 6 nm, preferably from 0.5 to 5.2 nm, and more preferably from 0.5 to 3.4 nm.

In particular, the MOF solid according to the invention may have a specific surface (BET) from 5 to 6000 $m^2/g$, preferably from 5 to 4500 $m^2/g$.

In particular, the MOF solid according to the invention may have a pore volume from 0.05 to 4 $cm^2/g$, preferably from 0.05 to 2 $cm^2/g$.

In the context of the invention, pore volume signifies the volume accessible for the molecules of gas and/or of liquid.

The inventors have demonstrated that the MOF materials comprising a three-dimensional structure of units of formula (I) may be in the form of a rigid or flexible structure.

The MOF solid of the present invention may be in the form of a robust structure, which has a rigid framework and undergoes only very slight shrinkage when the pores are emptied, or in the form of a flexible structure, which may swell and contract, varying the opening of the pores as a function of the nature of the molecules adsorbed.

These adsorbed molecules may be, for example, solvents and/or gases.

"Rigid structure" refers to, in the sense of the present invention, structures that swell or contract only very slightly, i.e. with an amplitude of up to 10%.

In particular, the MOF solid according to the invention may have a rigid structure that swells or contracts with an amplitude from 0 to 10%.

"Flexible structure" refers to, in the sense of the present invention, structures that swell or contract with a large amplitude, notably with an amplitude above 10%, for example above 50%.

In particular, a MOF material of flexible structure may swell or contract with an amplitude from 10% to 300%, preferably from 50 to 300%.

In particular, the MOF solid according to the invention may have a flexible structure that swells or contracts with an amplitude above 10%, for example from 50 to 300%.

The present invention may be implemented with MOF materials of rigid or flexible structure.

The properties of these MOF solids are described for example in international applications WO 2009/77670 and WO 2009/77671.

Various MOF materials have been developed by the inventors at the Lavoisier Institute in Versailles with various phases, called "MIL" (for "Material Institute Lavoisier"). The designation "MIL" of these structures is followed by an arbitrary number n given by the inventors for identifying the different phases.

In the present document, the acronym "ZIF" is the abbreviation for the English term "Zeolite Imidazolate Framework".

In the present document, the acronym "UiO" is the abbreviation for the English term "University of Oslo".

In the present document, the acronym "AEPF" is the abbreviation for the English term "alkaline-earth polymer framework".

The inventors have also demonstrated that certain solids according to the invention may have a larger number of possible phases relative to the MOF materials classically encountered in the literature. For example, various phases have been obtained for the iron(III) carboxylate solids according to the invention, for example MIL-53, MIL-69, MIL-88A, MIL-88B, MIL-88Bt, MIL-88C, MIL-88D, MIL-89, MIL-100, MIL-101, MIL-102. These various phases are presented inter alia in international applications WO 2009/77670 and WO 2009/77671.

The crystallographic characteristics of these structures are known, and have been the subject of numerous reports. The same applies to description and calculation of the largest sized pore access windows of the MOF materials described in the present document (the reader will be able to find this information in the publications cited in the present document for each specific type of MOF mentioned). Moreover, the aforementioned "MIL" designations are well known by a person skilled in the art. We may mention for example:

MIL-53: Whitfield, T. R.; Wang, X.; Liu, L.; Jacobson, A. J. Solid State Sci. 2005, 7, 1096. [18];

MIL-69: T. Loiseau et al., C. R. Chimie, 8 765 (2005). [19]

MIL-88A: (a) Serre et al., "Role of solvent-host interactions that lead to very large swelling of hybrid frameworks", Science, 2007, Vol. 315, 1828-1831 [20]; (b) Surblé et al., "A new isoreticular class of metal-organic frameworks with the MIL-88 topology", Chem. Comm., 2006, 284-286 [21]; (c) Mellot-Draznieks et al., "Very large swelling in hybrid frameworks: a combined computational and powder diffraction study", J. Am. Chem. Soc., 2005, Vol. 127, 16273-16278 [22]; Chalati et al., "Optimization of the synthesis of MOF nanoparticles made of flexible porous iron fumarate MIL-88A", J. Mater. Chem., 2011, 21, 2220 [39].

MIL-88B, MIL-88C and MIL-88D: For these structural types, the reader may refer to the publications concerning type MIL-88A above, namely, (a) Serre et al., "Role of solvent-host interactions that lead to very large swelling of hybrid frameworks", Science, 2007, Vol. 315, 1828-1831 [20]; (b) Surblé et al., "A new isoreticular class of metal-organic frameworks with the MIL-88 topology", Chem. Comm., 2006, 284-286 [21].

MIL-89: C. Serre, F. Millange, S. Surblé, G. Férey Angew. Chem. Int. Ed. 2004, 43, 6286: A new route to the synthesis of trivalent transition metals porous carboxylates with trimeric SBU. [23]

MIL-100: Horcajada et al., "Synthesis and catalytic properties of MIL-100(Fe), an iron(III) carboxylate with large pores", Chem. Comm., 2007, 2820-2822. [24]

MIL-101: Férey et al., "A chromium terephthalate-based solid with unusually large pore volumes and surface area", Science, 2005, Vol. 309, 2040-2042. [25]

MIL-102: S. Surblé, F. Millange, C. Serre, T. Düren, M. Latroche, S. Bourrelly, P. L. Llewellyn and G. Férey "MIL-102: A Chromium Carboxylate Metal Organic Framework with Gas Sorption Analysis" J. Am. Chem. Soc. 128 (2006), 46, 14890.

UiO-66: For this structural type, the reader may refer to the publications: (a) Cavka, J.; Jakobsen, S.; Olsbye, U.; Guillou, N.; Lamberti, C.; Bordiga, S.; Lillerud, K., J. Am. Chem. Soc. 2008, 130, 13850 [40]. (b) Kandiah, M.; Nilsen, M. H.; Usseglio, S.; Jakobsen, S.; Olsbye, U.; Tilset, M.; Larabi, C.; Quadreli, E. A.; Bonino, F.; Lillerud K. P., *Chem. Mater.*, 2010, 22(24), 6632 [41]. (c) Garibay S. J.; Cohen S. M., *Chem. Commun.*, 2010, 46, 7700 [42]

ZIF-8: For this structural type, the reader may refer to Park et al., "Exceptional chemical and thermal stability of zeolitic imidazolate frameworks", Proc. Natl. Acad. Sci. U.S.A., 2006, 103, 10186 [43]

MIL-125(Ti) and MIL-125(Ti)_$NH_2$. For this structural type, the reader may refer to the following publications: (a) M. Dan-Hardi, C. Serre, T. Frot, L. Rozes, G. Maurin, C. Sanchez and G. Férey: *J. Am. Chem. Soc.* Comm., 131, 2009, 10857-10859 A New Photoactive Crystalline Highly Porous Titanium (IV) Dicarboxylate [44]; (b) C. Zlotea, D. Phanon, M. Mazaj, D. Heurtaux, V. Guillerm, C. Serre, P. Horcajada, T. Devic, E. Magnier, F. Cuevas, G. Férey, P. L. Llewellyn and M. Latroche: "Effect of $NH_2$ and $CF_3$ functionalization on the hydrogen sorption properties of MOFs" *Dalton Trans.*, 2011, 40, 4879-4881 [45]

AEPF-1(Ca) and other calcium-based MOFs: AEPF=alkaline-earth polymer framework For this structural type, the reader may refer to the publications A. E. Platero-Prats, V. A. de la Pena-O'Shea, N. Snejko, A. Monge, E. Gutierrez-Puebla, "Dynamic calcium metal-organic framework acts as a selective organic solvent sponge", Chemistry, 16(38), 11632 [46]; C. Volkringer, J. Marrot, G. Ferey, T. Loiseau, "Hydrothermal crystallization of three calcium-based hybrid solids with 2,6-naphthalene or 4,4'-biphenyl-dicarboxylates" Crystal Growth Design, 2008, 8, 685 [47]

MIL-88B_$4CH_3$, MIL-88B_$CH_3$, MIL-88B_$2CF_3$, MIL-88B_$2OH$, MIL-88B_$NO_2$, MIL-88B_$NH_2$, MIL-88B_Cl, MIL-88B_Br, MIL-88B_4F: For this structural type, the reader may refer to the publications concerning type MIL-88 above, namely, (a) Serre et al., "Role of solvent-host interactions that lead to very large swelling of hybrid frameworks", Science, 2007, Vol. 315, 1828-1831 [20]; (b) Surblé et al., "A new isoreticular class of metal-organic frameworks with the MIL-88 topology", Chem. Comm., 2006, 284-286 [21]; (c) Mellot-Draznieks et al., "Very large swelling in hybrid frameworks: a combined computational and powder diffraction study", J. Am. Chem. Soc., 2005, Vol. 127, 16273-16278 [22], c) Horcajada et al., "How linker's modification controls swelling properties of highly flexible iron(III) dicarboxylates MIL-88", J. Am. Chem. Soc., 2011, 133, 17839 [48]

In particular, the MOF solid according to the invention may have a unit with a formula selected from the group comprising:

Fe $(OH)[C_6H_4(CO_2)_2]$ of flexible structure, for example MIL-53 and its functionalized forms MIL-53(Fe)_X (X=Cl, Br, $CH_3$, $2CF_3$ etc.) (see reference Devic et al., "Functionalization in flexible porous solids: effects on the pore opening and the host-guest interactions", J. Am. Chem. Soc., 2010, 132, 1127 [49])

$Fe_3OX[C_2H_2(CO_2)_2]_3$ of flexible structure, for example MIL-88A $Fe_3OX[C_4H_4(CO_2)_2]_3$ of flexible structure, for example MIL-89 (see reference: C. Serre, S. Surblé, C. Mellot-Draznieks, Y. Filinchuk, G. Férey *Dalton Trans.*, 2008, 5462-5464: Evidence of flexibility in the nanoporous iron(III) carboxylate MIL-89 [50])

$Fe_3OX[C_6H_4(CO_2)_2]_3$ of flexible structure, for example MIL-88B $Fe_3OX[O_2C—C_6(CH_3)_4—CO_2]_3.nH_2O$ of flexible structure, for example MIL-88Bt $Fe_3OX[C_6H_4(CO_2)_2]_3$ of rigid structure, for example MIL-101

$Fe_3OX[C_6H_3(CO_2)_3]_3$ of rigid structure, for example MIL-100

$Al_3OX[C_6H_3(CO_2)_3]_3$ of rigid structure, for example MIL-100

$Fe_3OX[C_{10}H_6(CO_2)_2]_3$ of flexible structure, for example MIL-88C $Fe_3OX[C_{12}H_8(CO_2)_2]_3$ of flexible structure, for example MIL-88D $Zn_6N_{24}C_{48}H_{60}$ of rigid structure, for example ZIF-8

$Zr_6O_4(OH)_{4[}(CO_2)2C_6H_4]_6$ of rigid structure, for example UiO-66

$Ti8O8(OH)_4[(CO_2)2C_6H_4]_6$ of rigid structure, for example MIL-125 wherein X is as defined above.

Quite particularly, the MOF solid according to the invention may have a unit of formula selected from the group comprising:

MIL-101 (Fe) or $Fe_3O[C_6H_4—(CO_2)_2]_3.X.nH_2O$ (X=F, Cl, OH) of rigid structure MIL-101-Cl (Fe) or $Fe_3O[Cl-C_6H_3—(CO_2)_2]_3.X.nH_2O$ (X=F, Cl, OH) of rigid structure MIL-101-$NH_2$ (Fe) or $Fe_3O[NH_2—C_6H_3—(CO_2)_2]_3.X.nH_2O$ (X=F, Cl, OH) of rigid structure MIL-101-$2CF_3$ (Fe) or $Fe_3O[(CF_3)_2—C_6H_2—(CO_2)_2]_3.X.nH_2O$ (X=F, Cl, OH) of rigid structure MIL-88B-$NO_2$ (Fe) or $Fe_3O[C_6H_3NO_2—(CO_2)_2]_3.X.nH_2O$ (X=F, Cl, OH) of flexible structure MIL-88B-$2OH$ (Fe) or $Fe_3O[C_6H_2(OH)_2—(CO_2)_2]_3.X.nH_2O$ (X=F, Cl, OH) of flexible structure MIL-88B-$NH_2$ (Fe) or $Fe_3O[C_6H_3NH_2—(CO_2)_2]_3.X.nH_2O$ (X=F, Cl, OH) of flexible structure MIL-88B-$CH_3$ (Fe) or $Fe_3O[C_6H_2CH_3—(CO_2)_2]_3.x.nH_2O$ (X=F, Cl, OH) of flexible structure MIL-88B-$2CH_3$ (Fe) or $Fe_3O[C_6H_2(CH_3)_2—(CO_2)_2]_3.X.nH_2O$ (X=F, Cl, OH) of flexible structure MIL-88B-Cl (Fe) or $Fe_3O[C_6H_3Cl—(CO_2)_2]_3.X.nH_2O$ (X=F, Cl, OH) of flexible structure MIL-88B-$4CH_3$ (Fe) or $Fe_3O[C_6(CH_3)_4—(CO_2)_2]_3.X.nH_2O$ (X=F, Cl, OH) of flexible structure MIL-88B-4F (Fe) or $Fe_3O[C_6F_4—(CO_2)_2]_3.X.nH_2O$ (X=F, Cl, OH) of flexible structure MIL-88B-8r (Fe) or $Fe_3O[C_6H_3Br—(CO_2)_2]_3.X.nH_2O$ (X=F, Cl, OH) of flexible structure MIL-88B-$2CF_3$ (Fe) or $Fe_3O[(CF_3)_2—C_6H_2—(CO_2)_2]_3.X.nH_2O$ (X=F, Cl, OH) of flexible structure MIL-88D $4CH_3$ (Fe) or $Fe_3O[C_{12}H_4(CH_3)_4-(CO_2)_2]_3.X.nH_2O$ (X=F, Cl, OH) of flexible structure MIL-88D $2CH_3$ (Fe) or $Fe_3O[C_{12}H_6 (CH_3)_2—(CO_2)_2]_3.X.nH_2O$ (X=F, Cl, OH) of flexible structure MIL-88E (Pyr) (Fe) or $Fe_3O[C_4H_3N_2—(CO_2)_2]_3.X.nH_2O$ (X=F, Cl, OH) of flexible structure MIL-88F (Thio) (Fe) or $Fe_3O[C_4H_2S—(CO_2)_2]_3.X.nH_2O$ (X=F, Cl, OH) of flexible structure MIL-53-$2OH$ (Fe) or $FeO(OH)[C_6H_2(OH)_2—(CO_2)_2].X.nH_2O$ (X=F, Cl, OH) of flexible structure MIL-53-$NH_2$ (Fe) or $FeO(OH)[C_6H_2—NH_2—(CO_2)_2].X.nH_2O$ (X=F, Cl, OH) of flexible structure MIL-53-Cl (Fe) or $FeO(OH)[C_6H_2Cl—(CO_2)_2].X.nH_2O$ (X=F, Cl, OH) of flexible structure MIL-53-Br (Fe) or $FeO(OH)[C_6H_2Br—(CO_2)_2].X.nH_2O$ (X=F, Cl, OH) of flexible structure MIL-53-$2CF_3$ (Fe) or $FeO(OH)[C_6H_2(CF_3)_2—(CO_2)_2].X.nH_2O$ (X=F, Cl, OH) of flexible structure MIL-53-$CH_3$ (Fe) or $FeO(OH)[C_6H_3CH_3—(CO_2)_2].X.nH_2O$ (X=F, Cl, OH) of flexible structure MIL-53-$2COOH$ (Fe) or $FeO(OH)[C_6H_3—(CO_2)_4].X.nH_2O$ (X=F, Cl, OH) of flexible structure MIL-88G (AzBz) (Fe) or $Fe_3O[C_{12}H_8N_2—(CO_2)_2]_3.X.nH_2O$ (X=F, Cl, OH) of flexible structure MIL-88G 2C1 (AzBz-2C1) (Fe) or $Fe_3O[C_{12}H_6N_2Cl_2-(CO_2)_2]_3 \cdot X \cdot nH_2O$ (X=F, Cl, OH) of flexible structure.

Moreover, starting from one and the same carboxylic acid ligand L and the same iron bases (chains or trimers), the inventors were able to obtain MOF materials of the same general formula (I) but with different structures. This applies for example to the solids MIL-88B and MIL-101. In fact, solids MIL-88B and MIL-101 differ in the manner of connections of the ligands to the octahedron trimers: in the solid MIL-101, the ligands L self-assemble in the form of rigid tetrahedra, whereas in the solid MIL-88B, they form triangular bipyramids, making spacing between the trimers possible.

These various materials are presented in international applications WO 2009/77670 and WO 2009/77671. The manner of assembly of these ligands may be controlled during synthesis, for example by adjusting the pH. For example, the solid MIL-88 is obtained in a less acid medium than the solid MIL-101 as described in international application WO 2009/77671.

In particular, the MOF solid of the present invention may have a phase selected from the group comprising: MIL-53, MIL-88, MIL-100, MIL-101, MIL-102 as described in international application WO 2009/77671, ZIF-8, MIL-125 and UiO-66.

The MOF solid according to the invention may comprise at least one metal possessing paramagnetic or diamagnetic properties. Preferably, the MOF solid according to the invention may comprise one or more paramagnetic metals, which may be identical or different, and may be iron. In particular, the MOF solid according to the invention may comprise one or more paramagnetic metal ions, which may be identical or different, which may be selected from $Fe^{2+}$ and $Fe^{3+}$.

Moreover, the MOF solid according to the invention may be used in imaging. Furthermore, the invention also relates to the use of the MOF solid according to the invention as a contrast agent.

Indeed, contrast agents are characterized by their relaxivity. The greater the latter, the greater the effect of the contrast agents. Relaxivity corresponds to the capacity of contrast agents to modify the relaxation times of the protons of the water of the medium following application of a magnetic field. It depends on the paramagnetic properties of the metals used but also on the quantity and the mobility of the water molecules that are coordinated to the metal in the first inner sphere, making the largest contribution, as well as in the outer sphere. These "coordination spheres" represent the atoms immediately attached to the metal center in the case of the 1st sphere; for the outer sphere, this represents the atoms located immediately beyond the 1st sphere.

In the case of the solid of the invention, besides the magnetic susceptibility of the metal, in this example iron (III), the structural characteristics of the solid of the present invention allow the water to be coordinated around the 1st coordination sphere and to circulate in the pores, which induces an effect on the longitudinal T1 and transverse T2 relaxation times of the protons of the water.

In particular, the relaxivity r2 of the solid is sufficient for use in vivo in gradient-echo experiments.

Moreover, the research conducted by the inventors enabled them to develop a flexible and modulable method of synthesis for obtaining the MOF solids according to the invention having a particular isoreticular structural organization at good yields. Moreover, the method makes it possible to obtain nanoparticles with desired dimensions and homogeneous particle and pore sizes.

Thus, the invention also relates to a method for preparing a solid as defined in the present invention, comprising at least one reaction step (i) consisting of mixing, in a polar solvent:

at least one solution comprising at least one inorganic metal precursor, said precursor being in the form of metal M, of a salt of metal M or of a coordination complex comprising the metal ion M wherein M is as defined above.

at least one ligand L' of formula $-R^0(COR^3)_q$,

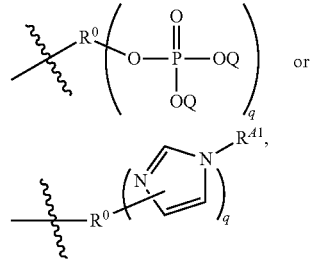

where
Q, $R^{41}$, q and $R^0$ are as defined above; and
and $R^3$ is selected from the group comprising a radical —OH, a radical —OY wherein Y represents an alkali metal cation, a halogen atom, or a radical —$OR^4$, —O—C(=O)$R^4$ or —$NR^4R^{4'}$, wherein $R^4$ and $R^{4'}$ are $C_{1-12}$ alkyl radicals;

so as to obtain said solid.

According to the invention, the method for preparing the solid of the invention may further comprise a step (iii) of fixation, on said solid, of at least one organic surface agent as defined above.

This fixation step (iii) may be carried out during or after reaction step (i) or else after a step of introduction (ii) of a molecule of interest. Cf. Examples 22, 23 and 24 of WO 2009/77671.

A number of MOF solids having a modified outer surface are illustrated in the "Examples" section. It is to be understood that these examples are given for purposes of illustration, and are not limiting. The methods for modifying the surface of the MOF solids illustrated in the Examples are applicable and/or adaptable to all of the MOF solids according to the present invention (e.g. MOF solids based on metal M different from Fe, with different ligands L, and/or encapsulating, or not, at least one active ingredient, a compound of cosmetic interest and/or a marker). For example, these methods may be employed without difficulty for modifying the surfaces of all of the MOF solids described in the present application.

Advantageously, ligand L' may represent a ligand bearing several complexing groups comprising carboxylates, phosphonates, imidazolates, preferably a di-, tri-, tetra- or hexadentate carboxylate group selected from the group comprising:

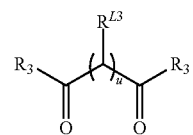

27
-continued
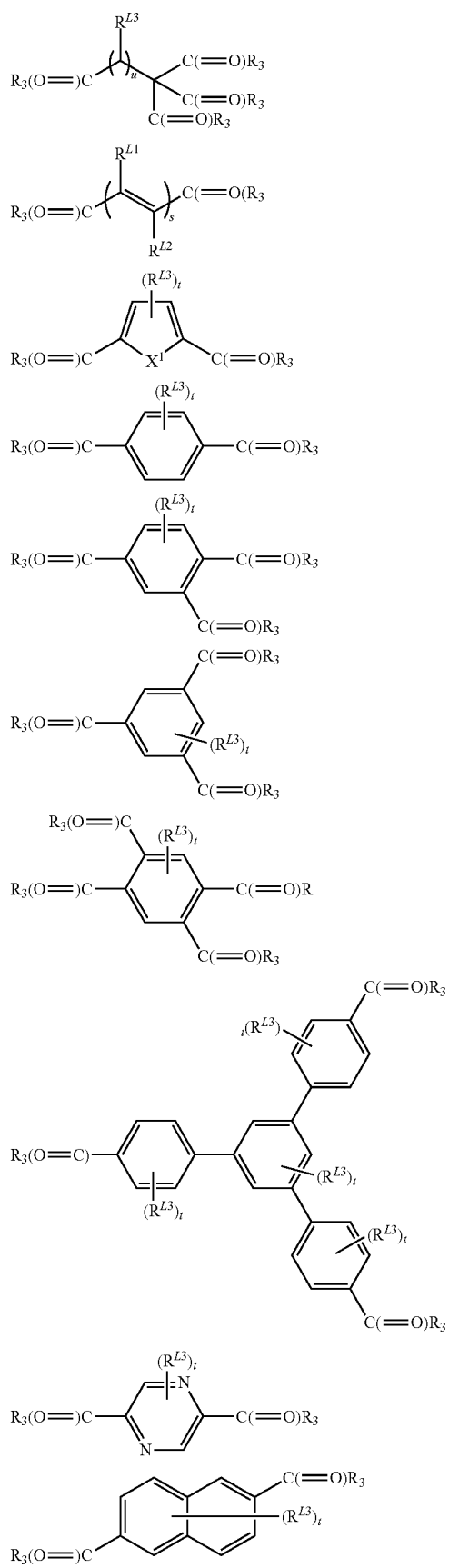
28
-continued
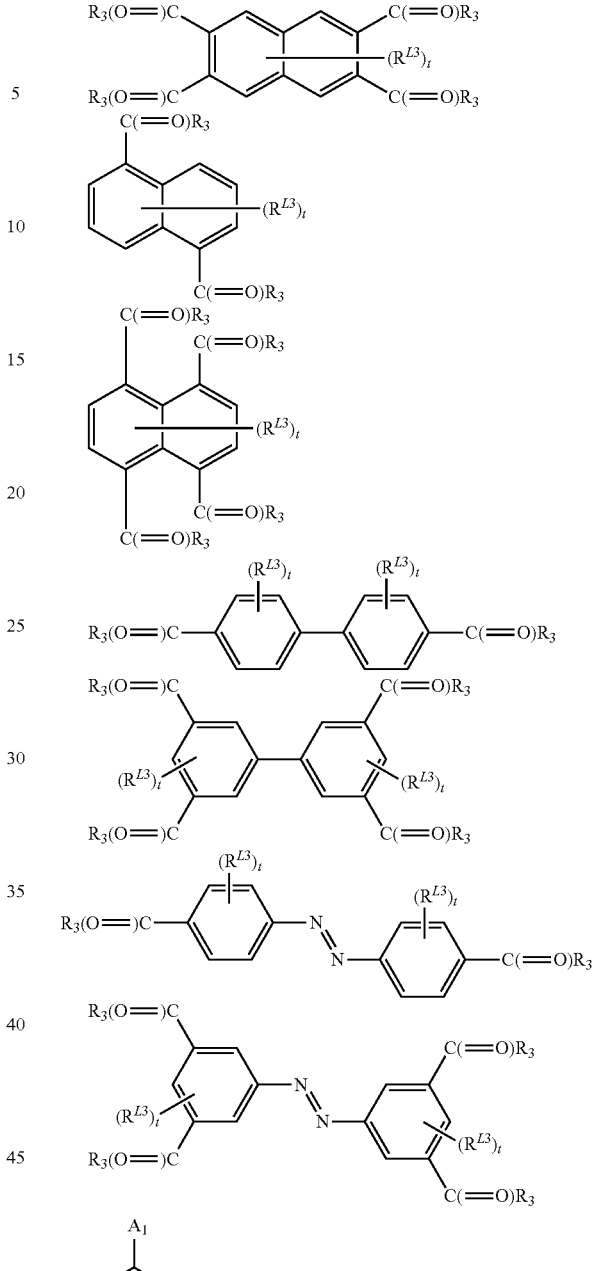
wherein:
R³ is selected from the group comprising a radical —OH, a radical —OY wherein Y represents an alkali metal cation, a halogen atom, or a radical —OR⁴, —O—C(=O)R⁴ or —NR⁴R⁴',
wherein R⁴ and R⁴' are $C_{1-12}$ alkyl radicals,
$X_1$ represents O or S,
s represents an integer from 1 to 4, each occurrence of t represents independently an integer from 1 to 4, u represents an integer from 1 to 7, $R^{L1}$ and $R^{L2}$ represent independently H, a halogen atom or a C1 to C6 alkyl (preferably methyl or ethyl), and each occurrence of $R^{L3}$ represents independently H, a halogen atom (preferably F, Cl or Br), OH, $NH_2$, $NO_2$ or a $C_1$ to $C_6$ alkyl (preferably methyl or ethyl).

In one embodiment, each occurrence of $R^3$ represents a hydrogen atom.

In one embodiment, each occurrence of the radicals $R^{L1}$, $R^{L2}$ and $R^{L3}$ represents a hydrogen atom.

Preferably, in reaction step (i), the ligand L' used may be a di-, tri- or tetracarboxylic acid selected from the group comprising: $C_2H_2(CO_2H)_2$ (fumaric acid), $C_2H_4(CO_2H)_2$ (succinic acid), $C_3H_6(CO_2H)_2$ (glutaric acid), $C_4H_4(CO_2H)_2$ (muconic acid), $C_4H_8(CO_2H)_2$ (adipic acid), $C_7H_{14}(CO_2H)_2$ (azelaic acid), $C_5H_3S(CO_2H)_2$ (2,5-thiophenedicarboxylic acid), $C_6H_4(CO_2H)_2$ (terephthalic acid), $C_6H_2N_2(CO_2H)_2$ (2,5-pyrazine dicarboxylic acid), $C_{10}H_6(CO_2H)_2$ (naphthalene-2,6-dicarboxylic acid), $C_{12}H_8(CO_2H)_2$ (biphenyl-4,4'-dicarboxylic acid), $C_{12}H_8N_2$ $(CO_2H)_2$ (azobenzenedicarboxylic acid), $C_6H_3(CO_2H)_3$ (benzene-1,2,4-tricarboxylic acid), $C_6H_3(CO_2H)_3$ (benzene-1,3,5-tricarboxylate acid), $C_{24}H_{15}(CO_2H)_3$ (benzene-1,3,5-tribenzoic acid), $C_6H_2(CO_2H)_4$ (benzene-1,2,4,5-tetracarboxylic acid, $C_{10}H_4(CO_2H)_4$ (naphthalene-2,3,6,7-tetracarboxylic acid), $C_{10}H_4(CO_2H)_4$ (naphthalene-1,4,5,8-tetracarboxylic acid), $C_{12}H_6(CO_2H)_4$ (biphenyl-3,5,3',5'-tetracarboxylic acid), and the modified analogs selected from the group comprising 2-aminoterephthalic acid, 2-nitroterephthalic acid, 2-methylterephthalic acid, 2-chloroterephthalic acid, 2-bromoterephthalic acid, 2,5-dihydroxoterephthalic acid, tetrafluoroterephthalic acid, tetramethylterephthalic acid, dimethyl-4,4'-biphenydicarboxylic acid, tetramethyl-4,4'-biphenydicarboxylic acid, dicarboxy-4,4'-biphenydicarboxylic acid, 2,5-pyrazyne dicarboxylic acid. The ligand L' used may also be selected from the group comprising: 2,5-diperfluoroterephthalic acid, azobenzene-4,4'-dicarboxylic acid, 3,3'-dichloro-azobenzene-4,4'-dicarboxylic acid, 3,3'-dihydroxo-azobenzene-4,4'-dicarboxylic acid, 3,3'-diperfluoro-azobenzene-4,4'-dicarboxylic acid, 3,5,3',5'-azobenzene tetracarboxylic acid, 2,5-dimethylterephthalic acid, perfluoroglutaric acid.

Advantageously, the ligand L' may also be a precursor of the imidazolate, tetrazolate, phosphate or phosphonate ligand such as imidazole, 2-methylimidazolate, 2-ethylimidazole, 4,(-imidazole-dicarboxylic acid, 1,4-(butanediyl)bis (imidazole), purine, pyrimidine, benzimidazolate, piperazinediphosphonate, tetrazolylbenzoate.

It is to be understood that, in implementing the method, when the ligand L' is of the carboxylate type, the latter is not necessarily in the form of a carboxylic acid. As pointed out above, the latter may be in a derived form where one or more carboxylic groups is/are in the form —C(=O)—$R^3$ wherein $R^3$ may represent a radical —OY wherein Y represents an alkali metal cation, a halogen atom, or a radical —$OR^4$, —O—C(=O)$R^4$ or —$NR^4R^{4'}$, wherein $R^4$ and $R^{4'}$ are independently $C_{1-12}$ alkyl radicals.

The synthesis of MOF materials may preferably be carried out in the presence of energy, which may be supplied for example by heating, for example hydrothermal or solvothermal conditions, but also by microwaves, by ultrasound, by grinding, by a process involving a supercritical fluid, etc. The corresponding protocols are those that are known by a person skilled in the art. Nonlimiting examples of protocols usable for the hydrothermal or solvothermal conditions are described for example in international applications WO 2009/077670 and WO 2009/077670, and in the references that are cited there for this purpose.

Hydrothermal or solvothermal conditions, where the reaction temperatures may vary between 0 and 220° C., are generally carried out in glass (or plastic) vessels when the temperature is below the boiling point of the solvent. When the temperature is higher or when the reaction is carried out in the presence of fluorine, Teflon bodies inserted in metal bombs are used.

The solvents used are generally polar. Notably the following solvents may be used: water, alcohols, dimethylformamide, dimethylsulfoxide, acetonitrile, tetrahydrofuran, diethylformamide, chloroform, cyclohexane, acetone, cyanobenzene, dichloromethane, nitrobenzene, ethylene glycol, dimethylacetamide or mixtures of these solvents.

One or more co-solvents may also be added in any step of the synthesis for better dissolution of the mixture components.

These may notably be monocarboxylic acids, such as acetic acid, formic acid, benzoic acid, etc.

When the co-solvent is a monocarboxylic acid, the latter, besides a solubilizing effect, also makes it possible to stop crystal growth of the MOF solid. In fact, the carboxylic group coordinates with the iron, which will not be able to bind to another iron atom without the presence of a second —COOH group on the molecule of co-solvent. Thus, growth of the crystal lattice is slowed down by this, and then stopped. Addition of a monocarboxylic co-solvent, such as acetic acid, formic acid, benzoic acid, etc., thus makes it possible to reduce the size of the particles of MOF solid obtained. The use of a monocarboxylic co-solvent may therefore promote the production of nanoparticles (particles of size <1 μm).

Preferably, reaction step (i) may be carried out according to at least one of the following reaction conditions:

with a reaction temperature from 0° C. to 220° C., preferably from 50 to 150° C.;

with a stirring speed from 0 to 1000 rpm (revolutions per minute), preferably from 0 to 500;

with a reaction time from 1 minute to 96 hours, preferably from 1 minute to 15 hours;

with a pH from 0 to 7, preferably from 1 to 5;

with the addition of at least one co-solvent to the solvent, to the precursor, to the ligand or to the mixture thereof, said co-solvent being selected from the group comprising acetic acid, formic acid, benzoic acid;

in the presence of a solvent selected from the group comprising water, the $R^s$—OH alcohols wherein $R^s$ is a linear or branched $C_1$ to $C_6$ alkyl radical, dimethylformamide, dimethylsulfoxide, acetonitrile, tetrahydrofuran, diethylformamide, chloroform, cyclohexane, acetone, cyanobenzene, dichloromethane, nitrobenzene, ethylene glycol, dimethylacetamide or mixtures of these solvents, miscible or not;

in a supercritical medium, for example in supercritical $CO_2$;

under microwaves and/or under ultrasound;

in conditions of electrochemical electrolysis;

in conditions using a rolling crusher;

in a gas stream.

The synthesis of MOF materials may preferably be carried out in experimental conditions favorable to the formation of nanoparticles. For example, control of the following parameters may be important for producing nanoparticles of MOF solids according to the invention:

reaction temperature, reaction time, concentrations of ligand L' and of inorganic metal precursor and/or addition of one or more additives such as pH modifiers (acids, bases), mineralizing agents, or agents promoting stoppage of crystal growth (monocarboxylic acid).

The preferred ranges of values of each of these parameters may vary depending on whether the synthesis of the nanoparticles is carried out by the hydro/solvothermal route, by ultrasound or by microwaves. For example, a higher reaction temperature will generally be used for the hydro/solvothermal route (about 20-150° C.) than for the route using ultrasound (about 0° C.)

Moreover, the inventors have also demonstrated the particular structural characteristics of the solid of the present invention, notably in terms of flexibility or of pore size, which endows it with particularly interesting properties, notably in terms of capacity for adsorption, selective adsorption and purity. These materials therefore make selective adsorption of the molecules possible, for example pharmaceutical molecules, with a favorable energy cost and a longer release time. Thus, the research conducted by the inventors has enabled them to demonstrate the advantage of the MOF materials for the adsorption and transport of active ingredients.

Thus, the invention also relates to the use of the MOF solid according to the invention, which comprises at least one pharmaceutically active ingredient in its pores or on its surface.

In particular, the invention also relates to the use of the MOF solid according to the invention, loaded with a pharmaceutically active ingredient, as a medicament. The pharmaceutically active ingredient may be contained either in the pores, or on the surface of the solid according to the invention. This is what is meant in the rest of this document by "MOF solid loaded with pharmaceutically active ingredient".

More generally, "MOF solid loaded with component X" refers to a MOF solid according to the invention containing component X in its pores or on its surface. Component X may be adsorbed or bound by a covalent bond, hydrogen bond, by a van der Waals bond, by electrostatic interaction at the surface or in the pores of the MOF solid. This component X may be, as stated above, a pharmaceutically active ingredient.

In the present text, "active ingredient" refers to a molecule that has a therapeutic effect. For example, it may be any molecule having therapeutic properties that is included in the composition of a medicament. We may mention for example nonsteroidal anti-inflammatories (NSAIDs), abortifacients, alpha-blockers, alpha2-agonists, aminoglycosides, analgesics, anesthetics, local anesthetics, anorexigenic agents, 5HT3 antagonists, calcium antagonists, antianginal drugs, antiarrhythmics, antibiotics, anticholinergics, anticholinesterase drugs, antidiabetic agents, antidiarrhea agents, antidepressants, antihistamines, antihypertensives, antimycotics, antimalarials, antiparasitics, antipsychotics, antipyretics, antiretrovirals, antiseptics, antispasmodics, antivirals, antiemetics, antiepileptics, anxiolytics, barbiturates, benzodiazepines, bronchodilators, beta-blockers, chemotherapeutic agents, corticosteroids, diuretics, loop diuretics, osmotic diuretics, depressants, glucocorticoids, hallucinogens, hypnotics, immunosuppressants, carbonic anhydrase inhibitors, neuraminidase inhibitors, proton pump inhibitors, TNF inhibitors, selective serotonin reuptake inhibitors, inhibitors of HMG-CoA reductase (or statins), keratolytics, laxatives, mineralocorticoids, muscle relaxants, neuroleptics, psychotropic drugs, spasmolytics, stimulants, sedatives, tocolytics or vasodilators. This list is not exhaustive and extends to any therapeutic active ingredient known by a person skilled in the art.

Indeed, the MOF solid according to the invention has the advantage of having large capacities for adsorption or for loading. In fact, the solid of the invention has a favorable hydrophobic/hydrophilic internal micro-environment, notably for incorporating amphiphilic molecules such as busulfan. Moreover, it allows efficient adsorption of the pharmaceutical molecules that present particular difficulties in encapsulation, for example on account of their instability, their great reactivity, their low solubility, their strong tendency to crystallize, their hydrophilic, amphiphilic character, etc.

For example, the solid according to the invention may be loaded with at least one pharmaceutically active ingredient that displays one or more of the following characteristics: hydrophilic, amphiphilic, lipophilic, unstable, toxic, with strong tendency to crystallize or practically insoluble.

"Toxic" refers to a pharmaceutically active ingredient having toxic effects that may hinder its use in medical or veterinary applications. It may be for example alkylating agents such as busulfan, cisplatin, the nitroso-ureas such as lomustine. The alkylating agents form, after metabolization, covalent bonds with nucleic acids. Formation of these bonds may lead for example to:
disorders of DNA transcription and replication
substitutions of bases in DNA
excisions of bases and chain breaks in DNA.

Their main pharmacological activity is manifested during the phase of DNA synthesis. Their toxic effects may include: myelosuppression, sterility and nonlymphocytic leukemia.

Cisplatin causes intra-chain DNA bridges, has low myelotoxicity, but it is severely emetic and may be nephrotoxic.

"With strong tendency to crystallize" refers to a pharmaceutically active ingredient that has a tendency to self-associate in a crystal lattice instead of being incorporated in other structures. Thus, such a compound tends to form crystals during the encapsulation process used, instead of being incorporated in the particles. Therefore the result at the end of the process is a mixture of particles with little loading with pharmaceutically active ingredient and crystals of the latter. It may be busulfan, for example. At high dose, it displays a serious side-effect: veno-occlusive disease of the liver. The latter probably results from this molecule's very strong tendency to crystallize. Crystal stacking is governed by strong dipole-dipole interactions between the methylsulfonate groups of this active ingredient.

"Practically insoluble" refers to a pharmaceutically active ingredient whose solubility is below 0.1 mg/mL in water. It may be for example busulfan.

"Unstable" refers to a pharmaceutically active ingredient that may decompose, crystallize and/or react, losing its structure and its activity. It may be for example busulfan.

Moreover, the pharmaceutically active ingredient may be any molecule having biological activity, for example a medicament, notably an anticancer drug, an antiviral agent, a nucleoside analog, whether modified or not, a nucleic acid, an antibody, a protein, a vitamin, etc.

Among the hydrophilic active ingredients, we may mention for example azidothymidine, whether or not phosphated, CDV (cidofovir), 5-fluoroacil, cytarabine.

Among the amphiphilic active ingredients, we may mention for example busulfan, doxorubicin chloride, imipramine chloride.

Among the lipophilic active ingredients, we may mention for example tamoxifen, docetaxel, paclitaxel, ibuprofen, lidocaine, the fat-soluble vitamins such as vitamins A (retinol), D (calciferol), E (tocopherol), K1 (phylloquinone), K2 (menaquinone).

In particular, the solid according to the invention may be loaded with at least one pharmaceutically active ingredient selected for example from the group comprising Taxotere, busulfan, azidothymidine (AZT), azidothymidine phosphate (AZTP), ibuprofen, cidofovir, the antibiotics, gemcitabine, tamoxifen, zalcitabine (ddC), didanosine (ddI).

Advantageously, the solid according to the invention may be loaded with at least one pharmaceutically active ingredient selected for example from the group comprising busulfan, azidothymidine (AZT), azidothymidine phosphate (AZTP), cidofovir, gemcitabine, ibuprofen.

Moreover, the solid according to the invention may be loaded with at least one compound of cosmetic interest.

"Compound of cosmetic interest" refers to any active substance included in the formulation of a cosmetic preparation, i.e. a preparation intended to be brought into contact with various surface parts of the human body, notably the epidermis, the bristle and hair systems, the external organs, the teeth and the mucosae, for the purpose, exclusively or mainly, of cleaning, protecting, and perfuming them, of maintaining the human body in good condition, of modifying its appearance or of correcting odor. "Active substance" refers to a substance that provides the efficacy of the cosmetic preparation.

The compound of cosmetic interest may be an active substance included in the preparation of any cosmetic preparation known by a person skilled in the art, for example hygiene products (e.g. for makeup removal, toothpaste, deodorant, shower gel, soap, shampoo), care products (e.g. antiwrinkle cream, day cream, night cream, hydrating cream, floral water, peeling, milk, beauty masks, lip balm, tonic), hair products (e.g. conditioning, straightening, gel, oil, lacquer, masks, dyes), makeup products (e.g. concealer, self-tanning agents, eyeliner, makeup, foundation, khol, mascara, powder, skin whitening product, lipstick, nail varnish), perfumes (e.g. eau de Cologne, toilet water, perfume), sunscreen products (e.g. after-sun and sunscreen creams, oils or lotions), shaving products and depilatories (e.g. aftershave, depilatory cream, shaving foam), or bath and shower preparations (e.g. foam bath, bath oil, bath salts).

According to the invention, the compound of cosmetic interest may be selected for example from the group comprising:
- an antioxidant (for example citric acid, beta-carotene, vitamin E, glycolic acid, glutathione, vitamin C, polyphenols, lycopene, flavonoids, tannins, anthocyans, N-acetylcysteine (anti-free radical))
- a vitamin (for example vitamin A, B3, B5, B6, B2, B1, B9, B8, B12, C, E, D, K, K1, K2)
- a liporegulator (for example caffeine, theophylline)
- a photoprotective agent (for example benzophenone 3 (2-hydroxy-4-methoxybenzophenone), benzophenone 4 (2-hydroxy-4-methoxybenzophenone-5-sulfonic acid), 2-phenylbenzimidazole-5-sulfonic))
- a hydrating agent (for example urea, hyaluronic acid, sorbitol).

For example, the solid according to the invention may be loaded with at least one compound of cosmetic interest selected from the group comprising benzophenone, visnadine, salicylic acid, ascorbic acid, benzophenone and derivatives thereof, caffeine, urea, hyaluronic acid, etc.

According to the invention, the organic surface agent may moreover be functionalized with a fluorescent molecule. For example, it may be rhodamines (for example rhodamine B), fluorescein, luciferase, pyrene and derivatives thereof, aminopyrrolidino-7-nitrobenzofurazan or quantum dots.

For example, the quantum dots may be selected from cadmium selenide, cadmium sulfide, indium arsenide, indium phosphide or cadmium selenide sulfide.

Advantageously, the active ingredient may be a fluorinated molecule; i.e. comprising at least one substituent F. It may be for example one of the fluorinated molecules mentioned above. These fluorinated molecules are suitable for uses in imaging, particularly fluorescence imaging such as the PET technique mentioned above.

Thus, the invention also relates to the use of MOF nanoparticles encapsulating one or more fluorinated molecules according to the invention as a marker usable in medical imaging, such as PET imaging.

For example, the solid according to the invention may be loaded with a pharmaceutically active ingredient with a loading capacity from 1 to 200 wt % of dry solid, for example from 1 to 70 wt % of dry solid, i.e. from about 10 to 700 mg per gram of dry solid.

In the context of the present invention, loading capacity signifies the capacity for storing molecules or the quantity of molecules adsorbed in the material. The loading capacity may be expressed in capacity by weight (gram/gram) or in molar capacity (mol/mol) or in other ways (mol/gram, gram/mol, etc.).

Moreover, another problem in the art concerns rapid, uncontrolled release of the molecules transported in the absence of affinity. The MOF solid with modified outer surface according to the invention has the advantage of allowing longer release times, notably owing to the internal micro-environment but also owing to the structure of the compounds. In fact, the use of surface agents having a size larger than the pore access windows of the MOF materials, functionalized with ligands that are very complexing of metals, such as iron ($Fe^{2+}$, $Fe^{3+}$), zinc ($Zn^{2+}$), zirconium ($Zr^{4+}$), titanium ($Ti^{4+}$), calcium ($Ca^{2+}$), magnesium ($Mg^{2+}$) and aluminum ($Al^{3+}$), makes it possible to obtain stable coverings, but without disturbing the encapsulated molecules.

The solid according to the invention may also comprise, for example on the spacer ligands, functional groups that are able to modify the interactions between the MOF solid according to the invention and the molecule of interest. This may make it possible to control the encapsulation and release of the molecules of interest. The MOF materials of the invention may thus be adapted, formulated and designed in relation to the molecules of interest to be transported in order to modulate the level of encapsulation, the release of the molecules and/or the degradability of the solid.

Moreover, the MOF solid according to the invention has been the subject of very positive toxicity studies, described below in the "Examples" section.

Thus, the MOF solid of the present invention used for transporting the active ingredients is able to overcome the problems of the art mentioned above, notably the problems connected with instability of the coverings of the MOF vehicle, notably in a biological environment, and with their interference with the release of the molecules encapsulated in the pores of the MOFs having a modified outer surface.

Moreover, the MOF solid according to the invention allows markers to be incorporated in this material, which is also of interest.

Thus, according to a particular embodiment, the solid according to the invention may be loaded with at least one molecule of interest, which may be a pharmaceutically active ingredient and/or a compound of cosmetic interest and/or a marker. The molecule of interest may be contained either in the pores, or on the surface of the solid according to the invention.

Thus, the MOF solids according to the invention may be used for manufacturing medicaments, cosmetic compositions and/or markers usable in medical imaging.

Thus, a method is supplied for treating a subject affected by a disease, said method comprising the administration, to said subject, of a MOF solid according to the invention comprising, in its pores or on its surface, at least one active ingredient known for treating said disease.

In particular, the MOF solid according to the invention may be loaded with at least one marker selected from the group comprising a marker for medical imaging, a contrast agent, a tracer, a radioactive marker, a fluorescent marker, a phosphorescent marker.

For example, the inventors describe, in the "Examples" section below, surface modification with a fluorescent compound, in particular a cyclodextrin or a polycyclodextrin labeled with rhodamine. This modification allows the particles to be detected using a confocal microscope. The confocal laser scanning microscope (CLSM) is an optical microscope that has the property of producing images with very low depth of field (about 600 nm), called "optical sections". By positioning the focal plane of the objective at different levels of depth in the specimen, it is possible to produce series of images, from which a three-dimensional representation of the object may be obtained. A possible application is investigation of the interactions with cell lines.

Moreover, the nanoparticles labeled with fluorescent compounds may be used in fluorescence imaging.

In particular, the solid according to the invention may be loaded with at least one marker selected from the group comprising: a fluorescent compound, an iron oxide, a gadolinium complex, gadolinium ions directly present in the structure, for example in the form of a complex with the organic ligand, etc. The protocols for marker loading are those known by a person skilled in the art. Nonlimiting examples that may be used are described for example in A. K. Gupta, et al., *Nanomed.* 2007 2(1), 23-39 [28]; P Caravan, *Chem. Soc. Rev.*, 2006, 35, 512-523 [29]; or Yan-Ping Ren, et al., *Angew. Chem. Int. Ed.* 2003, 42, No. 5, 532 [30].

Thus, the MOF solid according to the invention may be used for the manufacture, transport and/or vectoring of markers.

Moreover, the solid of the invention may be used for the vectoring of medicaments when it is loaded with a pharmaceutically active ingredient and/or for the detection and monitoring of diseases involving biological targets (such as cancer) when it is used as a marker.

Moreover, by combining these two uses, the solid of the present invention advantageously makes it possible to visualize the biodistribution of a medicament. This is of considerable interest, notably for monitoring a therapeutic treatment and studying the biodistribution of a medicament.

According to a particular embodiment of the invention, the method for preparing the solid according to the invention may further comprise a step (ii) of introduction, in the pores or on the surface of the MOF solid, of at least one molecule of interest, which may be a pharmaceutically active ingredient and/or a compound of cosmetic interest and/or a marker.

Said step of introduction may be carried out during reaction step (i) or after the latter so as to obtain a solid loaded with a molecule of interest.

Any method known by a person skilled in the art may be used in the step of introduction (ii). The molecule of interest may for example be introduced into the MOF material of the present invention:
- by impregnation, by immersing the material in a solution of the molecule of interest;
- by sublimation of the molecule of interest, the gas then being adsorbed by the material; or
- by grinding by rotating roller, consisting of mechanically mixing the material and the molecule of interest.

The MOF materials of the present invention therefore constitute improved compounds capable of evading the immune system and/or evading capture by certain organs, for example the liver, thus avoiding their accumulation in these organs, and capable of carrying active ingredients to specific targets.

The improved method of surface modification of MOFs presented in the present patent application makes it possible to:
- ensure better stability of the covering in a biological environment
- avoid disturbing the encapsulation and release of the active molecules that are intended to be vectored by the MOF materials in question.

These compounds are also capable of transporting active ingredients, for example active ingredients presenting particular difficulties in encapsulation connected with their instability, their strong tendency to crystallize, their low solubility, their amphiphilic or hydrophilic character, etc.

Moreover, they allow controlled release of the active ingredients.

As described in the "Examples" section, the phosphated cyclodextrins have been used as surface agent according to the invention. The cyclodextrins (CD) are very good candidates as they are larger than the pore access windows of iron trimesate MIL-100(Fe), one of the nanoMOFs having the largest pores (cf. FIGS. 1 and 2). These cyclodextrins were functionalized with phosphate groups capable of bonding stably by coordination with the unsaturated sites of iron, zinc, zirconium, titanium, calcium, magnesium and/or aluminum on the surface of the MOFs. In order to avoid rapid detachment of the surface agents from the MOFs in a physiological environment, due both to the high pH (7.4) and to the presence of free phosphate ions, generally leading to dissolution of the metal carboxylate matrix to form metal oxides and/or phosphates, the strategy proposed in the present application employs grafting of groups, with complexing power either equivalent to or greater than that of the phosphates, or in sufficient number to increase the attachment of the organic surface agent on the surface of the MOF (cooperative effect).

The surface modification according to the invention may be obtained by simple incubation in solutions of cyclodextrin phosphate (CD-P). It is a quick and easy method (less than 15 minutes) which moreover has the advantage of a "green pharmaceutical" (although for encapsulation of hydrophobic molecules, an organic solvent might be used). In fact, the surface modification does not require addition of any organic solvent, surfactant or other chemical that is to be removed at the end of the reaction. This method could therefore be extrapolated to the industrial scale.

As described in the "Examples" section, the crystallinity and the pore volume of the MOFs modified with the phosphated cyclodextrins are not affected, in contrast to the PEG surface agents described in application WO 2009/077671. In fact, the pore volume of the samples grafted with cyclodextrin phosphate is close to that of the initial solid (cf. FIG. 7A).

The surface modification was confirmed by NMR, IR, ITC, measurement of zeta potential, and microscopy. After just 15 minutes, the nanoMOFs are covered with CD-P representing up to 20% of their weight (more than 32% after 24 h of incubation), which is very significant and shows the great affinity of the CD-P for the surface of the nanoMOFs (FIG. 5). This covering does not disappear after washing in water and remains stable in PBS even after 24 h of incubation (FIG. 9), in contrast to the linear PEG and/or dextran coverings described in application WO 2009/0077671.

Moreover, the CD-P coverings have a beneficial effect on the stability of the nanoMOFs, in that the latter no longer aggregate even after several days of incubation in water (FIG. 10). This aspect is particularly important for the applications (biological, cosmetic) and for storage of the MOF particles.

Moreover, the CD-P coverings do not alter the kinetics of release of the encapsulated molecules. This was clearly demonstrated with azidothymidine triphosphate (AZT-TP), the active form of the antiretroviral AZT (FIG. 11). In the case of linear PEGs, very rapid release ("burst effect") takes place from the first few minutes of incubation.

The aforementioned advantages and properties of the MOFs having an outer surface modified with cyclodextrin phosphates may also be obtained with the other surface agents according to the present invention, namely the cyclodextrin monomers, oligomers or polymers; branched polyethylene glycol groups; proteins; polysaccharides bearing a plurality of polyethylene glycol side chains; or polysaccharides that are water-insoluble at 6<pH<8 and water-soluble at pH<5, which are complexed to a metal center M or to a ligand L located on the surface of the crystalline MOF solid via one or more phosphate, phosphonate, bisphosphonate, sulfate, carboxylate, azolate (for example imidazolate), amido and/or amino group(s).

Other advantages may also occur to a person skilled in the art on reading the examples given below, referring to the appended figures, given for purposes of illustration, and nonlimiting.

EXAMPLES

Figure 1A:
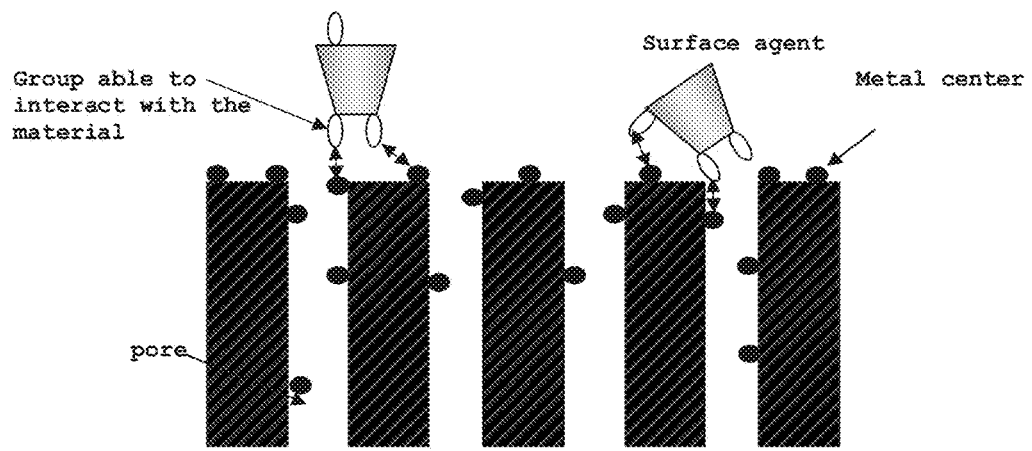
FIG. 1. Schematic representation of a porous MOF surface-modified with surface agents possessing several groups allowing interaction with the metal centers or the ligands on the surface, and having:
(A) a rigid section larger than the largest windows of the material (for example cyclodextrins);
(B) a rigid section smaller than the largest windows of the material, but groups distributed on the entire length of the main chain of the surface agent (for example dextran grafted with alendronates).
Figure 1B:
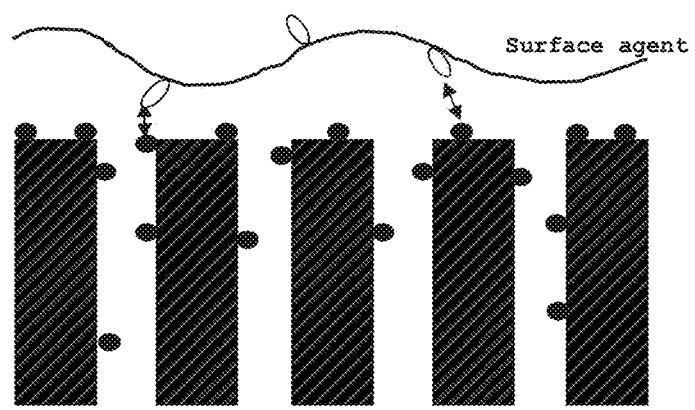

In the "Examples" section that follows, the abbreviation "MIL-100" denotes the iron carboxylate MOF of formula $Fe_3O[C_6H_3(CO_2)_3]_2.X.nH_2O$ (X=F, Cl, OH).

Example 1

Syntheses of Nanoparticles of Various MOFs

MIL-89 nano $Fe_3OX[C_4H_4(CO_2)_2]_3$ $nH_2O$ (X=F, Cl, OH)

MIL-89 nano was synthesized from iron acetate (1 mmol; synthesized according to the procedure described in C. T. Dziobkowski, T. J. Wrobleski, D. B. Brown, Inorg. Chem. 1982, 21, 671 [51]) and muconic acid (1 mmol; Fluka, 97%) in 5 mL of ethanol (Riedel-de Haën, 99.8%) with addition of 0.25 mL of 2M sodium hydroxide (Alfa Aesar, 98%) in an autoclave (Paar bomb) at 100° C. for 12 h. After cooling the container, the product was recovered by centrifugation at 5000 rpm for 10 minutes.

200 mg of the solid was suspended in 100 mL of distilled water with stirring for 15 h to remove any solvent remaining in the pores. The solid was then recovered by centrifugation at 5000 rpm for 10 minutes.

The particle size measured by light scattering was 400 nm.

The nanoparticles show a rounded and slightly elongated morphology, with a very uniform particle size of 50-100 nm.

MIL-88Anano $Fe_3OX[C_2H_2(CO_2)_2]_3nH_2O$ (X=F, Cl, OH)

The material MIL-88Anano was obtained by adding 1 mL of acetic acid (Aldrich, 99.7%) to a solution of $FeCl_3.6H_2O$ (1 mmol; Alfa Aesar, 98%) and fumaric acid (1 mmol; Acros, 99%) in 15 mL of ethanol (Riedel-de Haën, 99.8%). The solution was put in a glass bottle and heated at 65° C. for 2 hours. The solid was recovered by centrifugation at 5000 rpm for 10 minutes.

200 mg of the solid was suspended in 100 mL of distilled water with stirring for 15 h to remove any solvent remaining in the pores. The solid was then recovered by centrifugation at 5000 rpm for 10 minutes.

The particle size measured by light scattering was 250 nm. The SEM images show elongated particles with edges. There are two particle sizes, ~500 nm and 150 nm.

MIL-100 nano $Fe_3O[C_6H_3(CO_2)_3]_2.X.nH_2O$ (X=F, Cl, OH)

The MIL-100 nanoparticles were obtained by hydrothermal synthesis under microwave irradiation (Mars 5, CEM), by heating an aqueous suspension containing 20 ml of deionized water, 8.97 mmol of $FeCl_3$ ($FeCl_3.6H_2O$, 98% Alfa Aesar) and 4.02 mmol of 1,3,5-benzenetricarboxylic acid (BTC, Sigma Aldrich) for 6 min at 130° C. with stirring. The details of the synthesis are presented in Table 1 (reaction conditions for hydrothermal synthesis of MOF MIL-100 (Fe)).

TABLE 1

Hydrothermal synthesis of MOF MIL-100(Fe) aided by microwave irradiation

| Reagents | | | Parameters | | | | |
|---|---|---|---|---|---|---|---|
| $FeCl_3$ | BTC | $H_2O$ | Method | Power | Temperature | Time | Stirring |
| 8.97 mmol | 4.02 mmol | 110.16 mmol | Standard control | 400 W | 130° C. | 6 min | High |

At the end of the reaction the nanoparticles were recovered by centrifugation at 5600×g for 15 min and they were activated by 6 washings with 30 ml of EtOH absolute. Once activated, they were redispersed in EtOH, sonicated with an ultrasonic probe until a size <300 nm and a PDI<0.3 were reached. Finally, the MIL-100s were centrifuged for 15 min at 5600×g, the supernatant was removed and the nanoparticles were stored at room temperature until the time for analysis.

MIL-101 nano $Fe_3OX[C_6H_4(CO_2)_2]_3$ $nH_2O$ (X=F, Cl, OH)

To obtain the MIL-101 nano solid, a solution of $FeCl_3.6H_2O$ (1 mmol; Alfa Aesar, 98%) and 1,4-benzenedicarboxylic acid (1.5 mmol; 1,4-BDC Aldrich, 98%) in 10 mL of dimethylformamide (Fluka, 98%) was put in a Paar bomb and heated at 100° C. for 15 hours. The solid was recovered by centrifugation at 5000 rpm for 10 minutes.

To remove acid remaining in the pores, the product was heated at 200° C. under vacuum for 1 day. Store under vacuum or inert atmosphere as the product was not stable in air.

The particle size measured by light scattering was 310 nm.

MIL-88Btnano $Fe_3OX[C_6(CH_3)_4(CO_2)_2]_3nH_2O$ (X=F, Cl, OH)

The MIL-88Btnano solid was synthesized from a solution of $FeCl_3.6H_2O$ (1 mmol; Alfa Aesar, 98%) and 1,4-benzenetetramethyldicarboxylic acid (1 mmol; Chem Service) in 10 mL of dimethylformamide (Fluka, 98%) with 0.4 mL of 2M NaOH. This solution was put in a Paar bomb and heated at 100° C. for 2 hours. After cooling the container with cold water, the product was recovered by centrifugation at 5000 rpm for 10 minutes.

200 mg of the solid was suspended in 100 mL of distilled water with stirring for 15 h to remove any solvent remaining in the pores. The solid was then recovered by centrifugation at 5000 rpm for 10 minutes.

Measurement of particle size by light scattering shows two populations of nanoparticles of 50 and 140 nm.

The nanoparticles of the MIL-88Btnano solid have a spherical morphology with a size of 50 nm. Only a minor fraction has a size of 200 nm. Agglomerates of small particles may also be observed.

MIL-88Bnano $Fe_3OX[C_6H_4(CO_2)_2]_3nH_2O$ (X=F, Cl, OH)

The MIL-88Bnano solid was synthesized from a solution of iron acetate (1 mmol; synthesized according to the procedure described in C. T. Dziobkowski, T. J. Wrobleski, D. B. Brown, Inorg. Chem. 1982, 21, 671) and 1,4-benzenedicarboxylic acid (1 mmol; 1,4-BDC Aldrich, 98%) in 5 mL of methanol (Aldrich, 99%). This solution was put in a Paar bomb and heated at 100° C. for 2 hours. After cooling the container with cold water, the product was recovered by centrifugation at 5000 rpm for 10 minutes.

200 mg of the solid was suspended in 100 mL of distilled water with stirring and reflux for 200 mg of the solid was suspended in 100 mL of distilled water with stirring for 15 h to remove the solvent that remains in the pores. Afterwards, the solid was recovered by centrifugation at 5000 rpm for 10 minutes.

Measurement of particle size by light scattering shows a bimodal distribution of nanoparticles of 156 and 498 nm. The morphology of the particles was very irregular, with a size of 300 nm.

ZIF-8 (Zn)_nano $Zn_6N_{24}C_{48}H_{60}n.H_2O$

Nanoparticles of zinc imidazolate ZIF-8(Zn)_nano (Ref.: J. Mater. Chem., 2010, 20, 7676-7681; A. Demessence, et al., J. Mater. Chem., 2010, 20, 7676-7681 [31]) were synthesized starting from a solution of $Zn(NO_3)_2.6H_2O$ (2.933 g, 9.87 mmol; 98% Sigma-Aldrich) in 200 mL of methanol (Aldrich, 99%). This solution was poured into a solution of 2-methylimidazole (Hmim; 6.489 g, 79.04 mmol; 99% Aldrich) in 200 mL of methanol with stirring at room temperature for 1 hour. The product was recovered by centrifugation at 10500 rpm for 15 minutes.

200 mg of the solid was suspended in 10 mL of absolute ethanol with stirring for 15 min. This washing procedure was repeated three times. The particle size measured by light scattering was 30 nm.

UiO-66 (Zr)_nano $Zr_6O_4(OH)_4(CO_2)_2C_6H_4)_6nH_2O$

Nanoparticles of zirconium terephthalate UiO-66(Zr) nano (Ref.: J. H. Cavka et al., JACS, 2009, 130, 13850-13851 [32]) were synthesized starting from a solution of $ZrOCl_2.8H_2O$ (3.22 g, 10 mmol; 99% Sigma-Aldrich) and 1,4-benzenedicarboxylic acid (1.662 g, 10 mmol; 1,4-BDC Aldrich, 98%) in 50 mL of dimethylformamide (DMF; Fluka, 98%) at 130° C. for 2 hours. The solid was recovered by centrifugation at 10500 rpm for 15 minutes.

200 mg of the solid was suspended in 10 mL of DMF overnight. Then the product recovered by centrifugation (10500 rpm for 15 minutes) was suspended in 10 mL of methanol for 1 h. This washing with methanol was repeated twice. The particle size measured by light scattering was 280 nm.

MIL-100(Al)_nano $Al_3OX[(CO_2)_3C_6H_3]_2nH_2O$ (X=F, Cl, OH, $NO_3$)

Nanoparticles of aluminum trimesate MIL-100(Al)_nano were synthesized by dispersing 1.21 grams (0.05 mol) of 1,3,5-methyl benzentricarboxylate in 20 mL of water using an ultrasonic rod (20 s at 20% then 20 s at 30%). The mixture was then stirred magnetically and 2.6629 g of aluminum nitrate nonahydrate was poured in. Then 4 mL of 4 M nitric acid was added to the resultant dispersion, which was stirred again for 5 minutes before heating. Synthesis was carried out under microwave irradiation at 210° C. for 30 min with a heating ramp of 10 min. The reactor was taken out of the microwave oven when the temperature has dropped to 90° C. and the reactor was cooled in an ice bath. The solid was recovered by centrifugation at 10500 rpm for 20 minutes.

After removing and discarding the liquid fraction, the deposit (pellet) was dispersed again in 30 mL of methanol and was stirred magnetically overnight. The dispersion was finally centrifuged in the conditions described above, obtaining a yellow solid.

The particle size measured by light scattering was 120 nm.

In all the above examples, determination of particle size by light scattering was performed on a Malvern Zetasizer Nano series—Nano-ZS; model Zen 3600; serial No. 500180; UK. Scanning electron microscopy was performed using a Topcon microscope (Akashi) EM 002B ultra-high resolution 200 kV.

Example 2

Synthesis of Nanoparticles of Iron Trimesate MIL-100 Functionalized with βCDP

Figure 2:
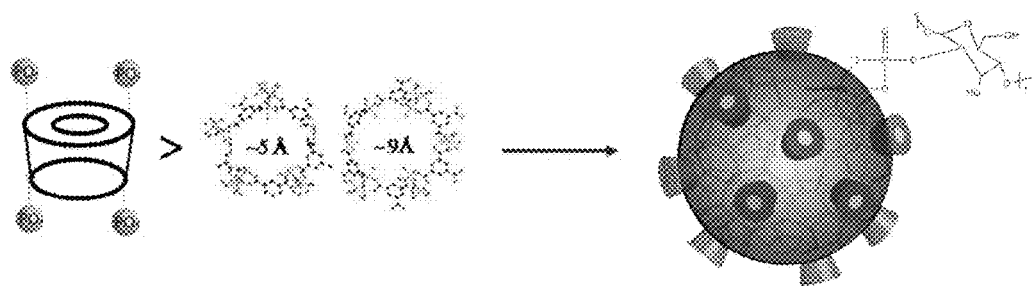
FIG. 2: Schematic representation of the βCDP-MIL-100 interaction (βCDP=β-cyclodextrin phosphate).

The organic-inorganic hybrid nanoparticles (nanoMOF) based on iron trimesate (MIL-100) were modified with β cyclodextrin phosphate (βCDP, Cyclolab, CY-2017.1, molecular formula: $C_{42}H_{70}O_{47}P_4Na_4$). This molecule has two fundamental characteristics for effective surface modification of nanoMOFs: 1) it has a bulkier structure than the micropore windows of MIL-100s, which should prevent its adsorption into the pores, thus preserving the porosity of the nanoparticles; 2) it is substituted with four phosphate groups, which should ensure stable interaction with the nanoparticles by the formation of ionocovalent bonds with the iron atoms on the surface of the particles (FIG. 2).

2 mg of MIL-100 was modified by incubation with 500 µl of an aqueous solution of βCDP 2 mg/ml (weight ratio nanoparticles:βCDP=1:0.5), for 24 h with stirring at room temperature. After incubation, the modified nanoparticles were recovered by centrifugation at 5600×g for 10 min. The pellet and the supernatant were analyzed to characterize the interaction of βCDP with MIL-100 by direct and indirect methods. In certain cases, another weight ratio (nanoparticles:βCDP=1:2) and other incubation times were tested.

c) Physicochemical Characterization of MIL-100

XRD (X-Ray Diffraction) Analysis

Figure 3:
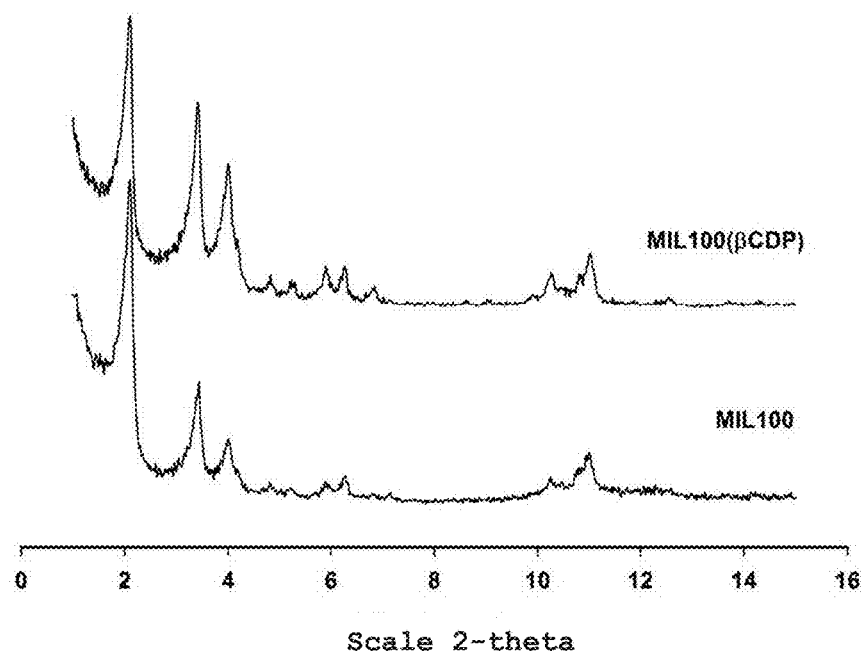
FIG. 3: X-ray powder diffraction (XRPD) patterns of a MOF MIL-100 before and after functionalization with βCDP.

The MIL-100 nanoparticles, unmodified and modified with βCDP, were dried for 8 h at 100° C. and their structure was analyzed by X-ray diffraction (Siemens D5000 X'Pert MDP high-resolution diffractometer (θ-2θ) (λCu, Kα1, Kα2)). The results showed that the method of functionalization of the surface of MIL-100 with βCDP does not alter the crystal structure of the nanoparticles (FIG. 3).

Figure 4:
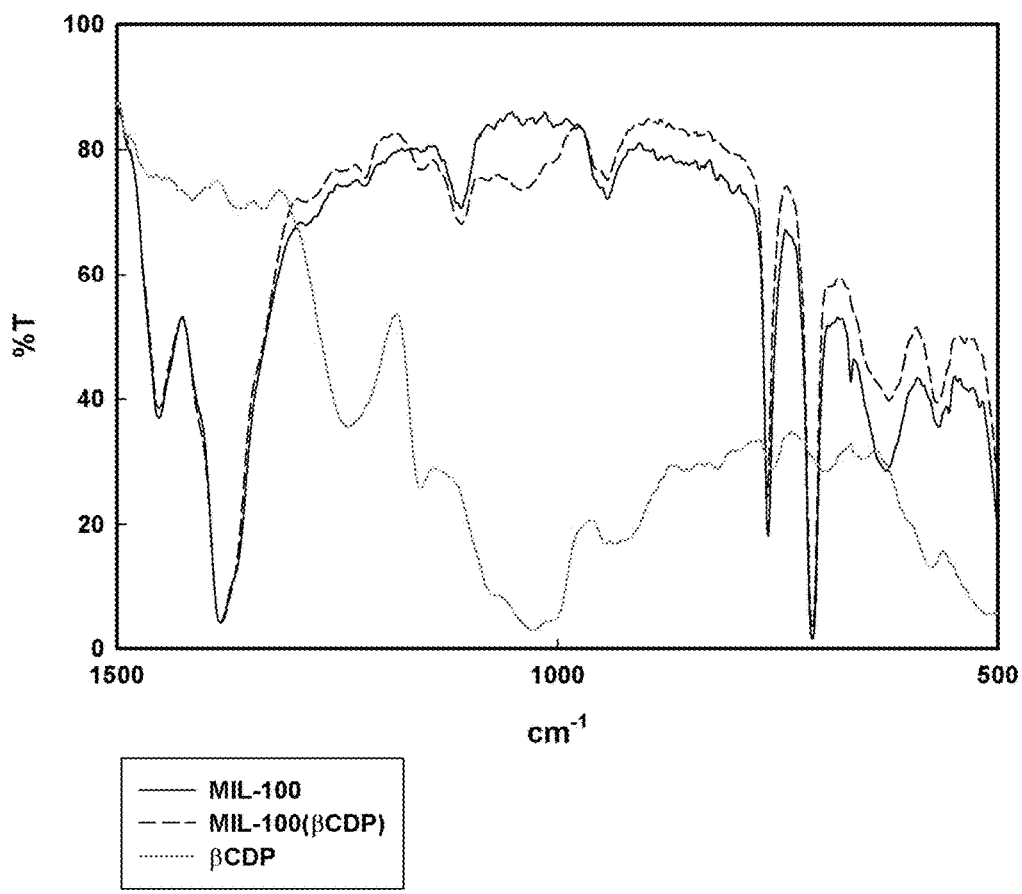
FIG. 4: FT-IR spectrum of βCDP, of MOF MIL-100 and of MOF MIL-100 surface-modified with βCDP.

FT-IR Spectroscopic Analysis 5 mg of MIL-100 was incubated with 1 ml of an aqueous solution of βCDP at 2.5 mg/ml (weight ratio nanoparticles:βCDP=1:0.5) for 24 h with stirring at room temperature. At the end of incubation, the nanoparticles were recovered by centrifugation at 5600×g for 10 min, washed three times with 1 ml of water, dried for 8 h at 100° C. and finally characterized by FT-IR. After modification, the spectrum of MIL-100 shows a typical signature of βCDP at about 1050 $cm^{-1}$, absent in the unmodified sample, which might be connected with the presence of phosphate groups bound to the nanoparticles. These results confirm effective functionalization of the MIL-100 nanoparticles with βCDP by simple incubation (FIG. 4).

Elemental Analysis 20 mg of MIL-100 nanoMOF was incubated for 15 min, 1 h or 24 h with 4 ml of an aqueous solution of βCDP 2.5 mg/ml (weight ratio nanoparticles:βCDP=1:0.5) with stirring, at room temperature. After incubation, the nanoparticles were recovered by centrifugation at 5600×g for 10 min, washed twice with 4 ml of water and stored at 100° C. until the time for analysis. The percentage by weight of βCDP bound to the MIL-100 (βCDP % w/w) was calculated on the basis of the content of phosphorus in the modified sample (P % w/w$_{MIL-100(\beta CDP)}$) and βCDP (P % w/w$_{\beta CDP}$) from the following formula:

$$\beta CDP \ \% \ w/w = \frac{P \ \% \ w/w(MIL-100(\beta CDP))}{P \ \% \ w/w(\beta \ CDP)} \times 100$$

Figure 5:
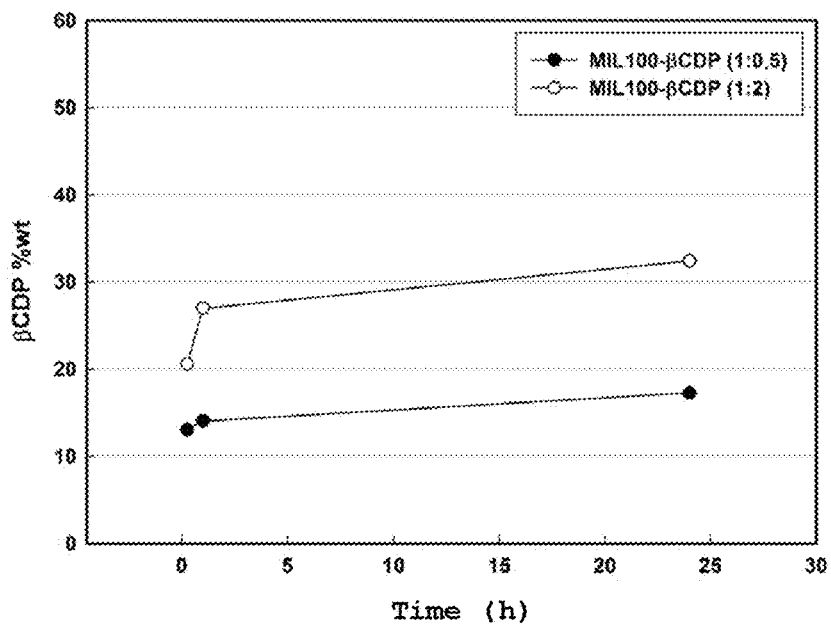
FIG. 5: Kinetics of modification of MIL-100 with βCDP with two different weight ratios of nanoparticles/βCDP: weight ratio of 1:0.5 or 1:2 (solid line and dotted line respectively).

The results obtained showed rapid kinetics of interaction between βCDP and MIL-100. The major portion of the cyclodextrins is already associated with the nanoparticles after only 15 min of incubation. More precisely, the percentage by weight of βCDP was 13-14 and 17.3% respectively after 15 min, 1 h and 24 h of incubation (FIG. 5).

Moreover, the ratio of the percentage by weight of Na to that of phosphorus was analyzed:

$$\frac{Na \ \% \ w/w}{P \ \% \ w/w}$$

It was observed that: a) in the MIL-100 that does not contain sodium, this ratio is equal to 0; b) in βCDP it is 0.74, which corresponds exactly to the expected value based on the molecular formula ($C_{42}H_{70}O_{47}P_4Na_4$) and c) in the MIL-100s modified with βCDP, the ratio shows a definite decrease (about 0.09), indicating that most of the phosphate groups are probably coordinated with the nanoparticles.

Finally, the experiment was repeated in the presence of an excess of βCDP (weight ratio MIL-100:βCDP=1:2), and it was found that in this case the content by weight of βCDP reaches 32.4% after 24 h of incubation (FIG. 5), which may therefore be regarded as the maximum level of association.

Figure 6:
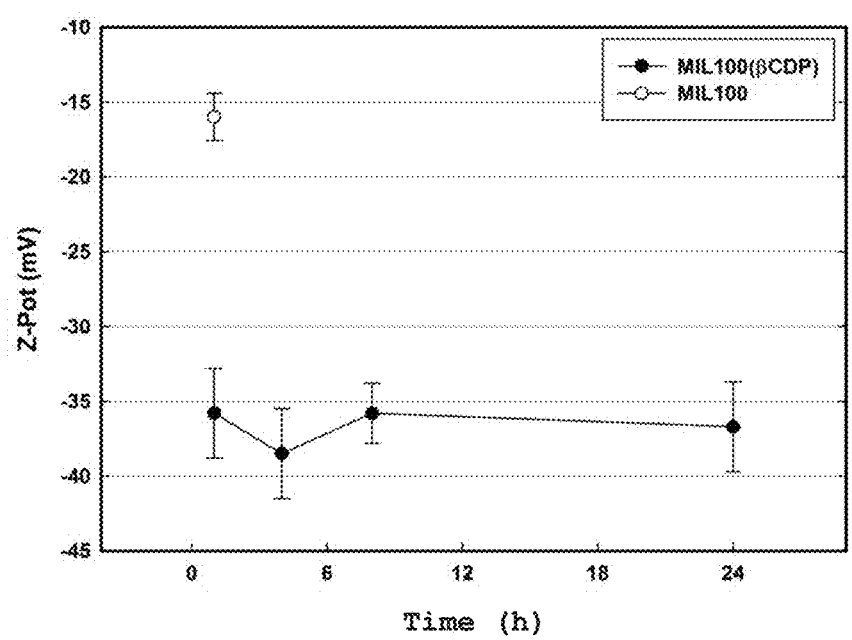
FIG. 6: Representation of the ζ potential of the modified and unmodified MIL-100 nanoparticles as a function of their incubation time.

Analysis of ζ Potential 2 mg of MIL-100 was incubated with 500 µl of an aqueous solution of βCDP 2 mg/ml for different incubation times (1 h, 4 h, 8 h, 24 h), with stirring, at room temperature. 2 mg of unmodified nanoparticles, used as control, were incubated with 500 µl of water. At the end of incubation, the nanoparticles were recovered by centrifugation at 5600×g for 10 min, washed twice with water, and resuspended in 0.5 mM KCl solution. The surface charge of MIL-100 was analyzed by measurements of ζ potential (Zetasizer Nano 6.12, Malvern Instruments Ltd., UK). The results showed that the surface charge of nanoparticles becomes much more negative after modification with βCDP, decreasing from −12 (±3) mV in the unmodified sample, to −35 (±3.5) mV. These results confirm the interaction of βCDP with the surface of MIL-100 through the presence of the phosphate groups, which make the surface charge more negative. Moreover, this interaction was very rapid and, after only 1 h of incubation, the ζ potential has already reached its maximum value (FIG. 6).

XPS Analysis 2 mg of MIL-100 was incubated with 500 µl of an aqueous solution of βCDP 2 mg/ml (weight ratio nanoparticles/βCDP=1:0.5) for 3 h at room temperature, with stirring. 2 mg of unmodified nanoparticles, used as control, were incubated with 500 µl of water. At the end of incubation, the nanoparticles were recovered by centrifugation at 5600×g for 10 min, washed 3 times with water and resuspended in 100 µl of deionized water. 10 µl of these suspensions was deposited on a copper film, left to dry in the air and analyzed by XPS.

The results showed a significant increase in the ratio of the atomic percentage of C to that of iron (C at %/Fe at %) after modification with βCDP (Table 2). In the MIL-100s, the presence of C is only associated with the trimesate and the excess observed after modification is therefore in agreement with the presence of βCDP on the surface of the nanoparticles. In particular, there is 4.6 C belonging to the βCDP bound to each Fe atom, which corresponds to about 1 βCDP for every 9.1 Fe atoms, since each molecule of βCDP contains 42 C. The same reasoning may be applied, taking into account the atomic percentage of oxygen. In this case, we observed an increase in the ratio of the atomic percentage of O to that of iron (O/Fe at %) after modification with the βCDPs. In particular, we calculated the presence of about 4.2 O bound to the βCDP per iron atom, which is equivalent to the presence of one molecule of βCDP for every 11.2 iron atoms, since each molecule of βCDP contains 47 O. These results are in agreement with that obtained previously from the atomic percentage of C. We may therefore conclude that there is about 1 molecule βCDP for every 10 Fe atoms.

Finally, we repeated the experiment in the presence of an excess of βCDP (weight ratio nanoparticles:βCDP=1:2). With this same strategy, we calculated that the highest level of association corresponds effectively to one molecule of βCDP per 8 Fe atoms.

Finally, we repeated the experiment in the presence of an excess of βCDP (weight ratio nanoparticles:βCDP=1:2). With this same strategy, we calculated that the highest level of association corresponds effectively to one molecule of βCDP to 8 iron atoms.

These results indicate that the βCDPs are capable of interacting with the surface of MIL-100, forming an outer corona. However, our ultimate aim was to demonstrate that this outer corona would not alter the porosity of the MIL-100s and their capacity for encapsulation of medicaments.

TABLE 2

Atomic composition of the MIL-100 nanoparticles, unmodified and modified with βCDPs

|  | C %/Fe % | O %/Fe | P %/Fe |
|---|---|---|---|
| nanoMOF | 7.5 | 4.5 | 0 |
| nanoMOF(βCDP) (1:0.5) | 12.1 | 8.7 | 0.5 |
| nanoMOF(βCDP) (1:2) | 13.1 | 9.7 | 0.7 |

Nitrogen Adsorption Porosimetry of the MIL-100s after Modification with βCDP or MeO-PEG-NH$_2$ To answer this question, we studied the porosity of MIL-100 before and after modification with βCDP. 30 mg of nanoparticles were incubated with 6 mL of an aqueous solution of βCDP 2.5 mg/ml (weight ratio nanoparticles:βCDP=1:0.5), for 24 h with stirring. After incubation, the nanoparticles were recovered by centrifugation at 5600×g for 10 min and dried for 6 h at 100° C. The porosity of the materials was analyzed by nitrogen adsorption at 77K (Belsorp Mini, Bell, Japan). The results showed that, taking into account the increase in weight connected with grafting the βCDPs on the surface of the particles of MIL-100, the porosity (pore specific surface and volume) of the particles remains exactly the same after modification, thus demonstrating that βCDP, owing to its bulky structure, is not adsorbed into the pores of nanoparticles and only interacts with the surface of nanoparticles, forming an outer corona that does not affect the porosity of the materials and their capacity for encapsulation of medicaments (FIG. 7 A).

Figure 7:
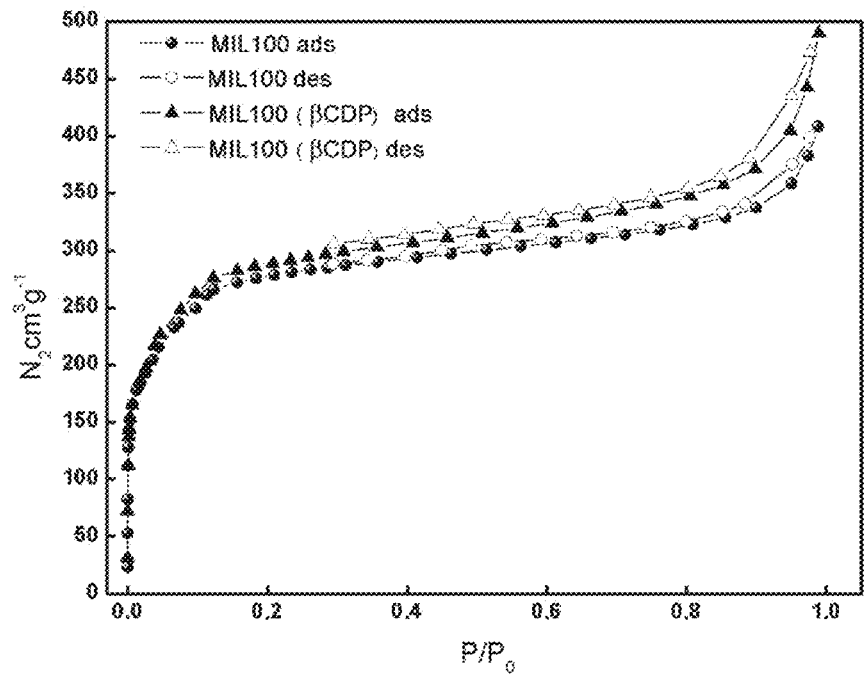
FIG. 7 A) and B): Isotherms of adsorption and desorption of nitrogen at 77K for MIL-100 before and after surface modification with βCDP (A) or Meo-PEG-$NH_2$ (B).
Figure 7:
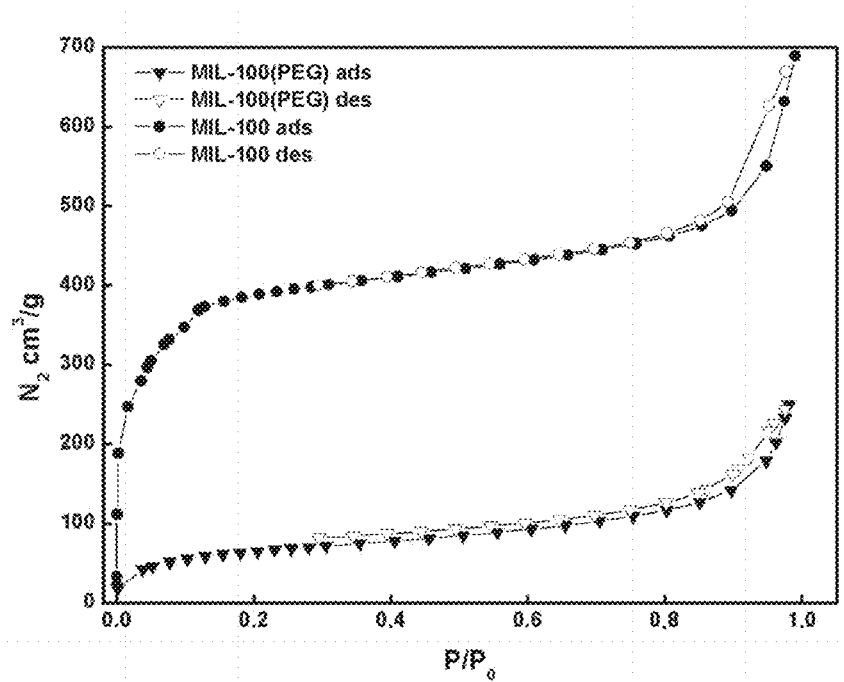
Figure 8A:
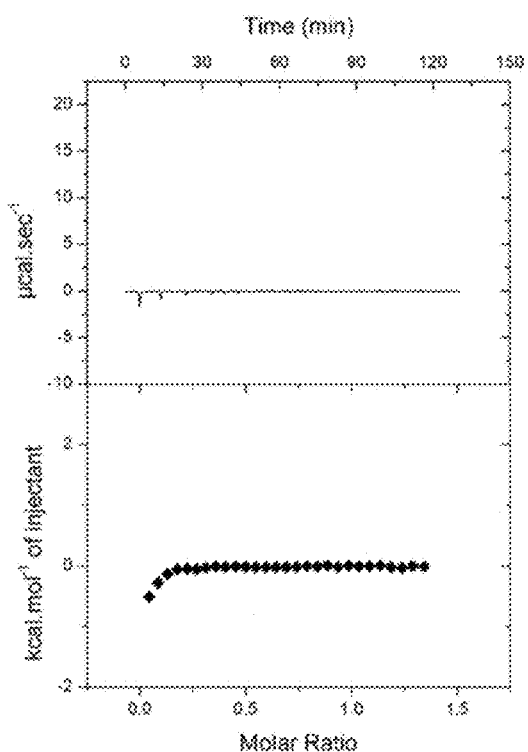
FIG. 8: Interaction between the MIL-100 nanoparticles and βCD MIL-100 (A) or βCDPMIL-100 (B) obtained by ITC characterization.
Figure 8B:
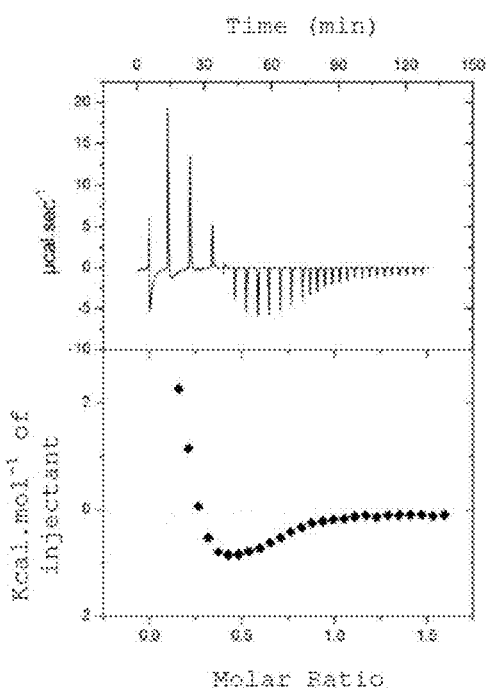

Conversely, studying the porosity of the MIL-100s before and after incubation with Meo-PEG-NH$_2$ (5000 Da), we observed that the porosity of the nanoparticles decreases considerably after modification (FIG. 7 B). These results demonstrate that it is not possible to modify the surface of the MIL-100s with PEG directly without altering their porosity and capacity for encapsulation, probably because the linear chain of the PEG can easily penetrate into the micropore windows of the nanoparticles and thus be adsorbed into the pores.

In this study, 30 mg of MIL-100 was incubated with 2 mL of an aqueous solution of PEG 5 mg/ml, for 3 h at 30° C., with stirring. At the end of incubation, the nanoparticles were recovered by centrifugation at 5600×g for 10 min and dried for 6 h at 100°. The porosity of the materials was analyzed by nitrogen adsorption porosimetry at 77 K.

Example 3

Syntheses of Branched PEG 30 mg of MIL 100 nanoparticles were incubated with 2 mL of an aqueous solution of star PEG 0.5 mg/mL (Amino-dPEG™(4)-[dPEG™(12)-OMe]$_3$, $C_{99}H_{197}N_5O_{47}$, 2209.63 g/mol, Iris Biotech, Germany) at room temperature with two-dimensional stirring, for 2 minutes. At the end of incubation, the nanoparticles were recovered by centrifugation at 5600×g for 10 min, followed by two washings with water. The PEG was determined in the supernatants recovered after the first centrifugation by a colorimetric method (ref. Baleaux [33]). Only 1 wt % of PEG remains in the supernatant, which shows that practically all the PEG (99 wt %) interacts with the nanoparticles. The porosity of the dried nanoparticles was analyzed by nitrogen adsorption at 77 K. The BET specific surface changes from 1400 to 1225 m$^2$/g, thus showing that the star PEG also penetrates into the pores, just like the linear PEG (cf. below). Moreover, the surface charge does not change before and after functionalization with the branched PEG (ξpotential ~−1-25 mV).

It should be noted that this penetration into the pores is extremely rapid, taking about two minutes. This example tends to prove that for this material with "large" windows, star PEGs with a larger number of branchings (>4) would be necessary to avoid penetration into the pores.

Linear PEGs with Different End Groups 30 mg of MIL 100 nanoparticles were incubated at room temperature with two-dimensional stirring for 2 minutes with 1 mL of ethanol and 1 mL of an aqueous solution of linear PEG 0.5 mg/mL, bearing, at each chain end:
- a methoxy group and a carboxyl group (alpha-methoxy-omega-carboxylic acid poly(ethylene glycol), 5000 Da, Iris Biotech, Germany, MeO-PEG-COOH)
- a methoxy group and an amino group (alpha-methoxy-omega-amino poly(ethylene glycol), 5000 Da, Iris Biotech, Germany, MeO-PEG-NH$_2$)
- an amino group and a carboxyl group (alpha-amino-omega-carboxy poly(ethylene glycol) hydrochloride, 5000 Da, Iris Biotech, Germany, NH$_2$—PEG-COOH.HCl)
- star PEG (Amino-dPEG™(4)-[dPEG™(12)-OMe]$_3$, C$_{99}$H$_{197}$N$_5$O$_{47}$, 2209.63 g/mol, Iris Biotech, Germany
- a bisphosphonate group (PEG-alendronate; synthesis in the laboratory):

Step 1: Synthesis of
4-amino-1-hydroxybutylidene)bisphosphonic acid
(alendronate)

4-Aminobutyric acid (20 g, 0.19 mol) and one equivalent of phosphorous acid H$_3$PO$_3$ (16 g, 0.19) were put in a 250-mL four-necked flask equipped with a mechanical stirrer, a thermometer, and a dropping funnel. They were dissolved in a minimum of methanesulfonic acid and then the reaction mixture was heated to 65° C.

Maintaining the temperature at 65° C., two equivalents of phosphorus trichloride PCl$_3$ (35 mL, 0.40 mol) were added dropwise in 20 minutes. The reaction mixture was then stirred at 65° C. overnight. Next, the reaction mixture was quenched, using iced distilled water, and then the mixture obtained was transferred to a 500-mL three-necked flask. The mixture was refluxed for 5 hours.

The reaction mixture was brought back to room temperature using an ice bath. Using an aqueous solution of NaOH at 50% (by weight), the pH was adjusted to 4.3 to promote precipitation of the bisphosphonic acid. The precipitate was filtered and dried under vacuum. Purification of the alendronate consists of performing several washings with anhydrous methanol until the methanesulfonic acid has been removed. The precipitate was then dried overnight in a heated desiccator (at 40° C.)

Yield: 82%
IR (cm$^{-1}$): 1524, 1473, 1168, 1073, 913 cm$^{-1}$
$^1$H NMR (500 MHz, D$_2$O): 2.93 (m, 2H), 1.88 (m, 4H)
$^{31}$P NMR {1H} (80.9 MHz, H$_3$PO$_4$/D$_2$O): 18.5 (s).

Step 2: Alendronate-PEG5000-COOH Coupling
(PEG-alendronate)

In a tablet bottle, 1 equivalent of mPEG5000-COOH (150 mg, 3.10$^{-5}$ mol) was dissolved in 5 mL of water, with magnetic stirring. The coupling agents EDC (45.5 mg, 3.10$^{-5}$ mol) and NHS (33.7 mg, 3.10$^{-5}$ mol) were added to the reaction mixture. The solution was stirred for one hour in an incubator at 37° C. The pH was 4.5. The alendronate (7.8 mg, 0.9 eq) was dissolved in 1 mL of water. The pH was adjusted to 10 with a few drops of triethylamine. The solution was then added dropwise to the solution of activated PEG, and the pH was adjusted to 10 once again.

The solution was stirred for 24 hours in the incubator at 37° C.

Purification consisted of evaporating the water. The crystals were dissolved in a minimum of water (200μ) and then the desired product was precipitated by adding 20 mL of acetone. The white precipitate was filtered and then dried in the stove under vacuum at 40° C. overnight.

Mass obtained: 110 mg
Yield: 68%
$^{31}$P NMR {1H} (80.9 MHz, H$_3$PO$_4$/D$_2$O): 17.96 (s).

At the end of incubation, the nanoparticles were recovered by centrifugation at 5600×g for 10 min, followed by two washings with water. The PEG was determined in the supernatants recovered after the first centrifugation by a colorimetric method (ref. Baleaux [33]). Only 1 to 2 wt % of PEG remains in the supernatant, which shows that practically all the PEG (98-99 wt %) interacts with the nanoparticles. The porosity of the dried nanoparticles was analyzed by nitrogen adsorption at 77 K. The BET specific surface decreased from 1400 to 1050, 1120, 1160, 1270 and 1320 m$^2$/g in the case of the MeO-PEG-COOH, MeO-PEG-NH$_2$, NH$_2$-PEG-COOH, and star PEG and PEG-alendronate, respectively. This demonstrates that these linear PEGs functionalized at chain end penetrate rapidly into the pores of the MIL 100 nanoparticles. Moreover, the surface charge has not changed after functionalization with the branched PEG (ξ potential ~−25 mV).

Example 4

Figure 14:
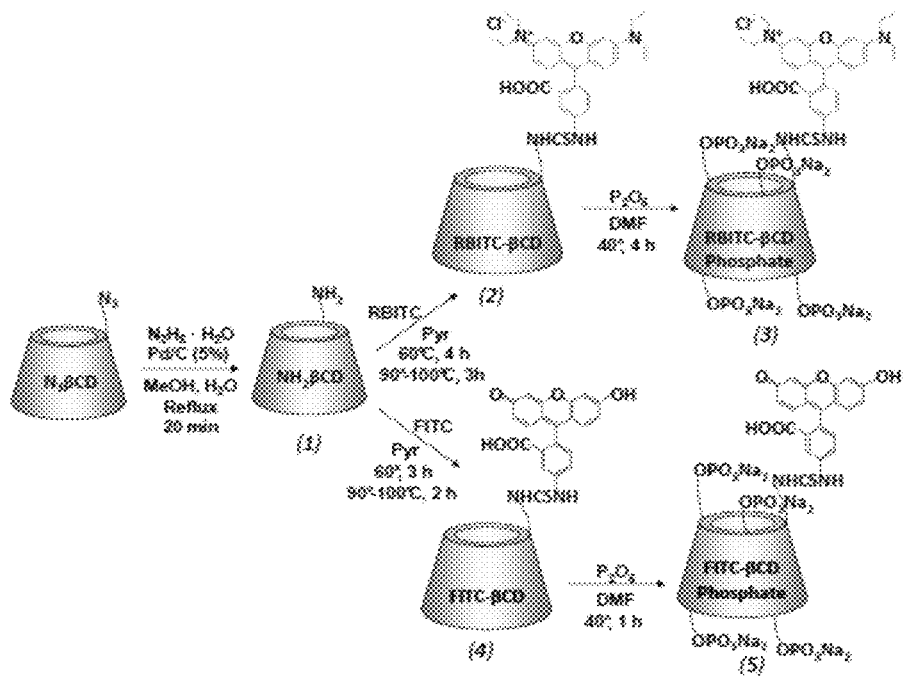
FIG. 14: Illustration of the steps used for synthesis of the fluorescent derivatives of the monomer of β-cyclodextrin phosphate from example 4.
Figure 15:
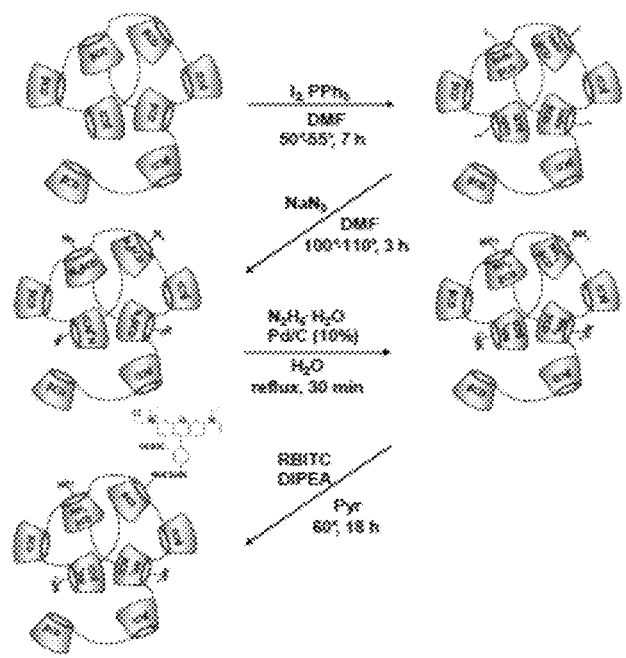
FIG. 15: Illustration of the synthesis steps of the fluorescent derivatives of poly-βCD phosphate from example 5.

Synthesis of Fluorescent Derivatives of the
β-cyclodextrin Phosphate Monomer i) β-cyclodextrin Phosphate Rhodamine BITC (βCDP-RBITC)
ii) β-cyclodextrin Phosphate FITC (βCDP-FITC)
The synthesis steps used are illustrated in FIG. 14.

6-monoamino-6-monodeoxy-βCD (Free Base) (1)

11.60 g (0.01 mol) of 6-monoazido-6-monodeoxy-βCD was dispersed cold, with stirring, in H$_2$O:MeOH-4:1 mixture (100 mL). First a suspension of Pd/C (0.58 g, 5% Pd content in 3 mL H$_2$O), and then hydrazine monohydrate (5 g, 5 mL, 0.1 mol) were added and heated under reflux. After 20 min with stirring under reflux, the mixture was cooled to about 50° C., filtered to remove the catalyst and washed three times with water (15 mL). After evaporation of the solvents, the crude product was precipitated in an aqueous solution (50 mL) of NH$_4$OH 25% (2 mL). The crystals were filtered, washed three times with MeOH (10 mL) and dried at 60° C., under reduced pressure (10 mbar) overnight in the presence of P$_2$O$_5$ and KOH. The product (1) obtained in the form of white crystals (10.2 g, 90%) was free from nitride and hydrazine, it was characterized by IR and it was stored under vacuum in the presence of KOH.

(1): m.p.: 203-205° C. (dec.). R$_f$: 0.26-0.29.

IR (KBr) ν/cm$^{-1}$: disappearance of the azide band (2105), 3428 (O—H), 2928 (C—H), 1080, 1029 (C—O—C).

$^1$H-NMR (DMSO-d$_6$): δ=5.78-5.63 (m, 14H), 4.90-4.85 (m, 7H), 4.50-4.45 (m, 6H), 3.66-3.54 (m, 28H), 3.42-3.24 (overlap with HDO, m, 16H).

$^{13}$C-NMR (125 MHz, DMSO-d$_6$): δ=101.8, 82.9, 81.6, 81.5, 73.0, 72.3, 72.1, 59.9.

6-monodeoxy-6-mono[(5/6)-rhodaminylthioreido]-βCD hydrochloride (2)

Freshly prepared compound (1) (227 mg, 0.2 mmol) was dispersed at room temperature in 5 ml of pyridine and 113 mg (0.21 mmol) of rhodamine B isothiocyanate (RBITC) were added. The mixture was heated at 60° C. with stirring. After 4 h, the temperature was raised to 90-100° C. and 54 mg (0.1 mmol) of rhodamine B isothiocyanate was added. After 3 h with stirring, the reaction mixture was brought back to room temperature and was precipitated by adding 20 ml of acetone. The crude product was filtered, washed twice with acetone (1 mL), dispersed in water (50 mL) and extracted three times with ethyl acetate presaturated with water (50 mL) to remove the residual rhodamine B isothiocyanate. The aqueous phase was evaporated at 60° C. under reduced pressure and the violet solid obtained was dispersed in 10 ml of water. Hydrochloric acid (0.1 M) was added until a clear solution was obtained (pH=4-5). After lyophilization, the product (2) was recovered in the form of violet powder (244 mg, 74%).

(2): m.p.: 214°-215° C. (dec.). R$_f$: 0.52-0.54, 0.82-0.84 (RBITC).

IR (KBr) ν/cm$^{-1}$: 3310 (O—H), 2968 (C—H), 2928 (C—H), 1708 (C═O), 1617 (C═C), 1154 (C—O), 944 (C—O), 683.

$^1$H-NMR (DMSO-d$_6$): δ=0.90-1.30 (t, 12H, methyl-H), 3.10-3.50 (m, 14H, H-2,4), 3.50-3.78 (m, 28H, H-3,5,6), 3.78-4.10 (m, 8H, methylene-H), 4.51 (s broad, 6H, OH-6), 4.84 (s, 6H, H-1), 4.96 (s, 1H, H-1'), 5.74 (s broad, 14H, OH-2,3), 6.80-7.00 (m, 6H, aromatic-H), 7.00-7.18 (m, 3H, aromatic-H), 7.23 (s), 7.37 (m), 7.60-7.75 (m), 7.90 (s broad), 8.00-8.08 (s broad), 8.08-8.25 (m), 8.39 (s broad), 8.52 (s broad), 8.56 (d, J=3.4 Hz), 8.74 (d, J=4.7 Hz), 11.00 (s broad, 1H, OH-carboxylic)

$^{13}$C-NMR (DMSO-d$_6$): δ=12.25, 45.12, 59.71, 71.83, 72.23, 72.85, 81.31, 95.63, 101.10-101.72 (s broad), 112.00-115.00 (s broad), 125.40, 129.00-130.93 (s broad), 141.40, 154.78, 156.88, 165.40.

6-monodeoxy-6-mono[(5/6)-rhodaminylthioreido]-βCD phosphate sodium salt (3)

P$_2$O$_5$ was added (200 mg, 1.4 mmol) to anhydrous N-dimethylformamide (DMF, 3 mL) and the mixture was dispersed by ultrasonication until a clear solution was obtained. Compound (2) (235 mg, 0.14 mmol) was added to the solution at room temperature. The reaction mixture was heated to 40° C., stirred for 4 h and then cooled to room temperature. 20 ml of water was added and the solution obtained was dialyzed for 1 day. The solution was neutralized (pH ~7) with NaOH (1 M) and dialyzed several times (1 day). The solution pH was adjusted to 7-8 with NaOH (1 M) and the product was extracted four times with ethyl acetate presaturated with water (30 mL). The water was evaporated at 60° C. under reduced pressure and the solid obtained was dispersed in 20 ml of water, dialyzed overnight and finally lyophilized (3) in the form of violet powder (229 mg, 84%).

(3): m.p.: 229°-232° C. (dec.). R$_f$: 0.0, 0.82-0.84 (RBITC). IR (KBr) ν/cm$^{-1}$: 3390 (O—H), 1647 (C═C), 1594, 1467, 1414, 1348 (P═O), 921, 685, 517.

6-monodeoxy-6-mono[(5/6)-fluoresceinylthioreido]-βCD hydrochloride (4)

Freshly prepared compound (1) (227 mg, 0.2 mmol) was dispersed in 5 ml of pyridine (5 mL) at room temperature, 82 mg (0.21 mmol) of fluorescein isothiocyanate (FITC) was added and the reaction mixture was heated to 60° C. After stirring for 3 h, the temperature was raised to 90-100° C. and 39 mg (0.1 mmol) of fluorescein isothiocyanate was added. After stirring for 2 h, the reaction mixture was cooled to room temperature and was precipitated by adding 20 ml of acetone. The crude product was filtered, washed twice with acetone (1 mL), dispersed in water (50 mL) and extracted three times with ethyl acetate presaturated with water (50 mL) to remove the residual fluorescein isothiocyanate. The aqueous phase was evaporated at 60° C. under reduced pressure. The yellowish-orange solid was dispersed in water (10 mL) and hydrochloric acid (0.1 M) was added until a clear solution was obtained (pH=4-5). After lyophilization, product (4) was recovered in the form of yellow powder (256 mg, 85%).

(4): m.p.: 222-225 (dec.). R$_f$: 0.48-0.51, 0.79-0.83 (FITC).

IR (KBr) ν/cm$^{-1}$: 3307 (O—H), 2930 (C—H), 1746 (C-OLacton), 1614 (C═C), 1540, 1505, 1453, 1402, 1365, 1328, 1259, 1154, 945, 850, 593.

$^1$H-NMR (DMSO-d6): δ=3.10-3.44 (m, 14H, H-2,4), 3.50-3.78 (m, 28H, H-3,5,6), 4.23-4.65 (m, 6H, OH-6), 4.83 (d, 6H, H-1, J=2.9 Hz), 4.90 (s broad, 1H, H-1'), 5.55-6.00 (m, 14H, OH-2,3), 6.45-6.72 (m, 6H, Aromatic-H), 7.18 (d, 1H, H, J=7.9 Hz), 7.78 (d, 1H, J=7.4 Hz), 7.90 (s broad, 1H), 10.12 (s broad, 2H, OH-phenolic and carboxylic).

$^{13}$C-NMR (DMSO-d$_6$): δ=59.59, 71.83, 72.34, 72.90, 81.41, 99.26, 101.80, 102.10, 109.68, 118.17, 127.37, 128.90, 129.20, 131.30, 152.71, 167.97, 169.51, 180.30.

6-monodeoxy-6-mono[(5/6)-fluoresceinylthioreido]-βCD phosphate sodium salt (5)

P$_2$O$_5$ was added (200 mg, 1.4 mmol) to 3 ml of anhydrous N-dimethylformamide (DMF) and the mixture was dispersed by ultrasonication until a clear solution was obtained. Compound (4) (213 mg, 0.14 mmol) was added to the solution at room temperature and the reaction mixture was heated at 40° C. with stirring for 1 h. The crude product was cooled to room temperature, 20 mL of water was added and the solution obtained was dialyzed for 1 day. The solution was neutralized (pH ~7) with NaOH (1 M) and dialyzed several times (1 day). The solution pH was adjusted to 7-8 with NaOH (1 M) and the product was extracted four times with ethyl acetate presaturated with water (30 mL). The water was evaporated at 60° C. under reduced pressure. The solid obtained was dispersed in 20 ml of water, dialyzed overnight and then lyophilized (5) until a yellow powder was obtained (223 mg, 84%).

(5): m.p.: 268-270 (dec.). $R_f$: 0.0-0.0, 0.79-0.83 (FITC).
IR (KBr) v/cm$^{-1}$: 3399 (O—H), 2924 (C—H), 1750 (C=O), 1639 (C=O), 1611, 1498, 1470, 1428, 1253 (P=O), 1158, 1080, 1034, 918, 525.
$^{31}$P-NMR (D$_2$O): δ=−22.46 (s broad), −21.49 (s), −10.70 (s broad), −9.44 (s broad), −8.86 (m), −2.78 (s broad), 0.35 (s broad), 0.86 (s broad).

Example 5

Synthesis of Fluorescent Derivatives of β-cyclodextrin Phosphate Polymer

Figure 16:
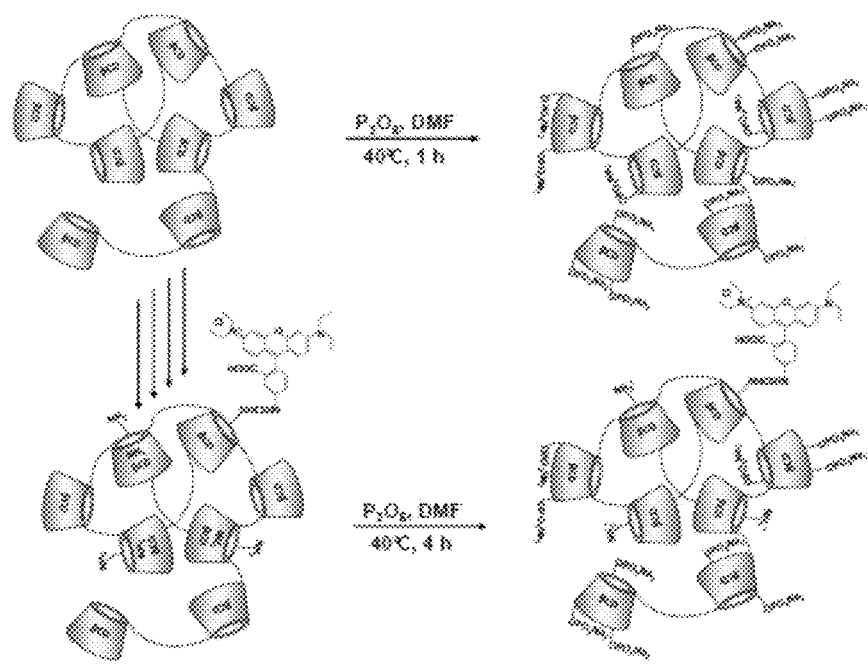
FIG. 16: illustration of the steps of phosphorylation of poly-βCDs from example 5.

The synthesis steps used for preparing the fluorescent derivatives of poly-BCD phosphate are illustrated in FIG. 16.

Note: In the case of FITC, only the last step is different (FITC instead of RBITC, compound (9)).

6-monoazido-6-monodeoxy-poly-βCD (6)

8 mg (0.03 mmol) of PhP$_3$ was dispersed with stirring in 15 ml of anhydrous DMF. 8 mg (0.03 mmol) of I$_2$ was gently added to this solution in the space of 10 min, taking care that the temperature did not exceed 40° C. 2.1 g of poly-BCD was then added, the temperature was raised to 50° C. and the solution was stirred at atmospheric pressure for 7 h. The suspension was cooled to about 50° C., 5 ml of CH$_3$OH was added and the suspension was stirred for 30 min. CH$_3$OH was then removed under reduced pressure and DMF (~2 mL) was added until a solution was obtained. 4 mg (0.062 mmol) of NaN$_3$ was added and the temperature was raised to 100° C. for 3 h. After cooling to room temperature, the solution was dialyzed overnight and was then diluted with 100 mL of H$_2$O. 0.5 g of charcoal was added and the suspension was stirred for 30 min. The charcoal was filtered off, and the reaction product was washed three times with water (15 mL) and filtered. The resultant solution was evaporated to ⅓ of the volume and lyophilization gave product (6) in the form of white powder (1.9 g).
IR v/cm$^{-1}$: 3408, 2926, 2103, 1663, 1437, 1037, 859, 723, 542.
$^1$H-NMR (D$_2$O) δ: 3.0-4.4 (s broad), 4.9-5.3 (s broad).

6-monoamino-6-monodeoxy-poly-βCD (7)

Compound (6) (1.9 g) was dissolved in 15 ml of water. First a suspension of Pd/C (0.18 g, 10% of Pd in 2 mL of H$_2$O), and then hydrazine monohydrate (1 g, 1 mL, 0.02 mol) were added and heated under reflux. After 30 min, with stirring under reflux, the reaction mixture was cooled to room temperature, filtered and finally dialyzed overnight. The solution pH was adjusted to between 5 and 6 with HCl and lyophilization gave product (7) in the form of a white powder (1.8 g).
IR v/cm$^{-1}$: disappearance of the azide band at 2103.

6-monodeoxy-6-mono[(5/6)-rhodaminylthioreido]-poly-βCD (8)

0.8 mg of compound (7) was dissolved in 10 ml of pyridine. 10 mg (10 µL, 0.05 mmol) of DBU and then 6 mg (0.01 mmol) of RBITC were added and the solution was heated at 60° C. for 18 h. The solvent was evaporated under reduced pressure (60° C., 10 mbar). The crude product was dispersed again in 50 ml of water and extracted three times with 100 ml of DCM. The aqueous phase was evaporated and the solid was dispersed again in 50 ml of water and extracted three times with ethyl acetate presaturated with 100 ml of water. The aqueous phase was dialyzed three times and lyophilization gave product (8) in the form of a violet powder (0.6 g).
IR v/cm$^{-1}$: 3391, 2924, 1721, 1649, 1591, 1418, 1339, 1157, 1082, 1033, 858, 757.

6-monodeoxy-6-mono[(5/6)-fluoresceinylthioreido]-poly-βCD (9)

0.8 mg of compound (7) was dispersed in 10 ml of pyridine. 10 mg (10 µL, 0.05 mmol) of DBU and then 4 mg (0.01 mmol) of FITC were added and the temperature was raised to 60° C. for 9 h. The solvent was evaporated under reduced pressure (60° C., 10 mbar), the crude product was dispersed again in 50 ml of water and extracted three times with 100 ml of DCM. The aqueous phase was evaporated and the solid was dispersed again in 50 ml of water and extracted three times with ethyl acetate presaturated with 100 ml of water. The aqueous phase was dialyzed three times and lyophilization gave product (9) in the form of yellow powder (0.7 g).
IR v/cm$^{-1}$: 3402, 2925, 1738, 1653, 1592, 1506, 1465, 1328, 1151, 1110, 1082, 1041, 853.

Figure 17:
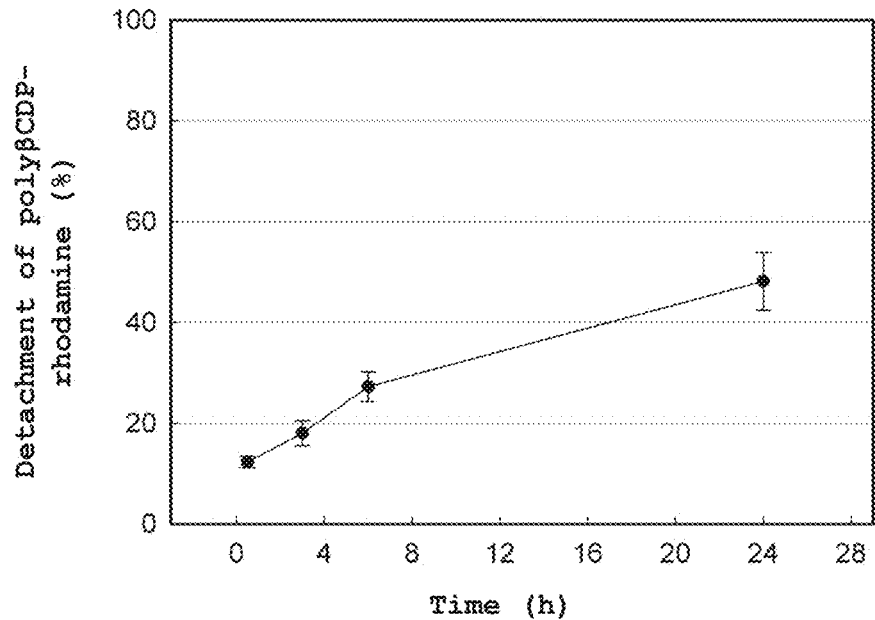
FIG. 17: Kinetics of release of poly-βCDP-rhodamine in PBS medium at 37° C.

The steps for phosphorylation of poly-βCDs are illustrated in FIG. 17.

Note: In the case of FITC, phosphorylation was performed with FITC instead of RBITC (compound (11)).

6-monodeoxy-6-mono[(5/6)-rhodaminylthioreido] poly-βCD phosphate, sodium salt (10)

6-monodeoxy-6-mono[(5/6)-fluoresceinylthioreido]-poly-βCD phosphate, sodium salt (11)

poly-βCD phosphate, sodium salt (12)

Example 6

ITC (Isothermal Titration Calorimetry) Characterization of the MIL-100 MOFs Having an Outer Surface Modified with the β-CDP from Example 2b)

Figure 9:
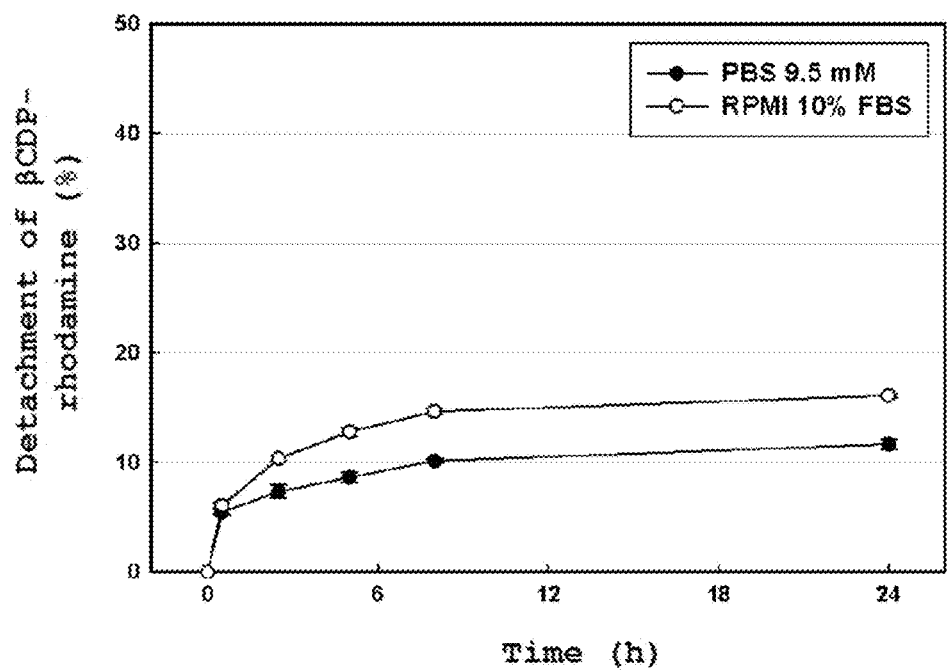
FIG. 9: Kinetics of detachment, release curve of βCDP-rhodamine in PBS or in RPMI supplemented with 10% of bovine serum.

In order to study the nature of the interaction between the βCDPs and the MIL-100s, the thermodynamics of the reaction of surface modification of the nanoparticles by ITC was characterized. Aqueous solutions of βCDP and β cyclodextrin (βCD) at 30 and 14 mg/ml respectively were injected dropwise into 2 ml of an aqueous suspension of MIL-100 1.5 mg/ml. The results showed that the βCDPs interact with the MIL-100s by a complex reaction, involving exothermic and endothermic effects, which could be connected respectively with coordination between phosphate groups and the iron atoms and consequent dehydration of nanoparticles. Conversely, no signal was observed on titrating the solution of βCD. These results indicate that the phosphate groups play a key role in the interaction with MIL-100, probably forming ionocovalent bonds with the iron atoms (FIG. 9).

Example 7

Stability of the Covering Based on βCDP

Once it had been verified that βCDP is capable of interacting effectively with the MIL-100s, the stability of this interaction in physiological conditions was studied. For this, we modified the MIL-100s with βCDP-rhodamine, one molecule of βCD substituted with 3 phosphate groups and one rhodamine-BITC unit. 2 mg of nanoMOF was incubated with 500 µl of an aqueous solution of βCDP-rhodamine, for 24 h with stirring, at room temperature. At the end of incubation, the nanoparticles were recovered by centrifugation at 5600×g for 10 min, and the supernatant was analyzed by spectrofluorimetry in order to define the amount of βCDP-rhodamine bound to the nanoparticles. The results obtained indicate that the amount of βCDP-rhodamine associated with the MIL-100s represents 30.5(±0.1) % w/w. These results are in agreement with those obtained by elemental analysis. The modified nanoparticles were washed with 1 ml of water, to remove the excess βCDP-rhodamine and were finally incubated in 1 ml of PBS (Phosphate Buffered Saline, Lonza) or RPMI 10% FBS (RPMI 1640 GlutaMAX™ with addition of fetal bovine serum 10% (v/v), 100 IU/mL of penicillin-streptomycin), at 37° C., with stirring. After various incubation times (0.5-2, 5-5-8-24 h) the suspension was centrifuged for 10 min at 5600×g, 500 µL of supernatant was taken and was replaced with the same amount of fresh medium. The supernatants were analyzed by spectrofluorimetry, in order to quantify the release of βCDP-rhodamine in the medium. The results showed that only 11.6% of βCDP-rhodamine bound to the nanoparticles is released after 24 h of incubation in PBS and this percentage does not exceed 16.1% in the RPMI 10% SBF (FIG. 9). It may be concluded that the outer corona of βCDP is stable in physiological conditions, probably owing to the cooperative effect between the four phosphate groups that complex the iron.

Effect of the Outer Corona Based on βCDP

Example 8

Figure 10:
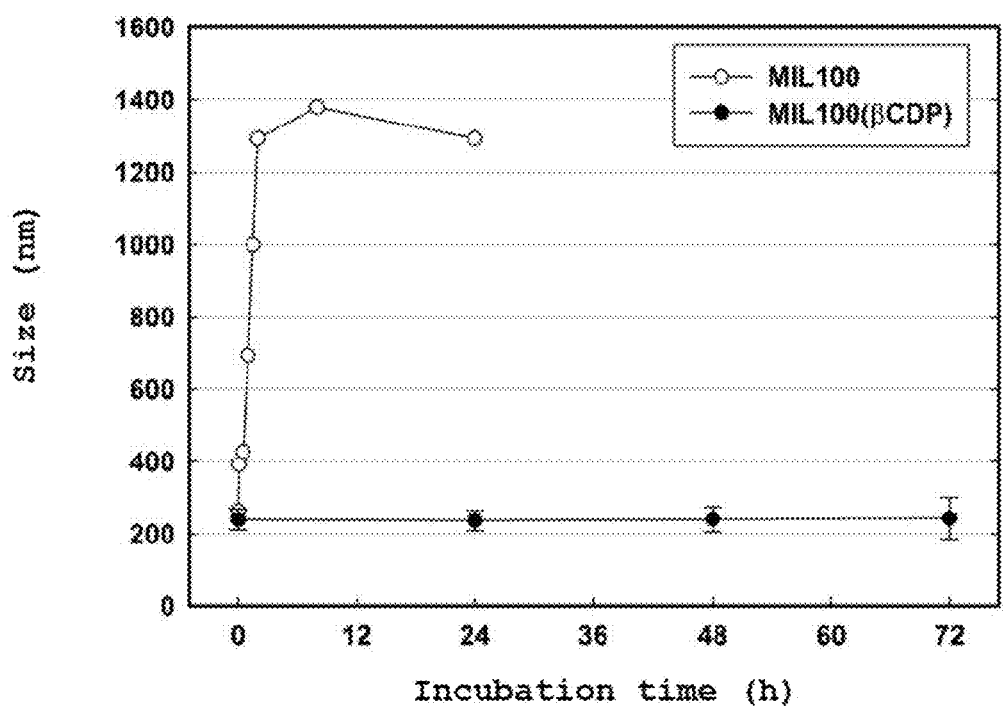
FIG. 10: Aqueous stability of MIL-100, unmodified and modified with β-CDP.

Stability of the MIL-100s in Water 2 mg of MIL-100 was incubated with 500 µl of an aqueous solution of βCDP 2 mg/ml (weight ratio nanoparticles:(CDP=1:0.5) for 24 h at room temperature, with stirring. At the end of incubation, the MIL-100s were recovered by centrifugation at 5600×g for 10 minutes, washed with water and resuspended in 1 ml of water. 2 mg of unmodified MIL-100, used as control, was incubated in 1 ml of water. The size of the nanoparticles was evaluated after different incubation times (1-2-3 days) by DLS (Zetasizer Nano 6.12, Malvern Instruments Ltd., UK). The results showed that, whereas the unmodified nanoparticles form aggregates in water immediately, once modified with βCDP they remain at a constant, small size for 3 days of incubation (FIG. 10). It may be concluded from this that the outer corona of βCDP endows the MIL-100s with good stability in water.

Example 9

Figure 11:
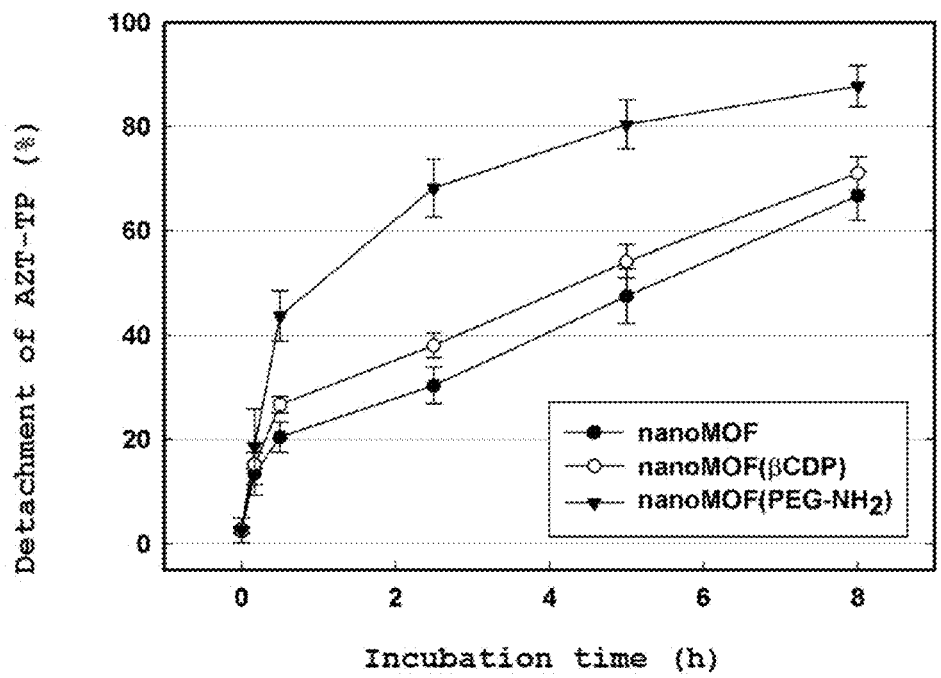
FIG. 11: Kinetics of release of AZT-TP from MIL-100 with surface unmodified, modified with βCDP and modified with MeO-PEG-$NH_2$.
Figure 12:
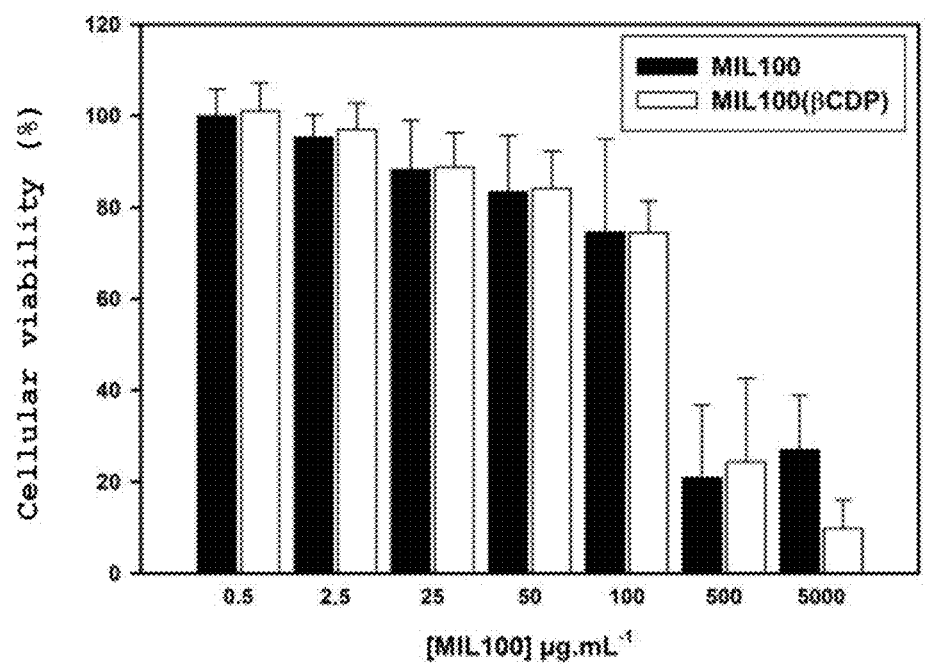
FIG. 12: Evaluation of the cytotoxicity of MIL-100, unmodified and modified with βCDP on the cell line J774.A1.

Use of the MIL-100s for Release of AZT-TP after Modification with βCDP or with MeO-PEG-NH$_2$ 2.5 mg of MIL-100 was incubated with 500 µl of an aqueous solution of azidothymidine triphosphate (AZT-TP, triples) 400 µg/ml, containing 1% of AZT-TP[$^3$H] (AZT-TP-methyl [$^3$H], Moravek), for 24 h at room temperature, with stirring. At the end of incubation, the nanoparticles were recovered by centrifugation at 5600×g for 10 min, and the supernatant was analyzed with a scintillation counter, in order to calculate the level of medicament encapsulated. The nanoparticles were then incubated with 500 µl of an aqueous solution of βCDP 2.5 mg/ml (weight ratio nanoparticles: bCDP=1:0.5), 500 µl of an aqueous solution of MeO-PEG-NH$_2$ 1.67 mg/ml (weight ratio nanoparticles:PEG=1:0.33) or 500 µl of water (control sample), for 3 h at room temperature, with stirring. At the end of incubation, we recovered the nanoparticles by centrifugation at 5600×g for 10 min and we analyzed the supernatant using a scintillation counter to quantify the release of medicaments after surface modification. Finally the nanoparticles were incubated in 1 ml of PBS at 37° C. with stirring. After various incubation times the suspension was centrifuged for 10 min at 5600×g, 500 µl of supernatant was taken and was replaced with an identical amount of fresh medium. The supernatant was analyzed with a scintillation counter in order to evaluate the release of AZT-TP by unmodified nanoparticles, and those modified with βCDP or with MeO-PEG-NH$_2$. The results presented in FIG. 11 show that the surface modification with βCDP does not affect release of the medicament, probably because, as already pointed out, they only interact with the surface of nanoparticles without disturbing the internal porosity of the particles. Conversely, after modification with MeO-PEG-NH$_2$ a "burst effect" (rapid, uncontrolled release) was observed. The linear PEG chains can penetrate into the pores of the MIL-100 and replace the encapsulated molecules of AZT-TP, promoting their release once in PBS.

Example 10

Cytotoxicity of the MIL-100 Nanoparticles, Unmodified and Modified with βCDP

The murine macrophage cell line, J774, (ECACC No. 91051511) was cultured in RPMI 1640 GlutaMAX™ with addition of inactivated fetal bovine serum (10% (v/v)), penicillin (100 IU/mL) and streptomycin (100 µg/mL). The cytotoxicity of the MIL-100s with respect to this line was determined by an MTT assay in 96-well plates ($10^4$ cells per well) after 48 h of incubation with solutions of nanoparticles at different concentrations. The results showed that the MIL-100s do not have any significant cytotoxic effect at high concentrations (100 mM), and the same results were observed after modification with βCDP.

Penetration of the MIL-100s in the J774 Cell Line

For this analysis the MIL-100s were labeled with a fluorophore: adenosine 5'-triphosphate BODIPY-FL (ATP-BODIPY, adenosine 5'-triphosphate, BODIPY® FL, Invitrogen). 1.25 mg of MIL-100 was incubated with 500 µL of an aqueous solution of ATP-BODIPY 10 nmol/ml, for 1 h, with stirring in the dark at room temperature. At the end of incubation, the nanoparticles were recovered by centrifugation at 5600×g for 10 min, and the supernatant was analyzed by spectrofluorimetry in order to quantify the level of absorption of the fluorophore. The nanoparticles were then incubated in 500 µl of water (unmodified sample) or of an aqueous solution of βCDP 1.25 mg/ml, for 1 h with stirring, at room temperature, in the dark. At the end of incubation, the nanoparticles were recovered by centrifugation at 5600×g for 10 min and resuspended in RMPI 10% FBS (fetal bovine serum) to a final concentration of 50 µg/ml. The cells of the J774 line had been cultured beforehand in 24-well plates ($5\times10^4$ cells per well) on a sterile glass cover slip.

Figure 13:
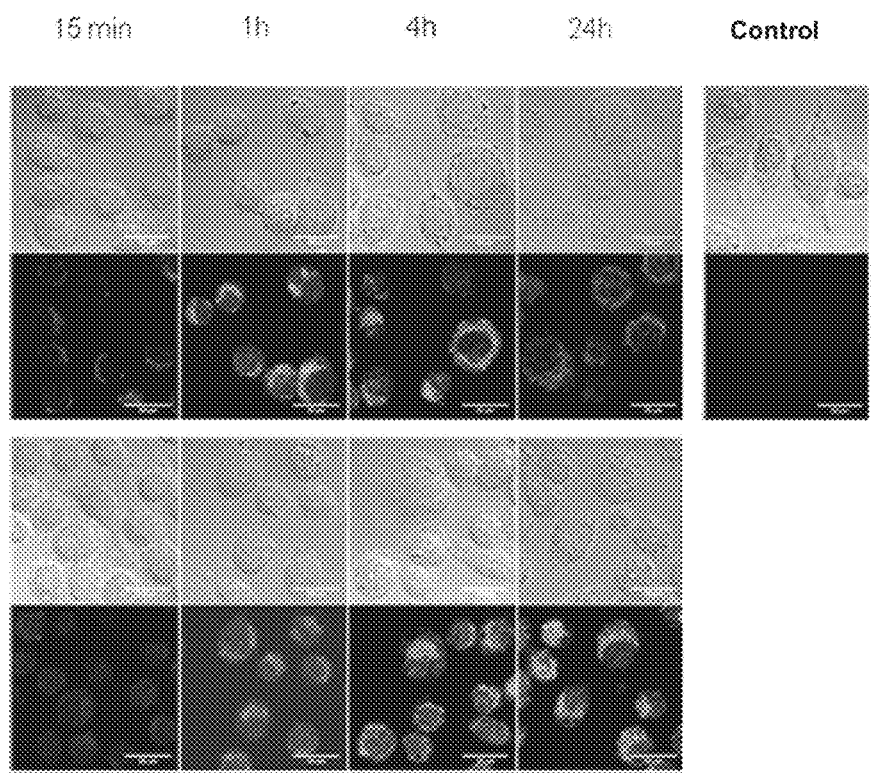
FIG. 13: Images showing the kinetics of penetration of MIL-100, unmodified and modified with βCDP in 774.A1 cells incubated for 24 h with an equivalent of ATP-BODIPY aqueous solution.

After 24 h of incubation in a humidified incubator at 37° C., the culture medium was replaced with 1 ml of the solutions of nanoparticles loaded with ATP-BODIPY (unmodified or surface-modified), or with free ATP-BODIPY. After various incubation times (15 min, 1 h, 4 h, 24 h), the culture medium was aspirated and the cells were fixed. Using CLSM, it was observed that the MIL-100s are very rapidly internalized, probably by phagocytosis, in the cells, after only 15 minutes of incubation. The same behavior was observed in the case of nanoparticles surface-modified with βCDP. In contrast, the free ATP-BODIPY, owing to its hydrophilic character, is not able to pass through the cell membrane and no fluorescence was observed in the cells, which demonstrates the active role of the MIL-100s in internalization of the fluorophore (FIG. 13).

Example 11

Comparative Example of Modification of the Surface of a MOF with a PEG not Functionalized with a Complexing Group According to the Invention: Porosity and Release of Active Ingredients The PEG chains used in the art [2] for functionalizing the surface of the MOFs easily penetrate into the pores of the material, thus leading to a very significant loss of the accessible porosity, and therefore of the capacity for encapsulating the active molecules. Moreover, it had been demonstrated that the PEG chains dislodged the encapsulated active molecules, which were thus released uncontrollably.

Example 12

Comparative Example of Modification of the Surface of a MOF with a Dextran-Biotin not Functionalized with a Complexing Group According to the Invention It was recently demonstrated that coverings based on hydrophobic interactions (dextran-biotin) [2] are not stable in phosphate buffer solutions. These coverings were produced by incubating the MIL 100 nanoparticles with a solution of dextran-biotin (Sigma Aldrich) for one hour, followed by recovery of the nanoparticles by centrifugation at 9500 g and resuspension in water or in PBS. In fact, after half an hour, 30% of the covering had disappeared. After one hour, more than 40% of the dextran had become detached, and 70% after 24 hours. This instability of the covering is not suitable for biomedical applications in vivo.

Example 13

Surface Modification of the MIL-100 Nanoparticles with Poly-βCDP 2 mg of MIL-100 was modified by incubation with 500 µl of an aqueous solution of poly-βCDP-rhodamine (1:10, 1 phosphate/10 cyclodextrins) 2 mg/ml (weight ratio nanoparticles:βCDP=1:0.5), for 24 h with stirring at room temperature. After incubation, we recovered the modified nanoparticles by centrifugation (9500 g, 10 min) and the supernatant was analyzed by spectrofluorimetry in order to define the amount of poly-βCDP-rhodamine associated with the nanoparticles. The results obtained indicate that the amount of βCDP-rhodamine associated with the MIL-100s represents 34(±0.5) % w/w. The modified nanoparticles were washed with 1 ml of water, to remove the excess poly-βCDP-rhodamine, and finally were incubated in 1 ml of PBS (Phosphate Buffered Saline, Lonza) at 37° C., with stirring at a concentration of 2 mg/ml. After various incubation times (0.3-6-24 h) the suspension was centrifuged for 10 min at 9500 g, then 500 µL of supernatant was taken and was replaced with the same amount of fresh medium. The supernatants were analyzed by spectrofluorimetry, in order to quantify the release of poly-βCDP-rhodamine in the medium. The results showed that less than 20% of βCDP-rhodamine bound to the nanoparticles is released after 4 h of incubation in PBS (FIG. 17). It may be concluded that the outer corona of poly-βCDP-rhodamine is stable in physiological conditions, probably owing to the cooperative effect of several phosphate groups that are coordinated with the nanoMOFs.

Example 14

Post-Synthesis Surface Modification of the MIL-100 Nanoparticles with Chitosan

Concept:

The organic-inorganic hybrid nanoparticles (nanoMOF) based on iron trimesate (MIL-100) were modified with chitosan. Chitosan is a polysaccharide of natural origin, obtained by deacetylation of chitin, whose formula is given below (DDA is the degree of deacetylation of chitosan. (DDA: degree of deacetylation)).

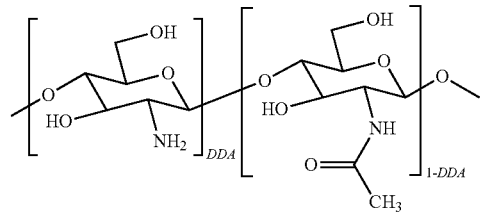

This polymer, consisting of glucosamine units linked together by β(1-4) bonds, offers the advantage that it is biodegradable and biocompatible. Moreover, it has bioadhesive properties. Chitosan, which is insoluble in water, may be dissolved in an acid medium such as 1% solution of acetic acid (AA1%); the amine groups distributed along the polymer chain are then protonated and the polymer is charged positively.

The MIL-100 nanoparticles comprise $Fe^{3+}$ cations as well as COOH groups derived from the trimesic acid used for their synthesis (pKa 3.4).

Figure 18:
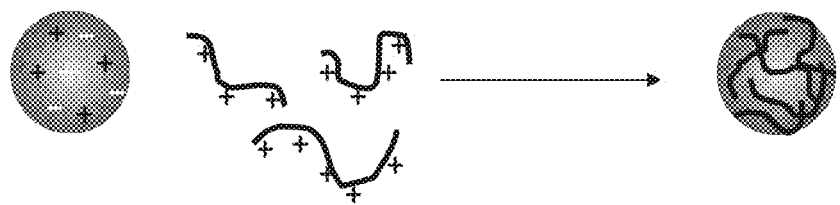
FIG. 18: Schematic representation of the surface modification of the MIL-100 nanoparticles with chitosan via electrostatic interactions.

Surface modification by chitosan is based on the plurality of electrostatic interactions between the polymer and the MIL-100 nanoparticles in AA1% medium (FIG. 18).

The interaction between chitosan and the nanoparticles may be reinforced by adding a salt such as $Na_2SO_4$, which leads to loss of solubility of chitosan and makes it possible to increase the amount of polymer attached to the surface of the nanoparticles.

Methods:

Synthesis of Nanoparticles of Iron Trimesate MIL-100:
Described in Paragraph a of Example 2.

The MIL-100 nanoparticles were obtained by hydrothermal synthesis under microwave irradiation (Mars 5, CEM), by heating an aqueous suspension containing 20 mL of deionized water, 8.97 mmol of $FeCl_3$ ($FeCl_3.6H_2O$, 98% Alfa Aesar) and 4.02 mmol of 1,3,5-benzenetricarboxylic acid (BTC, Sigma Aldrich) for 6 min at 130° C. with stirring.

At the end of reaction, the nanoparticles were recovered by centrifugation at 5600×g for 15 min. Activation of the particles (i.e. extraction of BTC from the pores) was carried out by 6 consecutive washings with 30 mL of absolute ethanol. Once activated, the nanoparticles, of size <300 nm and monodispersed (PDI<0.2), were redispersed in ethanol.

Surface Modification of MIL-100 with Chitosan:

5 mg of MIL-100 was modified by incubation with 500 μL of an aqueous solution of chitosan at 2.5 mg/mL in 1% acetic acid (nanoparticles/chitosan weight ratio=4/1). After homogenization (vortex and ultrasound), the samples were stirred with rotary stirring for 24 h. The nanoparticles were then centrifuged: 16 870×g/20 min/25° C. A uniform pellet was obtained. It was resuspended in 200 μL of AA1% and then the sample was centrifuged again to remove the excess chitosan. The pellet of MIL-100/chitosan nanoparticles was finally taken up in 1 mL of milliQ water.

In certain cases, other nanoparticles/chitosan weight ratios and other incubation times were tested.

Physicochemical Characterization of the MIL-100/Chitosan Nanoparticles:

Average Diameter and Colloidal Stability:

The size of the nanoparticles was measured by quasi-elastic scattering of light (Nanosizer, Malvern, France). Table 3 shows the results obtained on the day of formation of the MIL-100/chitosan nanoparticles (d0) and after 30 days of storage at room temperature (20° C.). The analysis showed a slight increase in average diameter of the nanoparticles after covering with chitosan (213±3 nm vs 178±3 nm). Moreover, the polydispersity index changes from 0.05 for the MIL-100 to 0.26 for the MIL-100/chitosan.

After 30 days of storage, aggregation of the particles was observed in the unmodified sample. However, the MIL-100 nanoparticles covered with chitosan retained their average diameter.

TABLE 3

Average diameter of the MIL-100 nanoparticles with or without chitosan covering

| | d0 | | d30 | |
|---|---|---|---|---|
| | d (nm) | IP | d (nm) | IP |
| MIL 100 | 178 ± 3 | 0.05 | 973 ± 144 | 0.50 |
| MIL 100_Chitosan | 213 ± 3 | 0.26 | 187 ± 3 | 0.11 |

Figure 19:
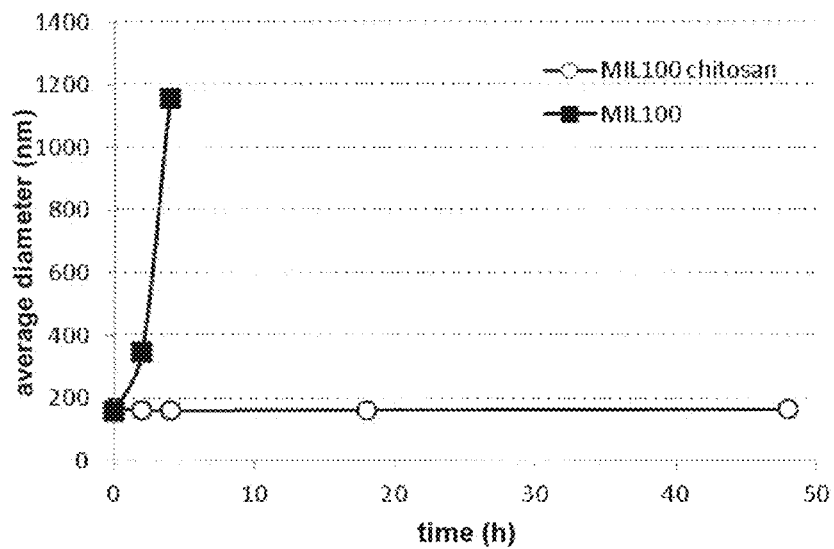
FIG. 19: Evolution of the average diameter of the MIL-100 and MIL-100/chitosan nanoparticles after dilution of the initial suspensions in milliQ water. Dilution factor: 100.

The colloidal stability of the nanoparticles was also evaluated by diluting the suspensions by a factor of 100 in milliQ water and by monitoring the evolution of the average diameter in the diluted sample (FIG. 19).

It was observed that 2 hours after dilution in water, the MIL-100 formed aggregates in the absence of the covering. The average diameter changed from 160 nm to 360 nm after 2 h and reached 1100 nm after 4 h in water. However, in the case of the MIL-100/chitosan, the nanoparticles maintained a constant diameter over time, close to 170 nm.

Stability of the Covering:

MIL-100/chitosan nanoparticles were prepared using chitosan labeled with rhodamine isothiocyanate (chitosan-RITC) with a MIL-100/chitosan weight ratio: 4/1. After contacting the MIL-100 and the chitosan solution for 1, 2 and 24 h, the samples were centrifuged, purified and resuspended in milliQ water as described above (cf. methods). The supernatants obtained from centrifugation of the samples and from purification were analyzed by spectrofluorimetry. It was shown that the chitosan was associated with the MIL-100 at a level close to 2% w/w.

The nanoparticles labeled with rhodamine-ITC were resuspended in 1 mL of phosphate buffer pH 7.4. After 24 h of incubation at RT in this medium, the samples were centrifuged and the supernatants were analyzed by spectrofluorimetry. The chitosan-RITC was not detected in the supernatants, indicating that the MIL-100/chitosan association was stable in the experimental conditions tested.

XRD

Figure 20:
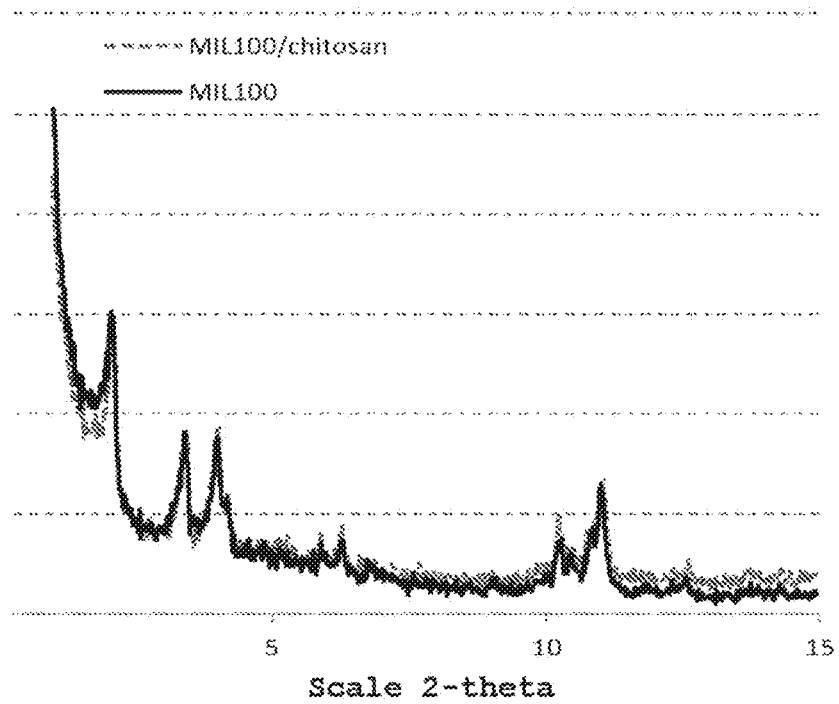
FIG. 20: X-ray diffraction patterns of MIL-100 and chitosan-modified MIL-100.

The MIL-100 nanoparticles, unmodified and chitosan-modified, were dried at 100° C. for 18 h and then their structure was analyzed by X-ray diffraction. The X-ray diffraction analyses showed that the process for modification of the surface of the MIL-100 nanoparticles with chitosan did not alter the crystalline structure of the material (FIG. 20).

Nitrogen Adsorption Porosimetry of the MIL-100s after Modification with Chitosan 30 mg of nanoparticles were incubated with 3 mL of an aqueous solution of chitosan at 2.5 mg/mL (nanoparticles/chitosan weight ratio=4/1). After 24 h of contact, the excess chitosan was removed by centrifugation at 16870×g/20 min/25° C. The nanoparticles were purified as described above and then they were dried at 100° C. for 18 h. A control sample of MIL-100 (without chitosan) was prepared in the same way as the MIL-100/chitosan sample. The porosity of the materials MIL-100 and MIL-100/chitosan was analyzed by nitrogen adsorption at 77K.

The results showed that the specific surface of the MIL-100 nanoparticles was not altered by the chitosan covering. Thus, the MIL-100s showed a Langmuir surface area of 2100 $m^2/g$ whereas the MIL-100/chitosan had a Langmuir surface area equal to 2030 $m^2/g$. This also demonstrates that the chitosan does not block access to the pores and therefore this is consistent with the presence of chitosan only on the surface of the particles.

Encapsulation and Release of AZT-TP

Chitosan-modified nanoparticles were incubated with a solution of AZT-TP. After 24 h of contact, the samples were centrifuged and the AZT-TP encapsulated was determined. It was shown that even after modification, the MIL-100 nanoparticles retained their capacity for encapsulating AZT-TP. The encapsulation yield was 99%, corresponding to a level of association with the nanoparticles of 7.8% (w/w). These results were similar to those obtained for the MIL-100s in the absence of any covering.

In addition, MIL-100 nanoparticles encapsulating AZT-TP were modified with chitosan (post-encapsulation modification). It was shown that the modification process only dislodged 4% of the encapsulated PA, by a dilution effect due to the covering process.

Figure 21:
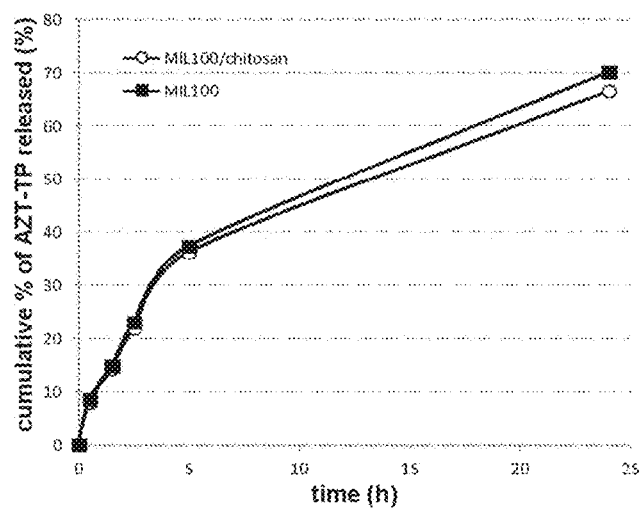
FIG. 21: Kinetics of release of AZT-TP from MIL-100 and chitosan-modified MIL-100 (post-encapsulation modification of AZT-TP).

The release of AZT-TP from post-encapsulation-modified MIL-100s was studied in PBS medium pH 7.4 at 37° C. and was compared to that from MIL-100s treated in the same conditions as the MIL-100/chitosan. The results obtained are presented in FIG. 21. They show that release of the active ingredient is not altered by the chitosan covering.

Figure 22:
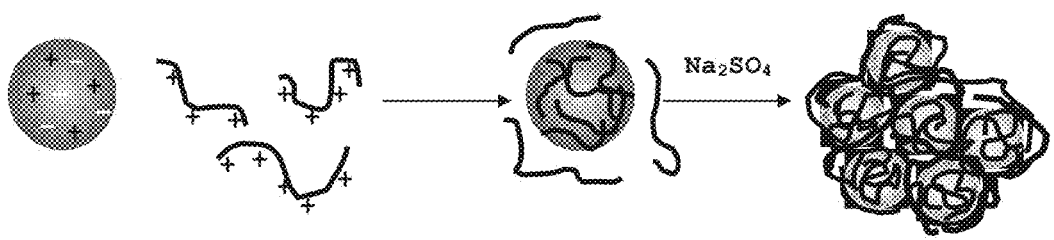
FIG. 22: Schematic representation of the association of chitosan with the MIL-100 nanoparticles by electrostatic interactions and addition of $Na_2SO_4$.

Increase of the Amount of Chitosan on the Surface of the MIL-100 Nanoparticles:

5 mg of MIL-100 was modified by incubation with 500 μL of an aqueous solution of chitosan at 2.5 mg/mL in 1% acetic acid (nanoparticles/chitosan weight ratio=4/1). After homogenization of the samples (vortex and ultrasound) allowing chitosan/MIL-100 interaction, a solution of $Na_2SO_4$ was added dropwise to the sample in an ultrasonic bath at room temperature. In this way, microparticles were obtained (FIG. 22). They were collected by gentle centrifugation (1380×g/1 min/25° C.). A uniform pellet was obtained. The microparticles were then purified by washing with deionized water and centrifugation (1380×g/1 min/25° C.). The operation was repeated 3 times.

In certain cases, other nanoparticles/chitosan weight ratios were tested.

Physicochemical Characterizations of the Microparticles

Figure 23:
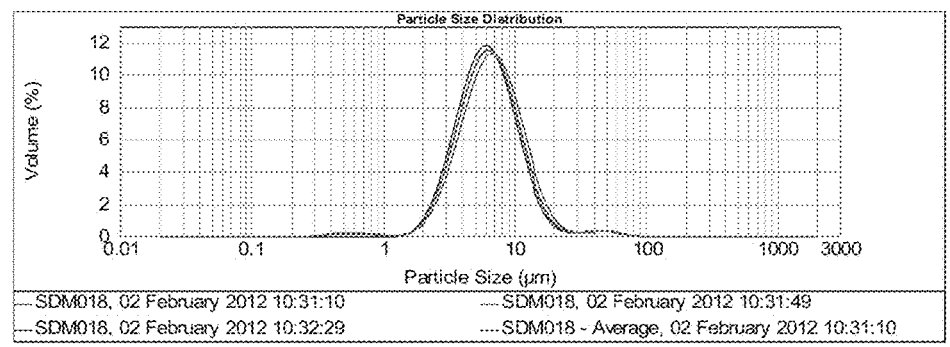
FIG. 23: Granulometric distribution of the MIL-100/chitosan microparticles. MIL-100/chitosan weight ratio: 20/1.

Particle Size and Morphology:

The size of the microparticles was measured by laser granulometry in a liquid medium (Mastersizer 2000, Malvern, France). They had an average diameter of 6.4 μm with a narrow distribution as indicated by the Span index equal to 1.5 (FIG. 23, Table 4). 10% of the particles have a diameter less than 3.3 μm and 90% of the particles have a diameter less than 12.6 μm.

TABLE 4

Granulometric parameters of a suspension of MIL-100/chitosan microparticles. MIL/chitosan weight ratio: 20/1.

| D(0.1) μm | D(0.5) μm | D(0.9) μm | Span |
|---|---|---|---|
| 3.3 | 6.4 | 12.6 | 1.5 |

Micro-Elemental Analysis:

Microparticles were prepared from 5 mg of MIL-100 and 0.25 mg of chitosan. After purification, the pellet of microparticles was dried at 100° C. for 18 h and then analyzed by micro-elemental analysis (Table 5). As the nitrogen atom was found specifically in the chitosan, it was possible to quantify its presence in the microparticles. The analysis showed that all the chitosan was associated with the MIL 100.

TABLE 5

Percentages of C, H and N determined by micro-elemental analysis in the samples of MIL-100, chitosan and MIL-100/chitosan microparticles.

|  | MIL-100 % measured | chitosan % measured | MIL-100/chitosan % measured |
|---|---|---|---|
| carbon | 36.5 | 45.5 | 31.7 |
| hydrogen | 2.7 | 6.7 | 2.1 |
| nitrogen | 0 | 8.5 | 0.4 |

Stability of the MIL-100/Chitosan Association:

Microparticles were prepared using chitosan labeled with rhodamine isothiocyanate (chitosan-RITC) with a MIL-100/chitosan weight ratio: 4/1; 8/1 and 20/1. After formation of the microparticles, the samples were centrifuged and washed with deionized water as described above. The supernatants from centrifugation of the samples and from the various washings were analyzed by spectrofluorimetry. It was shown that they did not contain chitosan, the latter being fully associated with the MIL-100 to form microparticles. This result confirms the results from micro-elemental analysis.

The microparticles labeled with rhodamine-ITC were resuspended in 1 mL of phosphate buffer pH 7.4. After 24 h of incubation at RT in this medium, the samples were centrifuged and the supernatants were analyzed by spectrofluorimetry. Chitosan-RITC was not detected in the supernatants, indicating that the MIL/chitosan association was stable in the phosphate buffer.

Figure 24:
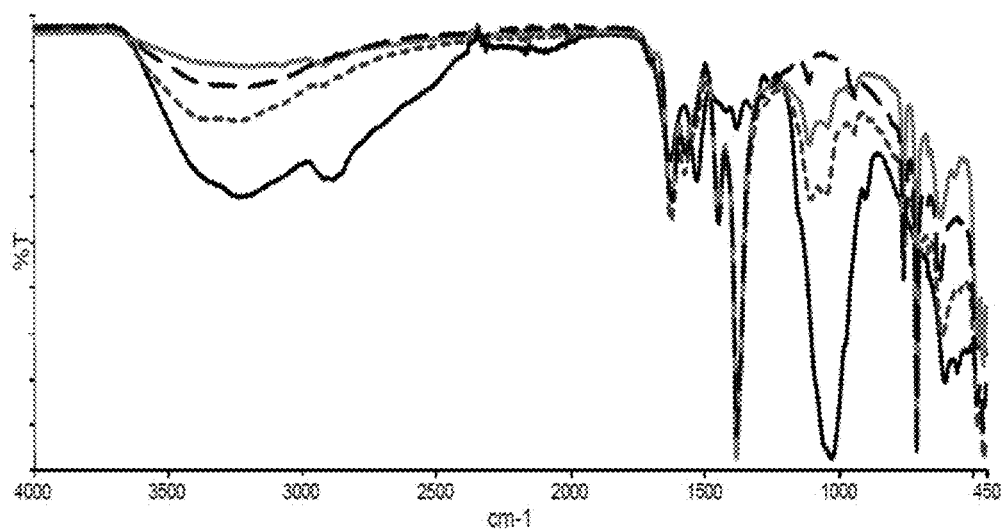
FIG. 24: IR spectra of chitosan (black solid line), MIL-100 nanoparticles (black dotted line) and MIL-100/chitosan microparticles weight ratio 10/1 (gray solid line) and 5/1 (gray dotted line).

Infrared Spectroscopy:

The microparticles were dried at 100° C. for 18 h and then analyzed by FT-IR. The spectra obtained clearly show the presence of an absorption band characteristic of chitosan at around 1030 $cm^{-1}$ (stretching band of the ether bond C—O—C) in the samples of microparticles. (FIG. 24)

XRD

Figure 25:
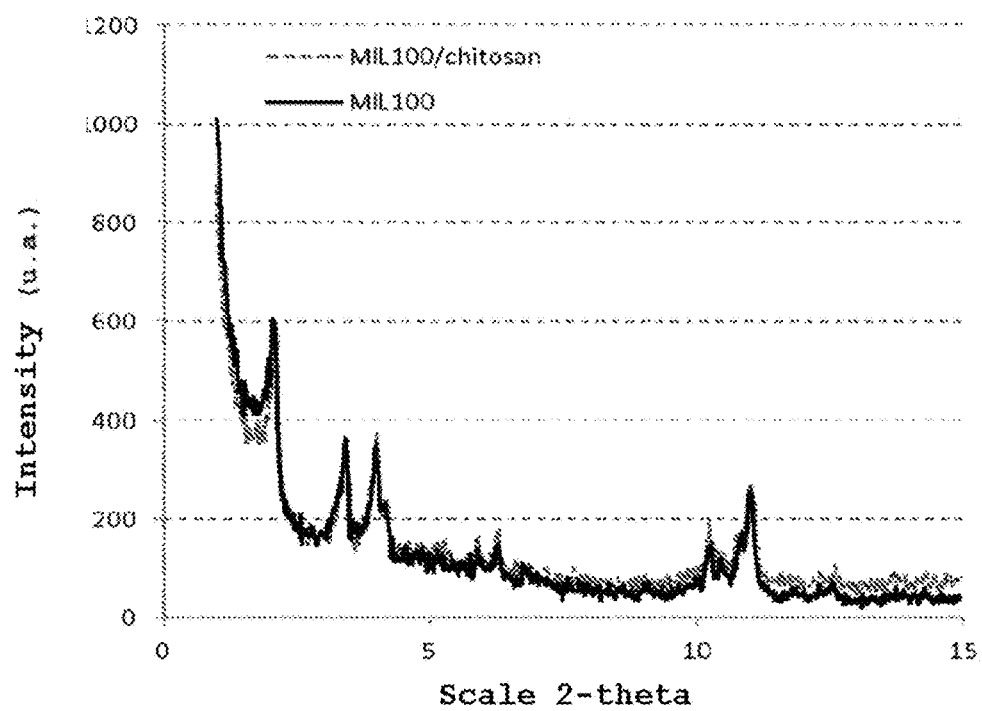
FIG. 25: X-ray diffraction patterns of MIL-100 and chitosan-modified MIL-100.

The materials MIL-100 and MIL-100/chitosan were dried for 18 h at 100° C. Their structure was analyzed by X-ray diffraction (Siemens D5000 X'Pert MDP high-resolution diffractometer (θ-2θ) (λCu, Kα1, Kα2). The results showed that the method of modification of the surface of the MIL-100s with chitosan does not alter the crystal structure of the MIL-100s (FIG. 25).

Encapsulation and Release of AZT-TP

Micrometric particles modified with chitosan were incubated with a solution of AZT-TP. After 24 h of contact, the samples were centrifuged and the AZT-TP encapsulated was determined. It was shown that even after modification, the particles of MIL-100 retained their capacity for encapsulating AZT-TP. The encapsulation yield was 99%, corresponding to a level of association of 7.8% (w/w). These results were similar to those obtained for the MIL-100s in the absence of any covering.

MIL-100/chitosan microparticles loaded with AZT-TP were also prepared from nanoparticles encapsulating AZT-TP (post-encapsulation modification). It was shown that the modification process (post-encapsulation of AZT-TP) only dislodged 0.8% of the encapsulated PA, by a dilution effect due to the covering process.

Figure 26:
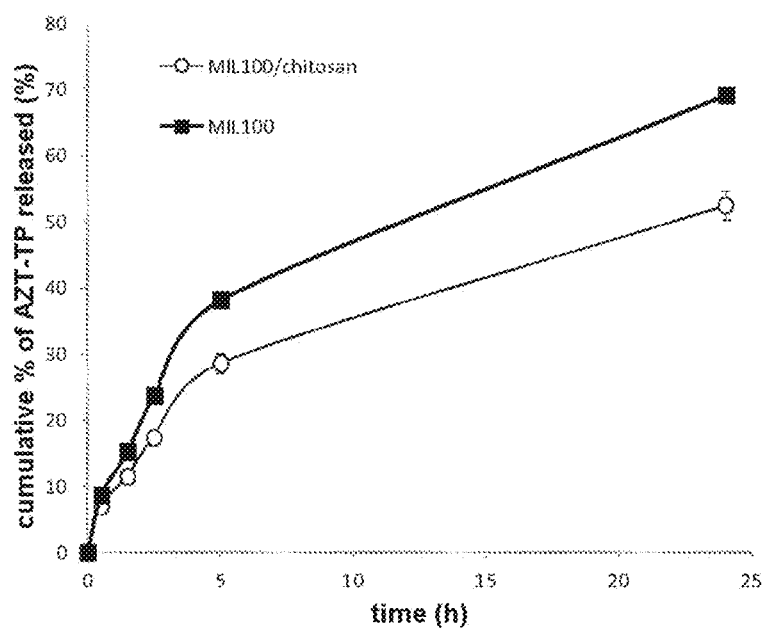
FIG. 26: Kinetics of release of AZT-TP from MIL-100 and MIL-100/chitosan microparticles (post-encapsulation modification).

Release of AZT-TP from MIL-100/chitosan microparticles (post-encapsulation modification) was studied at 37° C. in PBS medium pH 7.4. The results obtained are presented in FIG. 26. They show slower release of the active ingredient, due to the presence of chitosan.

Example 15

Figure 27:
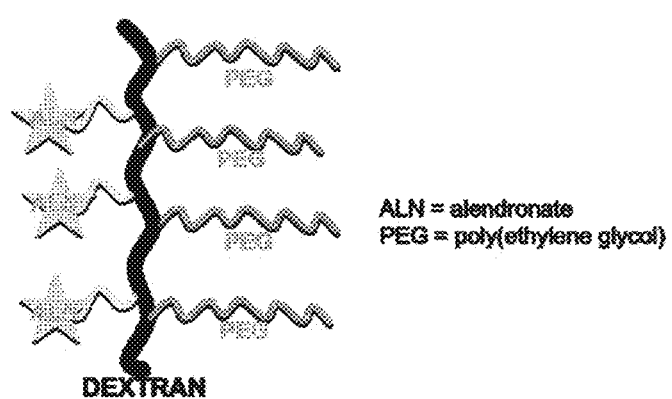
FIG. 27: PEG-alendronate-dextran bioconjugate.

Post-Synthesis Surface Modification of MIL-100 Nanoparticles with PEG-Alendronate-Dextran Bioconjugate Concept:

A PEG-alendronate-dextran bioconjugate was synthesized (FIG. 27) with a view to surface modification of the MOFs. This example relates to those based on iron trimesate (MIL-100). Dextran is a linear hydrophilic polysaccharide consisting of glucose units linked together by α-(1,6) bonds. This polymer offers the advantage that it is neutral, water-soluble, biocompatible and biodegradable. Moreover, it is used for biomedical applications and offers the possibility of grafting various ligands of interest for targeting.

The coupling of chains of polyethylene glycol (PEG) and alendronate molecules on the dextran skeleton is based on "click" reactions. Practically, we used the variety catalyzed by copper(I) of the Huisgen 1,3-dipolar cycloaddition of azides and of alkynes, for formation of 1,2,3-triazoles. So as to be able to use this "click" reaction, firstly we synthesized the azido-PEG, azido-alendronate and alkyne-dextran derivatives.

Alendronate is a molecule used for treating osteoporosis. The role of alendronate will be to ensure anchorage and stability of the dextran-PEG covering on the surface of the nanoMOF, by coordination with the iron.

Methods

Abbreviations

Ethyl acetate (EtOAc), dimethylformamide (DMF), dichloromethane (DCM), N-hydroxysuccinimide (NHS), 1-ethyl-3-(3'-dimethylaminopropyl)-N-(3-dimethylaminopropyl)-N'-ethylcarbodiimide hydrochloride (EDC), polyethylene glycol (PEG), 4-dimethylaminopyridine (DMAP), tetrahydrofuran (THF), 1,1-carbonyldiimidazole (DCI), molecular weight (MW), size exclusion chromatography (SEC).

Materials

All the reagents and solvents were obtained from the commercial sources given in parentheses and were used without any additional purifications otherwise stipulated. 6-Bromohexanoic acid (97%, Aldrich), $NaN_3$ (99%, Acros Organics), alendronate sodium (Molekula), NHS (purum, Fluka), EDC (Sigma-Aldrich), MePEG (Sigma-Aldrich), THF (Merck), Dextran T40 (average molecular weight MW 40000 dalton, Pharmacosmos, SEC MW (g/mol) 45360±8.0%), LiCl (99%, Acros), DCI (Aldrich), propargylamine (98%, Aldrich), 2-propanol (VWR), $CuSO_4$ ($5H_2O$) (Prolabo), sodium L-ascorbate (≥98%, Sigma-Aldrich), $Et_2O$ (Carlo Erba), EtOAc (Acros Organics), acetonitrile (Carlo Erba), DCM (Carlo Erba), EtOH (Carlo Erba), anhydrous DMF was distilled directly, Milli-Q deionized water was obtained from Millipore apparatus with a 0.22 μm filter, all the solvents were deuterated (Euriso-Top).

Synthesis of the Azido-Alendronate Fragment

Azido-alendronate was synthesized by a three-step synthesis procedure using 6-bromohexanoic acid as the starting product.

1. Synthesis of 6-azidohexanoic Acid

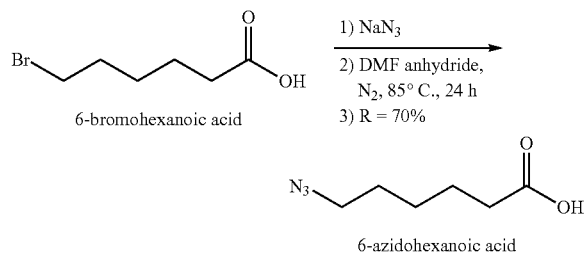

6-Azidohexanoic acid was synthesized on the basis of the methods already published, optimizing the procedures described.[1,2] Concretely, 6-bromohexanoic acid (MW 195.05 g/mol, 1.5 g, 7.7 mmol, 1 equiv.) was dissolved in DMF anhydride (10 mL). Next, $NaN_3$ (MW 65.01, 1 g, 15.4 mmol, 2 equiv.) was added. This mixture was heated at 85° C. with stirring and under $N_2$ for 24 h. At the end of reaction, the DMF was evaporated under vacuum. The resultant solid was dissolved in water (20 mL) and extracted with EtOAc (30 mL ×3). The organic phase was dried with $MgSO_4$, filtered and concentrated under vacuum to give 6-azidohexanoic acid in the form of a slightly yellow oil (0.872 g, 5.5 mmol, 70% yield). ESI-MS/MS (m/z) 156 (M-H)$^-$; $^1$H NMR (400 MHz, $^3J_{HH}$ (Hz), $CDCl_3$) δ: 11.04 (s, 1H, COOH), 3.24 (t, $^3J_{HH}$ 6.9, 2 H, $CH_2N_3$), 2.32 (t, $^3J_{HH}$ 7.3, 2H, $CH_2COOH$), 1.70-1.50 (m, 2H each, $CH_2CH_2COOH$, $CH_2CH_2N_3$), 1.40 (m, 2H, $CH_2CH_2CH_2N_3$); $^{13}$C NMR (100 MHz, $CDCl_3$) δ: 179.1 (COOH), 51.2 ($CH_2N_3$), 34.0 ($CH_2COOH$), 28.6 ($CH_2CH_2N_3$), 26.2 ($CH_2CH_2CH_2N_3$), 24.3 ($CH_2CH_2COOH$).

1] Aleman E A, Pedini H S, Rueda D, ChemBioChem, 2009, 10, 2862-2866

[2] Kuil J, Branderhorst H M, Pieters R J, de Mol N J, Liskamp R M, Org. Biomol. Chem., 2009, 7, 4088-94

2. Synthesis of 2,5-dioxopyrrolidin-1-yl-6-azidohexanoate

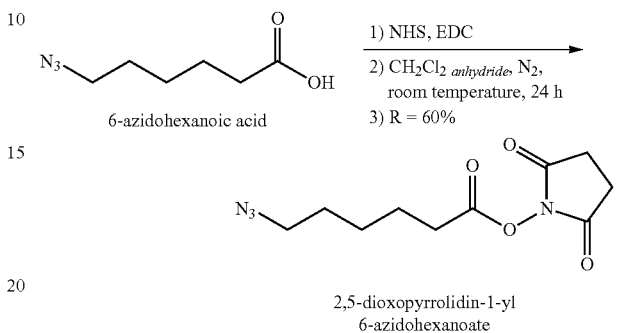

2,5-Dioxopyrrolidin-1-yl-6-azidohexanoate was synthesized on the basis of the methods already published, optimizing the procedure.[3,4] Concretely, 6-azidohexanoic acid (MW 157 g/mol, 0.6 g, 3.82 mmol, 1 equiv.) was dissolved in DCM anhydride (15 mL). Next, NHS (MW 115.05, 0.48 g, 4.2 mmol, 1.1 equiv.) was added under a nitrogen atmosphere and mixed by stirring for 5 min. Then EDC (MW 191.7, 0.8 g, 4.2 mmol, 1.1 equiv.) was added. This mixture was put under a nitrogen atmosphere and stirred at room temperature for 24 h. At the end of reaction, the crude reaction product was rinsed with an aqueous solution of 1N HCl (20 mL, ×2) and saturated $NaHCO_3$ solution (20 mL, ×2). Then the aqueous phases obtained were cleaned with DCM (20 mL, ×2). Then the organic phases were mixed, and the resultant organic phase was dried with $MgSO_4$, filtered and concentrated under vacuum to dryness. The product was purified by silica gel chromatography (pure DCM as mobile phase). The product was obtained in the form of a clear liquid (0.59 g, 2.32 mmol, 60% yield). $^1$H NMR (300 MHz, $^3J_{HH}$ (Hz), $CDCl_3$) δ: 3.23 (t, $^3J_{HH}$ 6.74, 2H, $CH_2N_3$), 2.75 (s, 4H, $COCH_2CH_2CO$), 2.56 (t, $^3J_{HH}$ 7.34, 2H, $CH_2COON$), 1.90-1.30 (m, 6H, $CH_2CH_2CH_2N_3$); $^{13}$C NMR (75 MHz, $CDCl_3$) δ: 169.1 ($NCOCH_2$), 168.4 ($CH_2COON$), 51.1 ($CH_2N_3$), 30.8 ($CH_2COON$), 28.4 ($CH_2$), 25.9 ($CH_2$), 25.6 ($2COCH_2CH_2CO$), 24.1 ($CH_2$).

[3] Liu X M, Lee H T, Reinhardt R A, Marky L E, Wang D., Journal of Controlled Release, 2007, 122, 54-62

[4] Grandjean C, Boutonnier A, Guerreiro, C, Fournier J-M, Mulard L-A, J. Org. Chem., 2005, 70, 7123-7132.

3. Synthesis of 4-(6-azidohexanamido)-1-hydroxy-1-phoshphonobutyl) sodium hydrogen phosphonate (azido-alendronate Compound)

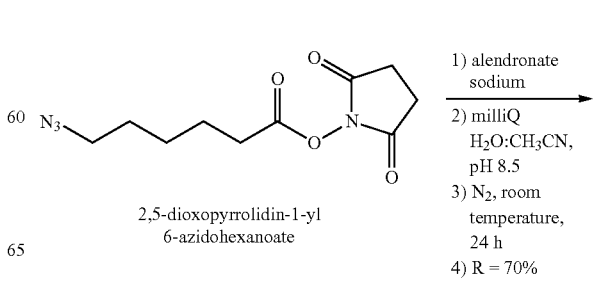

-continued

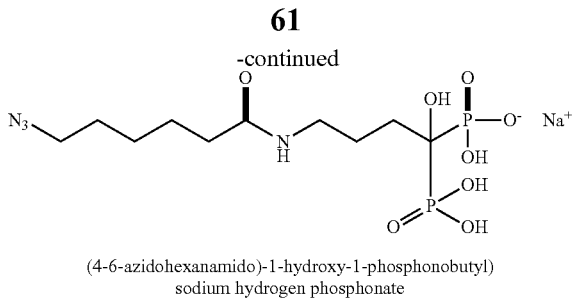

(4-6-azidohexanamido)-1-hydroxy-1-phosphonobutyl)
sodium hydrogen phosphonate

The azido-alendronate compound was synthesized on the basis of the methods already published, optimizing the procedure.[5,6] Concretely, alendronate sodium (MW 271.08, 0.445 g, 1.64 mmol, 1 equiv.) was dissolved in deionized water (10 mL). Then aqueous solution of NaOH (0.1 M, ~20 mL) was added dropwise to obtain pH of ~8.5. At that moment, 2,5-dioxopyrrolidin-1-yl-6-azidohexanoate (0.514 g, 2 mmol, 1.2 equiv.) was dissolved in acetonitrile (10 mL) and was added to the aqueous solution in 4 portions every 15 min. This mixture was stirred at room temperature. Before incorporating each portion, the pH was readjusted to between 8 and 8.5, obtaining a final volume of about 60 mL. After adding the last portion, the reaction mixture was stirred at room temperature for 24 h. At the end of the reaction, the solution was concentrated under vacuum to dryness. Next, the product was dissolved in water (3 mL) and precipitated with EtOH (30 mL). The solid product was recovered and dried, finally obtaining the appropriate product in the form of a white solid (0.47 g, 1.15 mmol, 70% yield). $^1$H NMR (400 MHz, $^3J_{HH}$ (Hz), D$_2$O) δ: 3.32 (t, $^3J_{HH}$ 6.8, 2H, CH$_2$N$_3$), 3.19 (t, $^3J_{HH}$ 7.0, 2H, CONHCH$_2$) 2.25 (t, $^3J_{HH}$ 7.4, 2H, CH$_2$CONH), 2.00-1.72 (m, 4H, CH$_2$CH$_2$C(PO$_3$H$_2$)$_2$(OH)), 1.67-1.54 (m, 2H each, CH$_2$CH$_2$CONH, CH$_2$CH$_2$N$_3$), 1.38 (m, 2H, CH$_2$CH$_2$CH$_2$N$_3$); $^{13}$C NMR (100 MHz, $^1J_{CP}$, $^3J_{CP}$ (Hz), D$_2$O) δ: 177.4 (CONH), 74.5 (t, $^1J_{CP}$ 129.0, C(PO$_3$H$_2$)$_2$(OH)), 51.6 (CH$_2$N$_3$), 40.8 (CONHCH$_2$), 36.3 (CH$_2$CONH) 32.1 (CH$_2$C(PO$_3$H$_2$)$_2$ (OH)),), 28.3 (CH$_2$CH$_2$N$_3$), 26.1 (CH$_2$CH$_2$CH$_2$N$_3$), 25.5 (CH$_2$CH$_2$CONH), 24.2 (t, $^3J_{CP}$ 6.5, CH$_2$CH$_2$C(PO$_3$H$_2$)$_2$(OH)); $^{31}$P (162 MHz, D$_2$O) δ: 19.25 (2P).

[5] Hein C D, Liu X-M, Chen F, Cullen D M, Wang D, Macromol. Biosci. 2010, 10, 1544-1556.

[6] Liu X-M, Lee H-T, Reinhardt R-A, Marky L E, Wang D, J. Control. Release 2007, 122, 54-62.

Synthesis of the Azido-PEG Compound

1. Synthesis of methoxy-poly(ethylene glycol) methanesulfonate (MePEG$_{43}$Ms)

A solution of MeOPEG$_{43}$OH (35 g, 17.5 mmol), DMAP (427 mg, 3.5 mmol) and distilled Et$_3$N (4.05 g, 40 mmol) in DCM (40 mL) was cooled to 0° C. Then MsCl (4.01 g, 35 mmol) was added dropwise with a syringe in the space of 15 min. The mixture was stirred at 0° C. for 30 min and then at room temperature overnight. At the end of the reaction the mixture was rinsed three times with an aqueous solution of HCl (0.5 M) and once with brine. Next, the organic phase was dried over MgSO$_4$, filtered and concentrated under vacuum, obtaining MePEG$_{43}$OMs in the form of white powder (28.36 g; (81% yield). IR (neat, cm$^{-1}$) ν=2890, 1467, 1340, 1279, 1240, 1175, 1147, 1105, 1059, 1017, 960; $^1$H NMR (300 MHz, CDCl$_3$) δ: 4.19 (m, 2 H, CH$_2$SO$_3$CH$_3$), 3.70-3.21 (m, 224 H, OCH$_2$CH$_2$O), 3.19 (s, 3 H, CH$_3$O-PEG), 2.91 (s, 3 H, CH$_2$SO$_3$CH$_3$); $^{13}$C NMR (75 MHz, CDCl$_3$) δ: 71.3 (CH$_2$, CH$_3$OCH$_2$), 69.9 (CH$_2$, OCH$_2$CH$_2$O), 68.8 (CH$_2$, CH$_2$CH$_2$OSO$_2$CH$_3$), 68.4 (CH$_2$, CH$_2$CH$_2$SO$_3$CH$_3$), 58.4 (CH$_3$, CH$_3$OCH$_2$), 37.1 (CH$_3$, CH$_2$OSO$_2$CH$_3$).

2. Synthesis of azidomethoxy poly(ethylene glycol) (MePEG$_{43}$N$_3$)

NaN$_3$ (1.755 g, 27 mmol) was incorporated in a solution of MePEG$_{43}$Ms (28 g, 14 mmol) in DMF (40 mL). The mixture was heated at 60° C. with stirring for 24 h. At the end of reaction, the DMF was evaporated under vacuum and a minimum amount of THF was added. The resultant solid was filtered and the THF was removed under vacuum. The solid obtained was dissolved in a minimum amount of DCM and was precipitated by the dropwise addition of a large volume of cold Et$_2$O. The product was then recovered by filtration. Finally, the solid was taken up in water and extracted with DCM (5×25 mL). The organic phase was dried over MgSO$_4$, filtered, concentrated and dried under vacuum, finally obtaining a slightly yellow powder (24.3 g, 87% yield). $^1$H NMR (400 MHz, D$_2$O) δ: 3.80-3.56 (m, OCH$_2$CH$_2$O), 3.51 (m, CH$_2$N$_3$), 3.38 (s, CH$_3$O); $^{13}$C NMR (100 MHz, D$_2$O) δ: 71.7 (CH$_3$OCH$_2$), 70.3 (OCH$_2$CH$_2$O), 70.2 (CH$_3$OCH$_2$CH$_2$O), 70.0 (OCH$_2$CH$_2$N$_3$), 58.8 (OCH$_3$), 50.9 (CH$_2$N$_3$).

Synthesis of the Alkyne-Dextran Compound

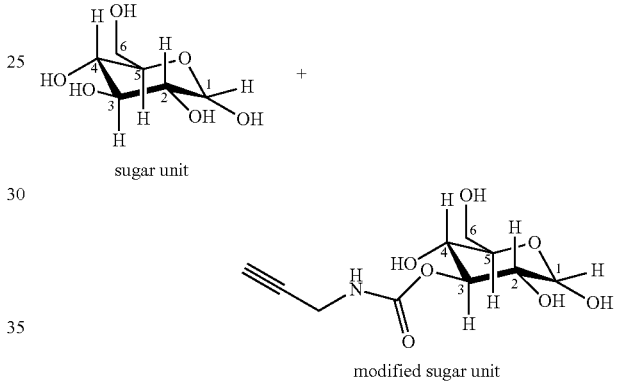

Dextran propargylcarbamate was synthesized on the basis of the methods already published, optimizing the procedure.[7,8] Practically, the protocol followed was:

Drying of the Reagents:

Dextran T40 (GPC MW (g/mol) 45360±8.0%, 0.5 g, 0.0110 mmol, 1 equiv.) and LiCl (MW 42.38, 0.125 g, 2.95 mmol, 268 equiv.) were dried individually under vacuum at 80° C. overnight. Then the two starting products were mixed and dried twice with anhydrous toluene and once with anhydrous DMF.

Dissolution of the Dextran:

A solution of the mixture containing the dry dextran T40 and LiCl in DMF (10 mL) was heated at 80° C. under a nitrogen atmosphere and with stirring until complete dissolution of the dextran T40.

Synthesis of Dextran Propargylcarbamate:

After dissolution of the dextran T40, the mixture was cooled to room temperature. Then DCI (MW 162, 0.099 g, 0.613 mmol, 49 equiv.) was added and the solution was stirred for 2 h at room temperature. Then propargylamine (MW 55.3, d 0.86, 0.4 mL, 6.125 mmol, 490 equiv.) was added and the solution was stirred for 24 h at room temperature. At the end of reaction, the product was recovered for precipitation by dropwise addition of a large volume of 2-propanol. The solid product was filtered and dissolved in milliQ deionized water (~5 mL). Then the aqueous solution was dialyzed for 48 h. Membranes with a cut-off of 12000-

14000 g/mol were used for dialysis. Then the dialyzed product was recovered and lyophilized, finally obtaining a white powder (SEC MW (g/mol): 45 450 (±2.1%), 0.40 g, 0.0088 mmol, 80% yield). EA (%) C, 40.7; H, 6.39; N, 0.79. $^1$H NMR (400 MHz, $^3J_{HaxHax}$ and $^3J_{HaxHeq}$ (Hz), D$_2$O) δ: 4.98 (d, $^3J_{HaxHeq}$ 3.3, CH(H$_1$)), 4.1-3.8 (m, CH$_2$(H$_6$), CH(H$_5$)), 3.8-3.65 (m, CH$_2$(H$_6$), CH(H$_5$)), 3.57 (dd, $^3J_{HaxHax}$ 9.6, $^3J_{HaxHeq}$ 3.3, CH(H$_2$)), 3.52 (t, $^3J_{HaxHax}$ 9.6, CH(H$_4$)); $^{13}$C NMR (100 MHz, D$_2$O) δ: 98.4 (CH(C$_1$)), 74.0 (CH(C$_3$)), 72.1 (CH(C$_2$)), 70.9 (CH(C$_5$)), 70.2 (CH(C$_4$)), 66.2 (CH$_2$(C$_6$)).

The following signals were assigned based on the HSQC spectrum: $^1$H NMR (400 MHz, $^3J_{HaxHax}$ and $^3J_{HaxHeq}$ (Hz), D$_2$O) δ: 3.9 (CH$_2$NHCOO); $^{13}$C NMR (100 MHz, D$_2$O) δ: 30.9 (CH$_2$NHCOO).

[7] Mohamad Othman Ph.D thesis, Châtenay Malabry, 2010.

[8] Lukyanov A N et al., J Biomater Sci Polym Ed. 2004, 15(5), 621-30

Synthesis of PEG-Alendronate-Dextran Bioconjugate Based on "Click" Reactions

A "click" reaction was used as the method of synthesis. Concretely, the reaction of cycloaddition of azides and of alkynes catalyzed by copper(I) was employed. [5, 9, 10]

1. Synthesis of the PEG-Dextran Bioconjugate

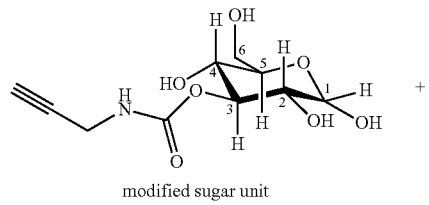

modified sugar unit

+

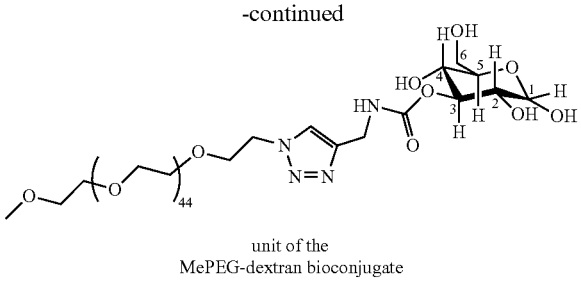

unit of the
MePEG-dextran bioconjugate

Dextran propargylcarbamate (SEC MW (g/mol): 45 450 (±2.1%), 0.3 g, 0.0068 mmol, 1 equiv.) and methoxy-poly (ethylene glycol)azide (MeOPEG$_{43}$N$_3$, theoretical monoisotopic mass 2054.2 m/z, 0.14 g, 0.068 mmol, 10 equiv.) were mixed under a nitrogen atmosphere. Then an aqueous solution (5 mL) containing CuSO$_4$(5H$_2$O) (MW 249.69, 0.017 g, 0.067 mmol, 10 equiv.) purged beforehand with nitrogen was added. The resultant solution was held at room temperature with stirring and N$_2$ for 5 min. Then an aqueous solution of sodium ascorbate (MW 198.1, 0.016 g, 0.08 mmol, 12 equiv.) (5 mL) was added. Then the mixture was stirred under nitrogen at room temperature for 24 h. At the end of the reaction the solution was dialyzed for 48 h (membranes with a cut-off of 12000-14000 g/mol). Then the dialyzed product was recovered and lyophilized, finally obtaining a slightly greenish white powder. (SEC MW (g/mol): 62 120 (±2.3%), 0.33 g, 0.0053 mmol, 78% yield). $^1$H NMR (400 MHz, T 320K (47° C.), $^3J_{HaxHax}$ and $^3J_{HaxHeq}$ (Hz), D$_2$O) δ: 7.98 (s, CH-triazole), 4.98 (d, $^3J_{HaxHeq}$ 3.1, CH(H$_1$)), 4.08-3.84 (m, CH$_2$(H$_6$), CH(H$_5$)), 3.8-3.42 (m), 3.38 (s, OCH$_3$); $^{13}$C NMR (100 MHz, T 320K (47° C.), D$_2$O) δ: 98.5 (CH(C$_1$)), 74.2 (CH(C$_3$)), 72.2 (CH(C$_2$)), 71.0 (CH(C$_5$)), 70.4 (CH(C$_4$)), 70.3 (OCH$_2$CH$_2$O), 66.5 (CH$_2$ (C$_6$)), 50.8 (CH$_2$N-triazole).

[7] Lewis W G, Magallon F G, Fokin V V, Finn M G, J. Am. Chem. Soc., 2004, 126, 9152-9153

[8] Phaimanolis N, Vesterinen A-H, Rich J, Seppala J, Carbohydrate Polymers, 2010, 82, 78-82

2. Synthesis of the PEG-Alendronate-Dextran Bioconjugate

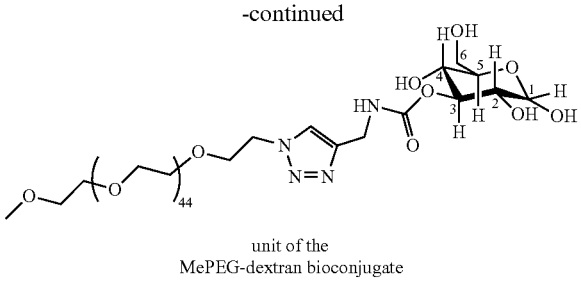

unit of
MePEG-dextran bioconjugate

+

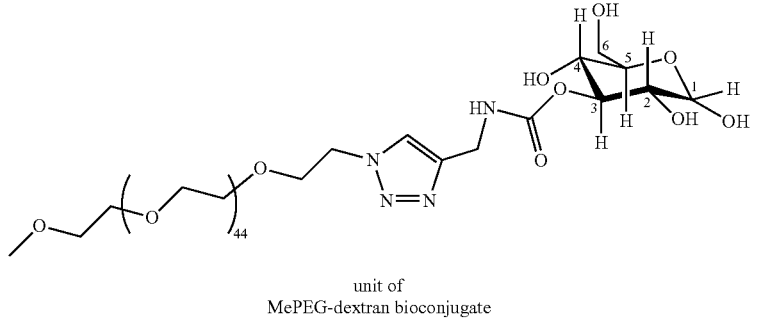

unit of
MePEG-dextran-alendronate bioconjugate

The PEG-dextran bioconjugate (SEC MW (g/mol): 62 120 (±2.3%)) and azido-alendronate were mixed under a nitrogen atmosphere. Then an aqueous solution (5 mL) containing $CuSO_4(5H_2O)$ (MW 249.69, 0.017 g, 0.067 mmol, 10 equiv.) purged beforehand with nitrogen was added. The resultant solution was held at room temperature with stirring and $N_2$ for 5 min. Then an aqueous solution of sodium ascorbate (MW 198.1, 0.016 g, 0.08 mmol, 12 equiv.) (5 mL) was added. Then the mixture was stirred under nitrogen at room temperature for 24 h. At the end of the reaction the solution was dialyzed for 48 h (membranes with a cut-off of 12000-14000 g/mol). Then the dialyzed product was recovered and lyophilized.

Example 16

Figure 28:
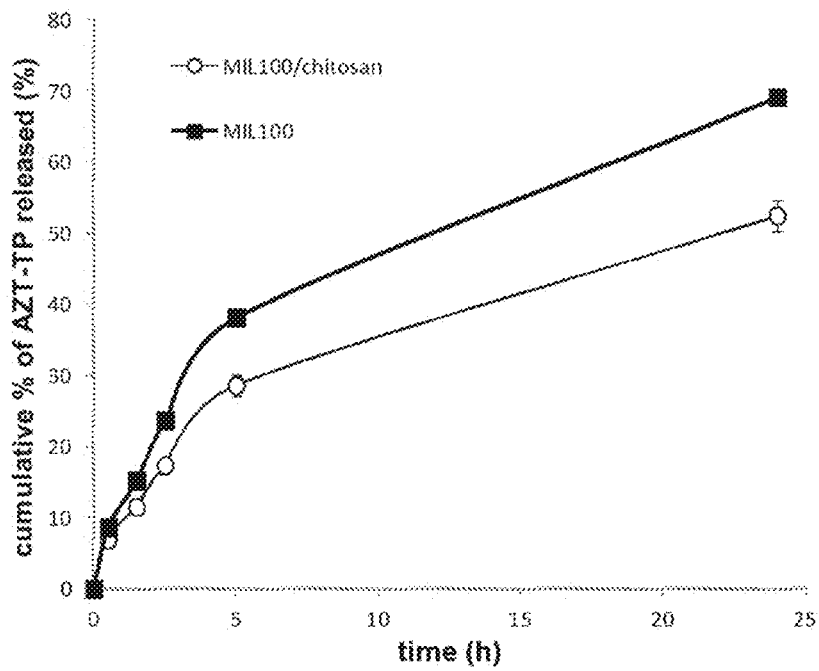
FIG. 28: Detachment of βCDP-rhodamine from MIL-100 (Fe) nanoparticles in PBS at 37° C.

Surface Modification of MIL-100 Nanoparticles with Poly-βCDP 2 mg of MIL-100 nanoparticles were modified by incubation with 500 µl of an aqueous solution of poly-βCDP-rhodamine (1:10, 1 phosphate/10 cyclodextrins) 2 mg/ml (weight ratio nanoparticles:βCDP=1:0.5), for 24 h with stirring at room temperature. After incubation, the modified nanoparticles were recovered by centrifugation at 9500 g, 10 min and the supernatant was analyzed by spectrofluorimetry in order to define the amount of poly-βCDP-rhodamine bound to the nanoparticles. The results obtained indicate that the amount of βCDP-rhodamine associated with the MIL-100s represents 34(±0.5) % w/w. The modified nanoparticles were washed with 1 ml of water, to remove the excess poly-βCDP-rhodamine, and finally were incubated in 1 ml of PBS (Phosphate Buffered Saline, Lonza) at 37° C., with stirring at a concentration of 2 mg/ml. After various incubation times (0.3-6-24 h) the suspension was centrifuged for 10 min at 9500 g, 500 µL of supernatant was taken and was replaced with the same amount of fresh medium. The supernatants were analyzed by spectrofluorimetry, in order to quantify the release of poly-βCDP-rhodamine in the medium. The results showed that only 27.24% of βCDP-rhodamine bound to the nanoparticles is released after 6 h of incubation in PBS (FIG. 28). It may be concluded that the outer corona of poly-βCDP-rhodamine is stable in physiological conditions, probably owing to the cooperative effect of several phosphate groups in the polyCD.

Example 17

Figure 29:
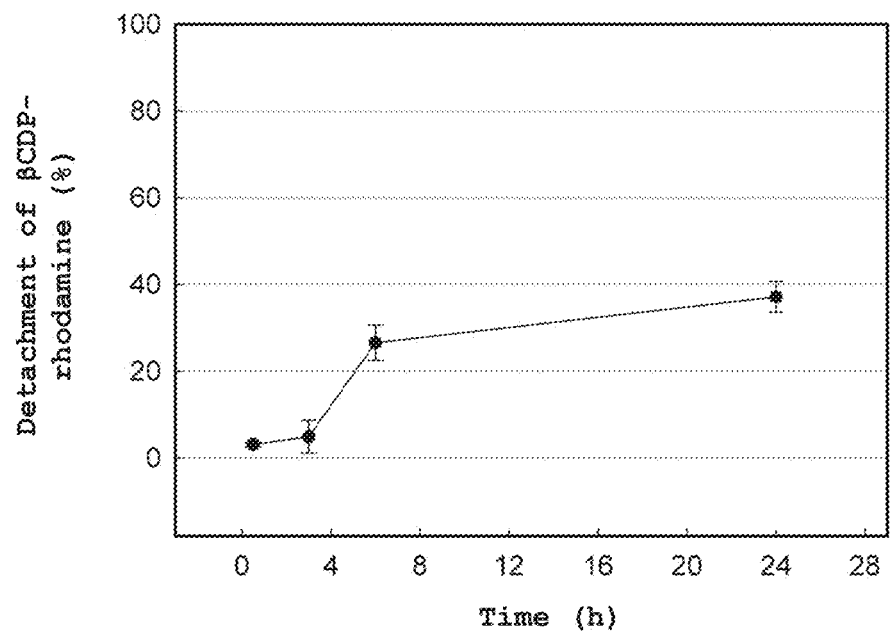
FIG. 29: Detachment of βCDP-rhodamine from MIL-100 (Al) nanoparticles in PBS at 37° C.

Surface Modification of the Nanoparticles of MIL-100(Al) Based on βCDP 2 mg of nanoMOF of MIL-100(Al) was incubated with 500 µl of an aqueous solution of βCDP-rhodamine, for 24 h with stirring, at room temperature. At the end of incubation, the nanoparticles were recovered by centrifugation at 9491×g for 10 min, and the supernatant was analyzed by spectrofluorimetry in order to define the amount of βCDP-rhodamine bound to the nanoparticles. The results obtained indicate that the amount of βCDP-rhodamine associated with the MIL-100(Al) represents 29.6(±0.6) % w/w. The modified nanoparticles were washed with 1 ml of water to remove the excess βCDP-rhodamine and finally were incubated in 1 ml of PBS (Phosphate Buffered Saline, Lonza) at 37° C., with stirring. After various incubation times (0.3, 6.24 h) the suspension was centrifuged for 10 min at 9491×g, 500 µL of supernatant was taken and was replaced with the same amount of fresh medium. The supernatants were analyzed by spectrofluorimetry, in order to quantify the release of βCDP-rhodamine in the medium. The results showed that only 26.5(±4) % of βCDP-rhodamine bound to the nanoparticles is released after 6 h of incubation and this percentage does not exceed 37.1(3.5) % after 24 h (FIG. 29). It may be concluded that the outer corona of βCDP is stable in physiological conditions, and that this method of surface modification is also valid for nanoMOFs based on metals other than iron, such as MIL-100(Al).

LIST OF REFERENCES

[1] WO 2009/077670
[2] WO 2009/077671
[3] Bone Marrow Transplant. 2002.30 (12), 833-841
[4] U.S. Pat. No. 4,329,332
[5] J. Bouligand, et al., *Int. J. Pharm.*, 2004
[6] E. Renard et al., European Polymer Journal, vol. 33, No 1, pp 49-57 (1997)
[7] Gref et al., International Journal of Pharmaceutics, Vol. 332, Issues 1-2, Pages 185-191 (2007)
[8] Gref et al., J. Control Release, 111(3):316-24 (2006)
[9] Gref et al., Journal of colloid and interface science, 307(1):83-93 (2007)
[10] Blanchemain et al., Acta Biomaterialia, Volume 4, Issue 6, November 2008, Pages 1725-1733
[11] Elif Yilmaz Ozmen et al. *Bioresource Technology*, Volume 99, Issue 3, Pages 526-531 (2008)
[12] Cesteros et al., European Polymer Journal, Volume 45, Issue 3, Pages 674-679 (2009) (acylated PEG)
[13] Salmaso et al., *International Journal of Pharmaceutics*, Volume 345, Issues 1-2, Pages 42-50 (2007) (diaminated PEG)
[14] Yang et al., *Biomaterials*, Volume 28, Issue 21, Pages 3245-3254 (2007)
[15] G. Oros, T. Cserhati, E. Forgacs, *Chemosphere* 52, 2003, 185
[16] A. M. Badawi, E. M. S. Azzam, S. M. I. Morsy, *Bioorg. Med. Chem.*, 14, 2006, 8661
[17] W.-J. Tsai, Y-J Shiao, S-J Lin, W-F Chiou, L-C Lin, T-H Yang, C-M TENG, T-S Wu, L-M Yang, *Bioorg. Med. Chem. Letters* 16, 2006, 4440
[18] Whitfield, T. R.; Wang, X.; Liu, L.; Jacobson, A. J. *Solid State Sci.* 2005, 7, 1096
[19] T. Loiseau et al, C. R. *Chimie*, 8 765 (2005).
[20] Serre et al., "Role of solvent-host interactions that lead to very large swelling of hybrid frameworks", Science, 2007, Vol. 315, 1828-1831
[21] Surblé et al., "A new isoreticular class of metal-organic frameworks with the MIL-88 topology", Chem. Comm., 2006, 284-286
[22] Mellot-Draznieks et al., "Very large swelling in hybrid frameworks: a combined computational and powder diffraction study", J. Am. Chem. Soc., 2005, Vol. 127, 16273-16278
[23] C. Serre, F. Millange, S. Surblé, G. Férey *Angew. Chem. Int. Ed.* 2004, 43, 6286: A new route to the synthesis of trivalent transition metals porous carboxylates with trimeric SBU
[24] Horcajada et al., "Synthesis and catalytic properties of MIL-100(Fe), an iron(III) carboxylate with large pores", Chem. Comm., 2007, 2820-2822
[25] Férey et al., "A chromium terephthalate-based solid with unusually large pore volumes and surface area", Science, 2005, Vol. 309, 2040-2042
[26] S. Surblé, F. Millange, C. Serre, T. Düren, M. Latroche, S. Bourrelly, P. L. Llewellyn and G. Férey "MIL-102: A Chromium Carboxylate Metal Organic Framework with Gas Sorption Analysis" *J. Am. Chem. Soc.* 128 (2006), 46, 14890

[27] Mulder W J, et al. *Nanomed.* 2007 June, 2(3), 307-324

[28] A. K. Gupta, et al., *Nanomed.* 2007 2(1), 23-39

[29] P Caravan, *Chem. Soc. Rev.*, 2006, 35, 512-523

[30] Yan-Ping Ren, et al., *Angew. Chem. Int. Ed.* 2003, 42, No. 5, 532

[31] J. Mater. Chem., 2010, 20, 7676-7681; A. Demessence, et al, J. Mater. Chem., 2010, 20, 7676-7681

[32] J. H. Cavka et al., JACS, 2009, 130, 13850-13851

[33] Baleaux B. et al., "Chimie analytique-dosage colorimétrique d'agents de surface non ioniques polyoxyéthylènes à l'aide d'une solution iode-iodurée", C. R. Acad. Sciences Paris, 1972, série C, 274, 1617-1620.

[34] Navath R S, Menjoge A R, Dai H, Romero R, Kannan S, Kannan R M., Injectable PAMAM dendrimer-PEG hydrogels for the treatment of genital infections: formulation and in vitro and in vivo evaluation, Mol Pharm. 2011 Aug. 1; 8(4):1209-23

[35] R C. Hedden et B. J. Bauer, Structure and Dimensions of PAMAM/PEG Dendrimer_Star Polymers, Macromolecules, 2003, 36 (6), pp 1829_1835

[36] N Bhattarai, H R. Ramay, J Gunn, F A. Matsen, M Zhan, PEG-grafted chitosan as an injectable thermosensitive hydrogel for sustained protein release, J Controlled Release, 103 (3), 609-624, 2005

[37] J. A Wieland, T. L. Houchin-Ray, L. D. Shea, Non-viral vector delivery from PEG-hyaluronic acid hydrogels, J. Controlled Release, 120 (3), 233-241, 2007

[38] X. M. Liu, H. Lee, R. Reinhardt, L. Marky, W Dong, J. Controlled Release vol 122, 2007, 54-62, Novel biomineral-binding cyclodextrins for controlled drug delivery in the oral cavity

[39] Chalati et al., "Optimisation of the synthesis of MOF nanoparticles made of flexible porous iron fumarate MIL-88A", J. Mater. Chem., 2011, 21, 2220

[40] Cavka, J.; Jakobsen, S.; Olsbye, U.; Guillou, N.; Lamberti, C.; Bordiga, S.; Lillerud, K., *J. Am. Chem. Soc.* 2008, 130, 13850

[41] Kandiah, M.; Nilsen, M. H.; Usseglio, S.; Jakobsen, S.; Olsbye, U.; Tilset, M.; Larabi, C.; Quadreli, E. A.; Bonino, F.; Lillerud K. P., *Chem. Mater.*, 2010, 22(24), 6632

[42] Garibay S. J.; Cohen S. M., *Chem. Commun.*, 2010, 46, 7700

[43] Park et al., "Exceptional chemical and thermal stability of zeolitic imidazolate frameworks

[44] M. Dan-Hardi, C. Serre, T. Frot, L. Rozes, G. Maurin, C. Sanchez and G. Férey: *J. Am. Chem. Soc. Comm.*, 131, 2009, 10857-10859 A New Photoactive Crystalline Highly Porous Titanium (IV) Dicarboxylate", Proc. Natl. Acad. Sci. U.S.A., 2006, 103, 10186

[45] C. Zlotea, D. Phanon, M. Mazaj, D. Heurtaux, V. Guillerm, C. Serre, P. Horcajada, T. Devic, E. Magnier, F. Cuevas, G. Férey, P. L. Llewellyn and M. Latroche: "Effect of NH$_2$ and CF$_3$ functionalization on the hydrogen sorption properties of MOFs" *Dalton Trans.*, 2011, 40, 4879-4881

[46] A. E. Platero-Prats, V. A. de la Pena-O'Shea, N. Snejko, A. Monge, E. Gutierrez-Puebla, "Dynamic calcium metal-organic framework acts as a selective organic solvent sponge", Chemistry, 16(38), 11632

[47] C. Volkringer, J. Marrot, G. Ferey, T. Loiseau, "Hydrothermal crystallization of three calcium-based hybrid solids with 2,6-naphthalene or 4,4'-biphenyl-dicarboxylates" Crystal Growth Design, 2008, 8, 685

[48] Horcajada et al., "How linker's modification controls swelling properties of highly flexible iron(III) dicarboxylates MIL-88", J. Am. Chem. Soc., 2011, 133, 17839

[49] Devic et al., "Functionalization in flexible porous solids: effects on the pore opening and the host-guest interactions", J. Am. Chem. Soc., 2010, 132, 1127

[50] C. Serre, S. Surblé, C. Mellot-Draznieks, Y. Filinchuk, G. Férey *Dalton Trans.*, 2008, 5462-5464: Evidence of flexibility in the nanoporous iron(III) carboxylate MIL-89

[51] C. T. Dziobkowski, T. J. Wrobleski, D. B. Brown, Inorg. Chem. 1982, 21, 671

The invention claimed is:

1. A porous crystalline MOF solid comprising a three-dimensional succession of units having the following formula (I):

$$M_mO_kX_lL_p \qquad \text{Formula (I)}$$

wherein:

each occurrence of M independently represents a metal ion selected from the group comprising $Fe^{2+}$, $Fe^{3+}$, $Zn^{2+}$, $Zr^{4+}$, $Ti^{4+}$, $Ca^{2+}$, $Mg^{2+}$ and $Al^{3+}$;

m, k, l and p numbers ≥0 selected so as to respect charge neutrality of the unit;

X is a ligand selected from the group comprising $OH^-$, $Cl^-$, $F^{31}$, $I^-$, $Br^-$, $SO_4^{2-}$, $NO_3^-$, $ClO_4^-$, $R^1$—$(COO)_n^-$, $R^1$—$(SO_3)n^-$, $R^1$—$(PO_3)n^-$, wherein $R^1$ is a hydrogen atom, a linear or branched $C_1$ to $C_8$ alkyl, n =1 to 6; and L is a polyfunctionalized spacer ligand comprising a radical $R^0$ and q occurrences of a complexing group A, where q is an integer between 2 and 6;

each occurrence of A is independently:

(i) a carboxylate

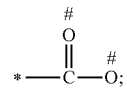

(ii) a phosphonate

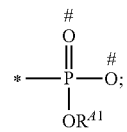

or (iii) an imidazolate group

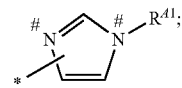

wherein $R^{41}$ represents a hydrogen atom or a $C_{1-6}$alkyl radical;

wherein * denotes the point of attachment of group A to the radical $R^0$;

# denotes the possible points of attachment of group A to the metal ion M;

$R^0$ represents a $C_{1-12}$alkylene, $C_{2-12}$alkenylene or $C_{2-12}$alkynylene radical;

a mono- or polycyclic aryl radical, fused or not, comprising from 6 to 50 carbon atoms, a mono- or polycyclic heteroaryl radical, fused or not, comprising from 4 to 50 carbon atoms, the radical $R^O$ optionally being substituted with one or more groups independently selected from the group halogen atom, OH, $NH_2$, $NO_2$ or a $C_1$ to $C_6$ alkyl;

wherein the outer surface of the MOF is modified in that it comprises at least one organic surface agent complexed with a metal center M or with a ligand L located on the outer surface of the crystalline MOF solid, the organic surface agent comprising: i) at least one phosphate, phosphonate, bisphosphonate, sulfate, carboxylate, hydroxy, cathecolate, thiolate (—SR or —S⁻), N-containing heterocyclic, amido (—C(=O)N(R)$_2$), amino (—N(R)$_2$) group, or a combination of these groups, wherein each occurrence of R represents independently H, $C_{1-6}$alkyl or phenyl);

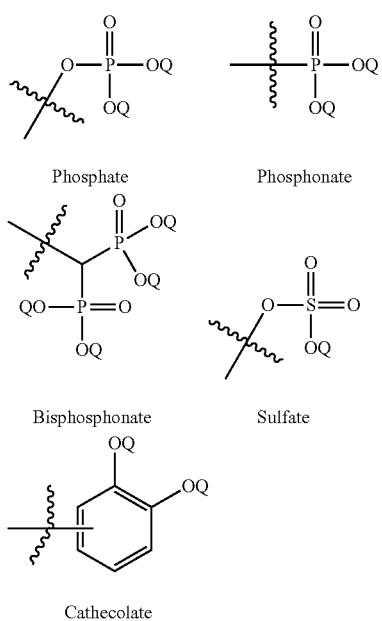

wherein each occurrence of Q represents independently H or an alkali metal cation;

and/or ii) a rigid section larger than the largest sized pore access windows of the MOF material;

the organic surface agent being selected from
α-, β- or γ-cyclodextrins;
oligomers of α-, β- or γ-cyclodextrins;
poly-α, poly-β or poly-γ-cyclodextrins,
copolymers of α, β and or γ-cyclodextrins,
PEG dendrimers,
chitosan bearing a plurality of PEG side chains,
albumin,
immunoglobulins, or
dextran grafted both with PEG chains and alendronate bisphosphonate groups;
said organic surface agent interacting with a metal center M or with a ligand L located on the outer surface of the crystalline MOF solid via said one or more phosphate, phosphonate, bisphosphonate, sulfate, carboxylate, hydroxy, cathecolate, thiolate, N-containing heterocyclic, amido, amino group(s), or a combination of these groups.

2. A solid according to claim 1, wherein the ligand L is a spacer bearing several complexing groups selected from carboxylate, phosphonate, imidazolates group, wherein the carboxylate group is a di-, tri-, tetra- or hexa-carboxylate selected from the group comprising:

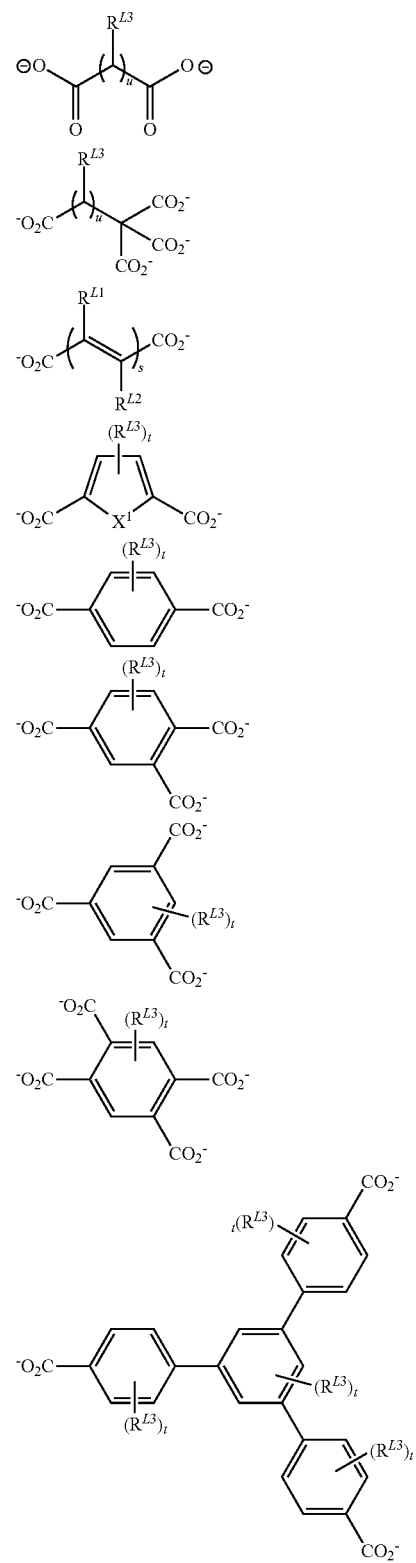

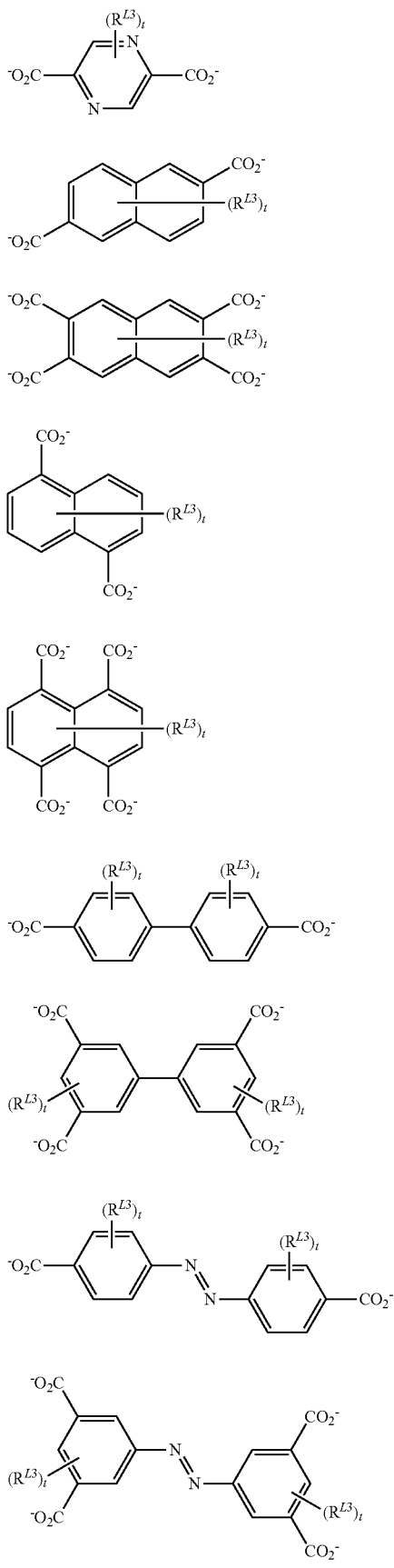

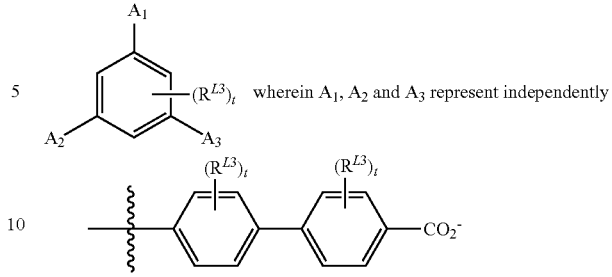

wherein:

$X_1$ represents O or S, s represents an integer from 1 to 4, each occurrence of t represents independently an integer from 1 to 4, u represents an integer from 1 to 7, $R^{L1}$ and $R^{L2}$ represent independently H, a halogen atom or a $C_1$ to $C_6$ alkyl, and each occurrence of $R^{L3}$ represents independently H, a halogen atom, OH, $NH_2$, $NO_2$ or a $C_1$ to $C_6$ alkyl.

3. A solid according to claim 1, wherein the ligand L is a di-, tri- or tetracarboxylate ligand selected from the group comprising: $C_2H_2(CO_2^-)_2$(fumarate), $C_2H_4(CO_2^-)_2$ (succinate), $C_3H_6(CO_2^-)_2$(glutarate), $C_4H_4(CO_2^-)_2$(muconate), $C_4H_8(CO_2^-)_2$ (adipate), $C_7H_{14}(CO_2^-)_2$ (azelate), $C_5H_3S(CO_2^-)_2$ (2,5-thiophenedicarboxylate), $C_6H_4(CO_2^-)_2$ (terephthalate), $C_6H_2N_2(CO_2^-)_2$(2,5-pyrazine dicarboxylate), $C_{10}H_6(CO_2^-)_2$ (naphthalene-2,6-dicarboxylate), $C_{12}H_8(CO_2^-)_2$ (biphenyl-4,4'-dicarboxylate),$C_{12}H_8N_2(CO_2^-)_2$ (azobenzenedicarboxylate), $C_6H_3(CO_2^-)_3$ (benzene-1,2,4-tricarboxylate), $C_6H_3(CO_2^-)_3$ (benzene-1,3,5-tricarboxylate), $C_{24}H_{15}(CO_2^-)_3$(benzene-1,3,5-tribenzoate), $C_6H_2(CO_2^-)_4$ (benzene-1,2,4,5-tetracarboxylate, $C_{10}H_4(CO_2^-)_4$ (naphthalene-2,3,6,7-tetracarboxylate), $C_{10}H_4(CO_2^-)_4$ (naphthalene-1,4,5,8-tetracarboxylate), $C_{12}H_6(CO_2^-)_4$ (biphenyl-3,5,3',5'-tetracarboxylate), and the modified analogs selected from the group comprising 2-aminoterephthalate, 2-nitroterephthalate, 2-methylterephthalate, 2-chloroterephthalate, 2-bromoterephthalate, 2,5-dihydroxoterephthalate, tetrafluoroterephthalate, tetramethylterephthalate, dimethyl-4,4'-biphenyldicarboxylate, tetramethyl-4,4'-biphenyldicarboxylate, dicarboxy-4,4'-biphenyldicarboxylate, 2,5-pyrazyne dicarboxylate, 2,5-diperfluoroterephthalate, azobenzene-4,4'-dicarboxylate, 3,3'-dichloro azobenzene-4,4'-dicarboxylate, 3,3'-dihydroxo azobenzene-4,4'-dicarboxylate, 3,3'-diperfluoro-azobenzene-4,4'-dicarboxylate, 3,5,3',5'-azobenzene tetracarboxylate, 2,5-dimethylterephthalate, perfluorosuccinate, perfluoromuconate, perfluoroglutarate, 3,5,3',5' perfluoro-4,4'-azobenzene dicarboxylate, 3,3'-diperfluoro-azobenzene-4, 4'-dicarboxylate.

4. A solid according to claim 1, wherein the ligand L is a fluorinated ligand selected from the group comprising tetrafluoroterephthalate, perfluorosuccinate, perfluoromuconate, perfluoroglutarate, 2,5-diperfluoroterephthalate, 3,6-perfluoro-1,2,4,5-benzenetetracarboxylate, 3,5,3',5'-perfluoro-4,4'-azobenzene dicarboxylate, 3,3'-diperfluoro-azobenzene-4,4'-dicarboxylate.

5. A solid according to claim 1, wherein the ligand L is a biologically active ligand selected from the group comprising $C_7H_{14}(CO_2^-)_2$; aminosalicylate; clodronate, pamidrontate, alendronate, etidronate; meprobamate; porphyrins comprising carboxylate, phosphonate and/or amino groups; amino acids; azobenzenes comprising carboxylate, phosphonate, and/or amino groups; dibenzofuran-4,6-dicarboxylate, dipicolinate; glutamate, fumarate, succinate, suberate, adipate, nicotinate, nicotinamide, purines, pyrimidines.

6. The solid as claimed in claim 1, wherein the cyclodextrin units of the poly-α, poly-β or poly-γ-cyclodextrin or the copolymer of α, β and/or γ-cyclodextrin are linked together by hydrocarbon chains of formula —O—(CH$_2$—CHOR$^1$—CH$_2$)$_n$—O—wherein n is an integer between 1 and 50 and, in each of the units (CH$_2$—CHOR$^1$—CH$_2$), R$^1$ denotes either a hydrogen atom, or a —CH$_2$—CHOH—CH$_2$—O— chain bound to a cyclodextrin unit of said polymer or copolymer.

7. A solid according to claim 1, wherein the organic surface agent is a branched polyethylene glycol having the following structure:

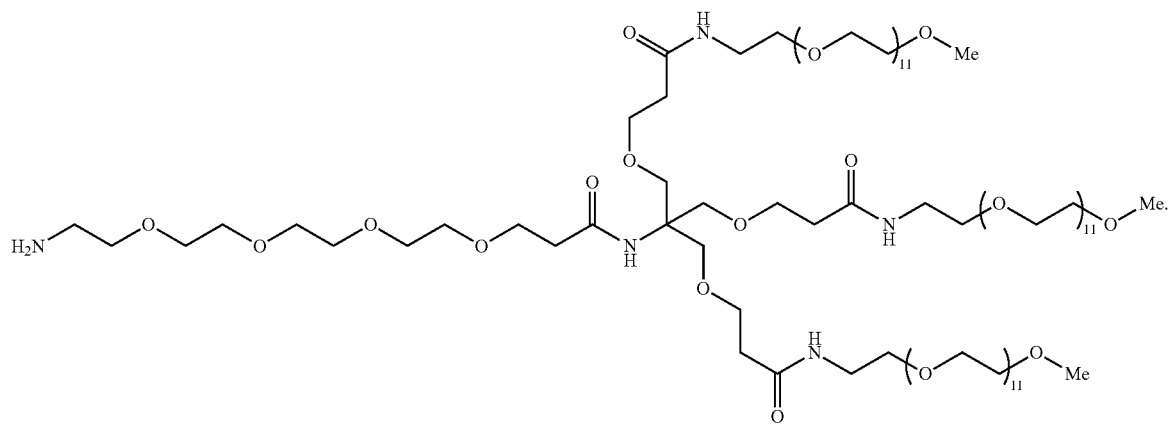

8. A solid according to claim 1, wherein the organic surface agent is further functionalized with a fluorescent molecule.

9. A solid according to claim 8, wherein the fluorescent molecule is rhodamine, fluorescein, luciferase, pyrene or derivatives thereof, aminopyrrolidino-7-nitrobenzofurazan, or a quantum dot.

10. A solid according to claim 1, said solid comprising in its pores or on its surface at least one pharmaceutically active ingredient and/or an active substance included in the formulation of a cosmetic preparation and/or a marker.

11. A solid according to claim 10, wherein the pharmaceutically active ingredient is an anticancer, antiviral, antibiotic, anti-inflammatory or analgesic agent.

12. A solid according to claim 11, wherein the anticancer agent is selected from the group comprising: busulfan, azidothymidine (AZT), azidothymidine phosphate (AZTP), cidofovir, gemcitabine, zalcitabine (ddC), didanosine (ddI), ibuprofen.

13. A method for preparing a solid as defined in claim 1, comprising:

a) at least one reaction step (i) consisting in mixing, in a polar solvent:
   at least one solution comprising at least one inorganic metal precursor, said precursor being in the form of metal M, of a salt of metal M or of a coordination complex comprising the metal ion M wherein M is as defined in claim 1;
   at least one ligand L' of formula -R$^0$(COR$^3$)$_q$,

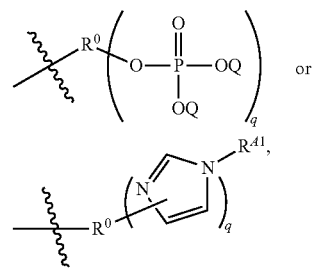

wherein Q, R$^{41}$, q and R$^0$ are as defined in claim 1, and R$^3$ is selected from the group comprising a radical —OH, a radical —OY wherein Y represents an alkali metal cation, a halogen atom, or a radical —OR$^4$, —O—C(=O)R$^4$ or —NR$^4$R$^{4\prime}$, wherein R$^4$ and R$^{4\prime}$ are C$_{1-12}$ alkyl radicals; so as to obtain a porous crystalline MOF solid;

b) a step (ii) of fixation, on the outer surface of the solid obtained in step (a), of at least one organic surface agent comprising: i) at least one phosphate, phosphonate, bisphosphonate, sulfate, carboxylate, hydroxy, cathecolate, thiolate (—SR or —S$^-$), N-containing heterocyclic, amido (—C(=O)N(R)$_2$), amino (—N(R)$_2$) group, or a combination of these groups, wherein each occurrence of R represents independently H, C$_{1-6}$alkyl or phenyl;

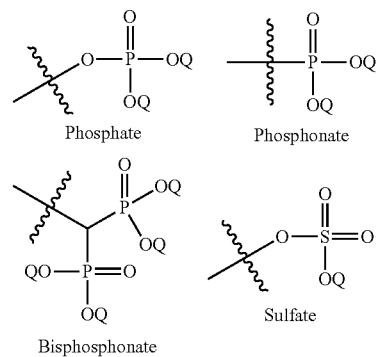

Phosphate    Phosphonate

Bisphosphonate    Sulfate

-continued

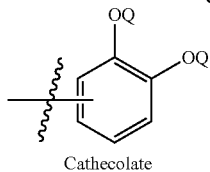
Cathecolate wherein each occurrence of Q represents independently H or an alkali metal cation;

and/or ii) a rigid section larger than the largest sized pore access windows of the MOF material the organic surface agent being selected from α-, β- or γ-cyclodextrins;

oligomers of α-,β- or γ-cyclodextrins;

poly-α, poly-β or poly-γ-cyclodextrins, copolymers of α, β and/or γ-cyclodextrins, PEG dendrimers, chitosan bearing a plurality of PEG side chains, albumin, immunoglobulins, or dextran grafted both with PEG chains and alendronate bisphosphonate groups;

so as to obtain said solid wherein said organic surface agent interacts with a metal center M or with a ligand L on the outer surface of the crystalline MOF solid via said one or more phosphate, phosphonate, bisphosphonate, sulfate, carboxylate, hydroxy, cathecolate, thiolate, N-containing heterocyclic, amido, amino group(s), or a combination of these groups.

14. A method according to claim 13, wherein the ligand L' represents a ligand bearing several complexing groups comprising carboxylate, phosphonate, imidazolate groups, wherein the carboxylate group is a di-, tri-, tetra- or hexa-dentate ligand selected from the group comprising:

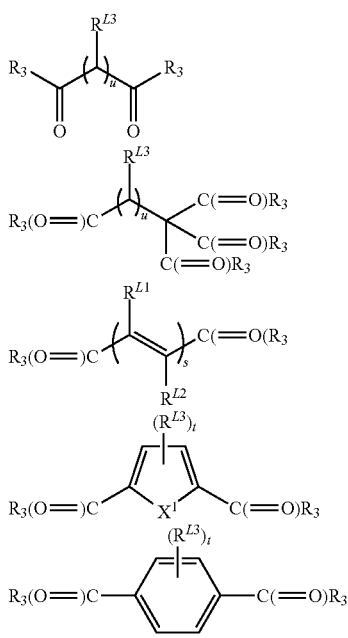

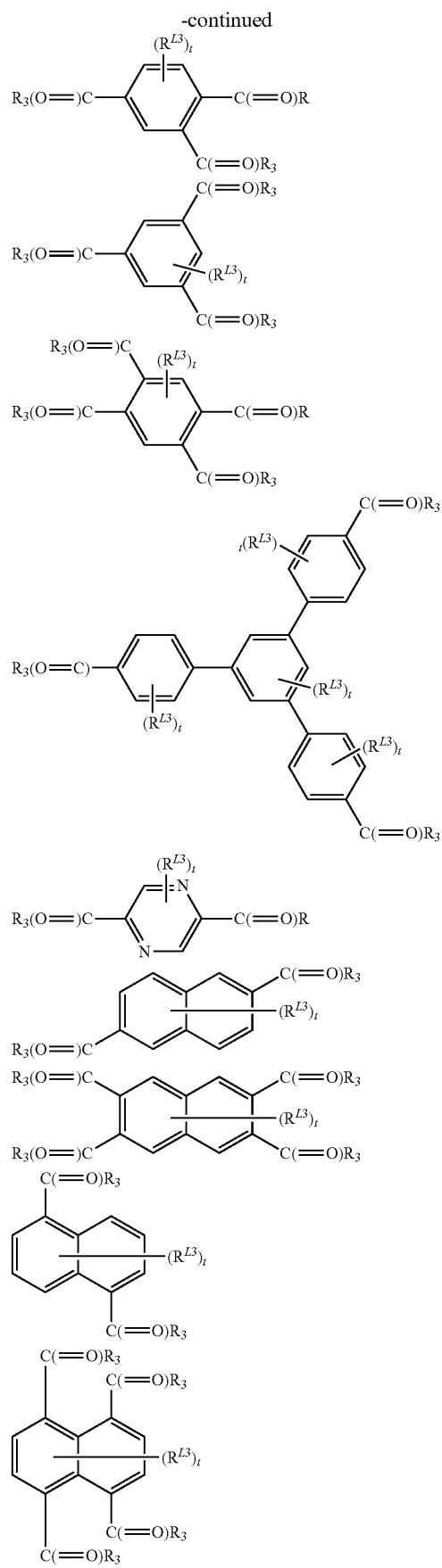

-continued

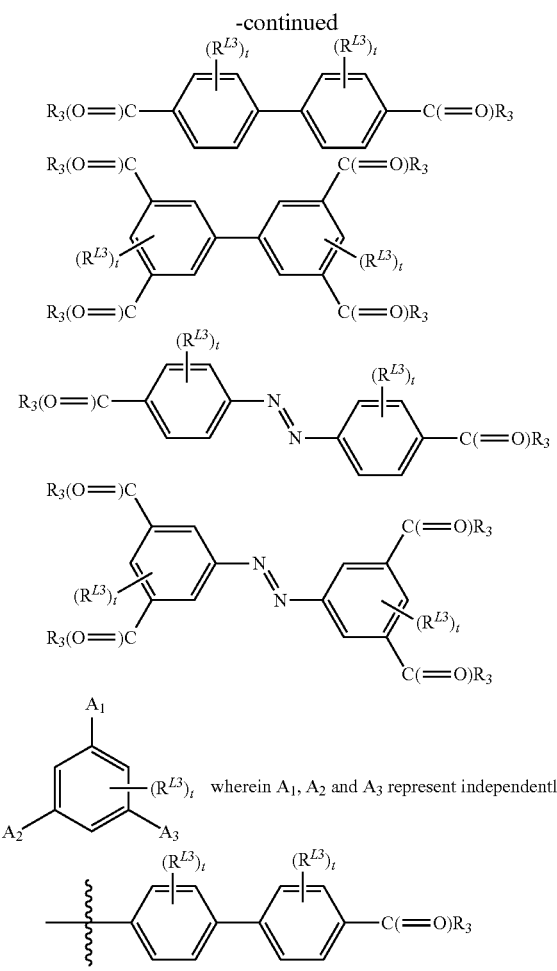

wherein $A_1$, $A_2$ and $A_3$ represent independently wherein:

$R_3$ is selected from the group comprising a radical —OH, a radical —OY wherein Y represents an alkali metal cation, a halogen atom, or a radical —OR$^4$, —O—C(=O)R$^4$ or —NR$^4$R$^{4'}$, wherein R$^4$ and R$^{4'}$ are C$_{1-12}$ alkyl radicals, $X_1$ represents O or S, s represents an integer from 1 to 4, each occurrence of t represents independently an integer from 1 to 4, u represents an integer from 1 to 7, $R^{L1}$ and $R^{L2}$ represent independently H, a halogen atom or a C$_1$ to C$_6$ alkyl, and each occurrence of $R^{L3}$ represents independently H, a halogen atom, OH, NH$_2$, NO$_2$ or a C$_1$ to C$_6$ alkyl.

15. A method according to claim 13, wherein the organic surface agent is as defined in any one of claims 1 and 6 to 10.

16. A method for preparing the solid as claimed in claim 13, wherein reaction step (i) is carried out with at least one of the following reaction conditions:

(i) a reaction temperature from 0° C. to 220° C.;
(ii) a stirring speed from 0 to 1000 rpm;
(iii) a reaction time from 1 minute to 96 hours;
(iv) a pH from 0 to 7;
(v) addition of at least one co-solvent to the solvent, to the precursor, to the ligand or to a mixture thereof, said co-solvent being selected from the group comprising acetic acid, formic acid, benzoic acid;
(vi) the solvent is selected from the group comprising water, the alcohols R$^s$—OH wherein R$^s$ is a linear or branched C$_1$ to C$_6$ alkyl radical, dimethylformamide, dimethylsulfoxide, acetonitrile, tetrahydrofuran, diethylformamide, chloroform, cyclohexane, acetone, cyanobenzene, dichloromethane, nitrobenzene, ethylene glycol, dimethylacetamide or mixtures of these solvents, miscible or not;
(vii) in a supercritical medium;
(viii) under microwaves and/or under ultrasound;
(ix) under conditions of electrochemical electrolysis;
(x) under conditions using a rolling crusher;
(xi) in a gas stream.

17. A method according to claim 13, further comprising a step (iii) of introducing at least one pharmaceutically active ingredient into said solid.

18. A solid obtainable by a method as claimed in claim 13.

19. A medicament comprising a solid according to claim 1 and a pharmaceutically active ingredient.

20. A medical imaging marker comprising a MOF solid according to claim 1.

* * * * *

UNITED STATES PATENT AND TRADEMARK OFFICE
CERTIFICATE OF CORRECTION

| | | |
|---|---|---|
| PATENT NO. | : 10,159,738 B2 | Page 1 of 1 |
| APPLICATION NO. | : 14/403277 | |
| DATED | : December 25, 2018 | |
| INVENTOR(S) | : Gref et al. | |

It is certified that error appears in the above-identified patent and that said Letters Patent is hereby corrected as shown below:

On the Title Page

At item (73), Assignee:
Delete "CENTRE NATIONAL DE LA RECHERCHE SCIENTIFIQUE-CNRS, Paris (FR); UNIVERSITE DE VERSAILLES-SAINT QUENTIN EN YVELINES, Versailles (FR); UNIVERSITE PARIS-SUD, Orsay (FR)" and insert -- CENTRE NATIONAL DE LA RECHERCHE SCIENTIFIQUE-CNRS, Paris-Cedex (FR); UNIVERSITE PARIS-SUD, Orsay (FR). --

Signed and Sealed this
Seventh Day of February, 2023

Katherine Kelly Vidal
*Director of the United States Patent and Trademark Office*